US011674915B2

(12) United States Patent
Potyrailo et al.

(10) Patent No.: US 11,674,915 B2
(45) Date of Patent: Jun. 13, 2023

(54) SENSING SYSTEM AND METHOD

(71) Applicant: General Electric Company, Schenectady, NY (US)

(72) Inventors: Radislav Alexandrovich Potyrailo, Niskayuna, NY (US); Daniel White Sexton, Niskayuna, NY (US); Steven Y. Go, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 16/995,427

(22) Filed: Aug. 17, 2020

(65) Prior Publication Data

US 2021/0033552 A1 Feb. 4, 2021

Related U.S. Application Data

(63) Continuation of application No. 15/060,193, filed on Mar. 3, 2016, now Pat. No. 10,746,680, which is a continuation-in-part of application No. 14/866,320, filed on Sep. 25, 2015, now Pat. No. 10,018,613, which is a continuation-in-part of application No. 14/421,245, filed on Feb. 12, 2015, now Pat. No.
(Continued)

(51) Int. Cl.
*G01N 27/02* (2006.01)
*G01N 33/28* (2006.01)

(52) U.S. Cl.
CPC ....... *G01N 27/026* (2013.01); *G01N 33/2888* (2013.01)

(58) Field of Classification Search
None
See application file for complete search history.

(56) References Cited

U.S. PATENT DOCUMENTS 5,608,316 A * 3/1997 Crayton ............ G01N 33/2858
324/225
6,255,954 B1 * 7/2001 Brown ...................... B41J 2/01
73/304 R
(Continued)

FOREIGN PATENT DOCUMENTS

DE 102009016642 A1 10/2010
DE 202011051119 U1 10/2011
(Continued)

OTHER PUBLICATIONS

Translation of Tamai et al. (Year: 2005).*
(Continued)

*Primary Examiner* — Matthew G Marini
(74) *Attorney, Agent, or Firm* — Fletcher Yoder, P.C.

(57) ABSTRACT

A sensor system includes a multi-frequency sensor assembly including a single sensor body housing with a sensing region circuit and a sensor reader disposed in the sensor body. The sensor body is configured to be in operational contact with a fluid. The sensing region circuit is configured to generate different electric fields having different frequencies in the fluid. The sensor reader includes one or more processors configured to examine one or more impedance responses of the sensing region circuit at different frequencies and to determine one or more properties of the fluid based on the one or more impedance responses that are examined.

20 Claims, 61 Drawing Sheets

Related U.S. Application Data 9,746,452, and a continuation of application No. 14/585,690, filed on Dec. 30, 2014, now Pat. No. 10,914,698, which is a continuation-in-part of application No. 14/532,168, filed on Nov. 4, 2014, now Pat. No. 9,536,122, and a continuation-in-part of application No. 14/031,965, filed on Sep. 19, 2013, now Pat. No. 8,990,025, and a continuation-in-part of application No. 14/031,951, filed on Sep. 19, 2013, now Pat. No. 9,037,418, and a continuation-in-part of application No. 13/838,884, filed on Mar. 15, 2013, now Pat. No. 9,389,296, and a continuation-in-part of application No. 13/729,800, filed on Dec. 28, 2012, now Pat. No. 9,097,639, and a continuation-in-part of application No. 13/729,851, filed on Dec. 28, 2012, now Pat. No. 9,261,474, and a continuation-in-part of application No. 13/630,587, filed on Sep. 28, 2012, now Pat. No. 9,658,178, and a continuation-in-part of application No. 13/630,939, filed on Sep. 28, 2012, now Pat. No. 9,389,260, and a continuation-in-part of application No. 13/630,954, filed on Sep. 28, 2012, now Pat. No. 9,147,144, and a continuation-in-part of application No. 13/630,739, filed on Sep. 28, 2012, now Pat. No. 9,176,083, and a continuation-in-part of application No. 12/325,653, filed on Dec. 1, 2008, now abandoned, and a continuation-in-part of application No. 13/558,499, filed on Jul. 26, 2012, now Pat. No. 9,195,925, and a continuation-in-part of application No. 13/538,570, filed on Jun. 29, 2012, now Pat. No. 9,538,657, and a continuation-in-part of application No. 13/484,674, filed on May 31, 2012, now Pat. No. 9,052,263, and a continuation-in-part of application No. 13/331,003, filed on Dec. 20, 2011, now Pat. No. 9,045,973, and a continuation-in-part of application No. 12/977,568, filed on Dec. 23, 2010, now abandoned, and a continuation-in-part of application No. 12/827,623, filed on Jun. 30, 2010, now Pat. No. 8,936,191, and a continuation-in-part of application No. 12/824,436, filed on Jun. 28, 2010, now abandoned, said application No. 13/484,674 is a continuation of application No. 12/424,016, filed on Apr. 15, 2009, now Pat. No. 8,364,419, said application No. 14/585,690 is a continuation-in-part of application No. 11/560,476, filed on Nov. 16, 2006, now Pat. No. 9,589,686.

(60) Provisional application No. 61/987,853, filed on May 2, 2014, provisional application No. 61/692,230, filed on Aug. 22, 2012.

(56) References Cited

U.S. PATENT DOCUMENTS

| | | | |
|---|---|---|---|
| 6,577,112 B2 * | 6/2003 | Lvovich | G01N 33/2888 324/71.1 |
| 2003/0102050 A1 | 6/2003 | Matthews et al. | |
| 2003/0212509 A1 * | 11/2003 | Henry | G01F 1/8427 702/45 |
| 2003/0221911 A1 | 12/2003 | Eriksen et al. | |
| 2003/0222656 A1 * | 12/2003 | Phillips | G01N 27/02 324/605 |
| 2004/0020994 A1 | 2/2004 | Muehl et al. | |
| 2005/0017738 A1 * | 1/2005 | Lin | G01N 33/2888 324/698 |
| 2005/0104607 A1 * | 5/2005 | Byington | G01N 27/026 324/693 |
| 2006/0244581 A1 * | 11/2006 | Breed | B60C 23/0408 340/447 |
| 2007/0272486 A1 | 11/2007 | Eadie et al. | |
| 2008/0203735 A1 | 8/2008 | Leslie | |
| 2009/0218171 A1 | 9/2009 | Nicot | |
| 2011/0101996 A1 * | 5/2011 | Potyrailo | G01D 21/00 324/655 |

FOREIGN PATENT DOCUMENTS

| | | | |
|---|---|---|---|
| DE | 102010048950 A1 | | 4/2012 |
| GB | 2476302 A | | 6/2011 |
| JP | 2005156569 A | * | 6/2005 |
| WO | WO-0127610 A2 | * | 4/2001 ........ B01L 3/502784 |

OTHER PUBLICATIONS

Office Action dated May 21, 2021 for corresponding German Patent application No. 11 2013 004 129.4 (8 pages).

English translation of the Office Action dated May 21, 2021 for corresponding German Patent application No. 11 2013 004 129.4 (8 pages).

Office Action dated Dec. 21, 2020 for corresponding European Patent application No. EP11801234.3. (4 pages).

* cited by examiner

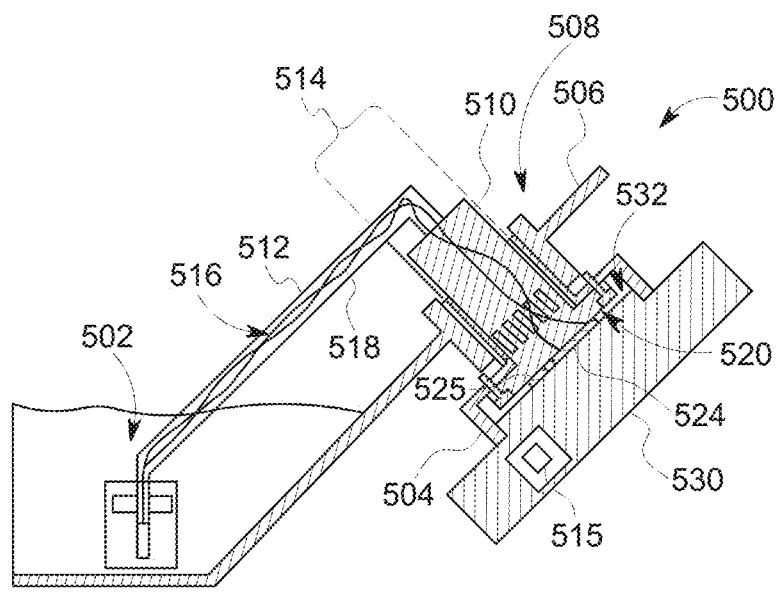
FIG. 11
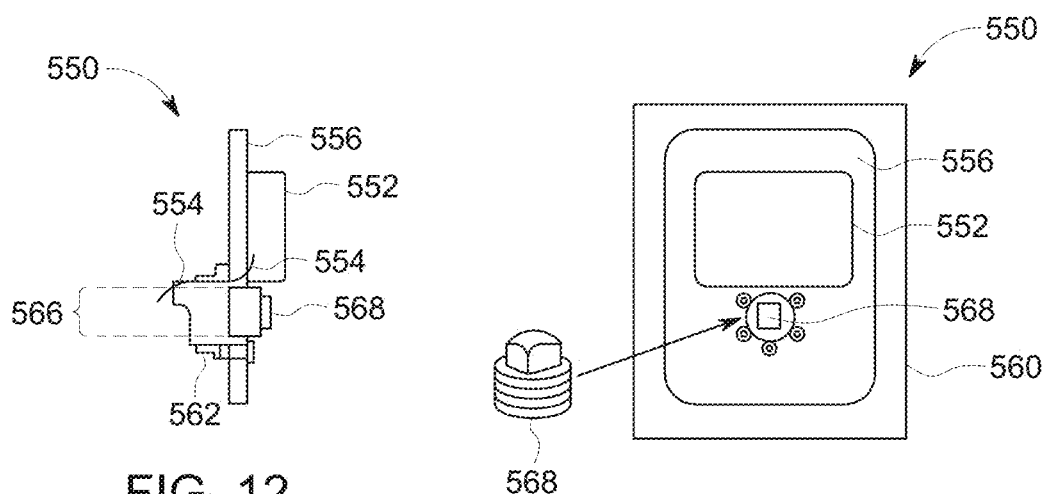
FIG. 12
FIG. 13

SENSING SYSTEM AND METHOD

CROSS-REFERENCE TO RELATED APPLICATIONS

This application is a continuation of Ser. No. 15/060,193, filed 18 Aug. 2020 (now U.S. Pat. No. 10,746,680), which is a continuation-in-part of U.S. patent application Ser. No. 14/866,320, filed 25 Sep. 2015 (the "'320 Application"), which is a continuation-in-part of U.S. patent application Ser. No. 14/421,245, filed on 12 Feb. 2015 (the "'245 Application"), which claims the benefit of U.S. Provisional Patent Application No. 61/692,230, filed on 22 Aug. 2012 (the "'230 Application").

The '320 Application also is a continuation-in-part of U.S. patent application Ser. No. 14/585,690, filed on 30 Dec. 2014 (the "'690 Application"), which claims priority to U.S. Provisional Patent Application No. 61/987,853, filed on 2 May 2014 (the "'853 Application").

The '690 Application is a continuation-in-part of the following applications: U.S. patent application Ser. No. 11/560,476, filed on 16 Nov. 2006 (the "'476 Application"), U.S. patent application Ser. No. 12/325,653, filed on 1 Dec. 2008 (the "'653 Application"), U.S. patent application Ser. No. 12/824,436, filed on 28 Jun. 2010 (the "'436 Application"), U.S. patent application Ser. No. 12/827,623, filed on 30 Jun. 2010 (the "'623 Application"), U.S. patent application Ser. No. 12/977,568, filed on 23 Dec. 2010 (the "'568 Application"), U.S. patent application Ser. No. 13/331,003, filed on 20 Dec. 2011 (the "'003 Application"), U.S. patent application Ser. No. 13/484,674, filed on 31 May 2012 (the "'674 Application"), U.S. patent application Ser. No. 13/538,570, filed on 29 Jun. 2012 (the "'570 Application"), U.S. patent application Ser. No. 13/558,499, filed on 26 Jul. 2012 (the "'499 Application"), U.S. patent application Ser. No. 13/630,939, filed on 28 Sep. 2012 (the "'939 Application"), U.S. patent application Ser. No. 13/630,954, filed on 28 Sep. 2012 (the "'954 Application"), U.S. patent application Ser. No. 13/630,587, filed on 28 Sep. 2012 (the "'587 Application"), U.S. patent application Ser. No. 13/630,739, filed on 28 Sep. 2012 (the "'739 Application"), U.S. patent application Ser. No. 13/729,800, filed on 28 Dec. 2012 (the "'800 Application"), U.S. patent application Ser. No. 13/729,851, filed on 28 Dec. 2012 (the "'851 Application"), U.S. patent application Ser. No. 13/838,884, filed on 15 Mar. 2013 (the "'884 Application"), U.S. patent application Ser. No. 14/031,951, filed on 19 Sep. 2013 (the "'951 Application"), U.S. patent application Ser. No. 14/031,965, filed on 19 Sep. 2013 (the "'965 Application"), and U.S. patent application Ser. No. 14/532,168, filed on 4 Nov. 2014 (the "'168 Application").

The '674 Application is a continuation-in-part of U.S. patent application Ser. No. 12/424,016, filed on 15 Apr. 2009, and is now U.S. Pat. No. 8,364,419, issued on 29 Jan. 2013 (the "'419 Patent").

All the aforementioned applications and patents are incorporated herein by reference in their entireties.

FIELD

One or more embodiments of the subject matter described herein generally relate to systems and methods for detecting an operative condition of a machine or a component of the machine that has movable parts. One or more embodiments of the subject matter described herein generally relate to systems and method for detecting an operative condition of a machine or a component of the machine that does not have movable parts and/or a naturally occurring system that has or does not have movable parts. One or more embodiments are disclosed that relate to sensing methods and systems. The sensors, such as resonant sensors, may include inductor-capacitor-resistor (LCR) sensors that can be used as sensors or transducers for sensing fluids.

BACKGROUND

Many industrial machines (e.g., locomotives, trucks, earth-moving equipment, windmills, and the like) include elements or assemblies (e.g., mechanical drive trains) that operate within difficult environments and/or endure substantial amounts of thermal or torsional stress as well as shock and vibration. It is often desirable to monitor a condition of an element or assembly so that it may be replaced or repaired before severe and permanent damage is sustained by the machine. Often, fluid lubricants are used to provide lubrication and cooling to increase performance of the machine and/or to increase the lifetime operation of the machine. Lubricants reduce the friction between two parts that engage each other and may also dissipate heat that is generated by the friction between the two parts. In addition to lubricants, fluids include other industrial fluid such as fuels, hydraulic media, drive fluids, power steering fluids, power brake fluids, drilling fluids, oils, insulating fluids, heat transfer fluids, or the like. Such fluids allow efficient and safe operation of machinery in transportation, industrial, locomotive, marine, automotive, construction, medical, and other applications. Fluids also include naturally occurring fluids such as oils, water, body fluids, biological fluids, and the like that occur in natural living and non-living systems. As one specific example, speed control from a traction motor or other provider of mechanical power may be accomplished with a gear train or drive train. Gear trains typically include at least two gears that engage each other. For instance, teeth of a first gear (e.g., pinion gear) may engage teeth of a larger gear at a gear mesh. It is common for the gears to be lubricated by a lubricant (e.g., oil) to reduce the friction between the gears and to facilitate the dissipation of heat that is generated during operation. In order for the gears to be suitably lubricated, a designated amount of lubricant is available for use by the gears.

A gear train may include a gear case that surrounds one or more parts of the gear train. The gear case has a reservoir for holding the lubricant. At least one of the gears may move through the reservoir to lubricate the gear and consequently the gear mesh. At least one of the gears may be coupled to a shaft that projects out of the gear case. To prevent leakage from the reservoir or the gear case, the interface between the shaft(s) and the gear case is sealed.

The sealed interfaces, however, are often exposed to harsh conditions. For example, gear trains of locomotives are frequently exposed to large differences in temperature, humid environments, dry environments, abrasive dirt or grime, and/or challenging vibratory states. These conditions may cause a failure in the sealed interface thereby resulting in leakage of the lubricant. When an insufficient supply of lubricant is available for the gears, the machine may be susceptible to gear train or rolling element bearing damage that results in a locked axle condition. In the case of locomotives, locked axles may require the locomotive to be removed from service and sent to a facility for repair. Both the removal and repair of the locomotive may be time-consuming and costly. Furthermore, the lost productivity of the locomotive is also costly.

In addition to having a sufficient amount of lubricant, it is also desirable for the lubricant to have a sufficient quality during operation. For example, lubricants in a reservoir can become contaminated by water, metallic particles, and non-metallic particles. Contaminated fluids may lead to damaged parts or a decreased performance of the machine. In addition, the lubricant may age due to repetitive thermal and viscous cycles resulting in the loss of fluid properties such as viscosity.

Conventional methods of inspecting fluids of a machine include visual inspection of the fluid (e.g., dipsticks) or a sensor that is directly wired to a system. These methods may not be practical and/or may have limited capabilities. For example, due to the configuration of some machines, it may be difficult to visually inspect the fluid. Also, hardwired sensors may not be suitable for machines that frequently move and/or are exposed to harsh conditions.

In addition to detecting the quantity and/or the quality of a liquid used by a machine, it may be desirable to obtain other information regarding an operative condition of a machine. For example, when an industrial machine is operating properly, the machine may have known or expected vibratory states. When a part of the machine is damaged or otherwise not operating properly, however, the vibrations of the machine may change. Therefore, it may be desirable to detect the vibrations of certain elements in a machine to monitor a health of the elements, other components of the machine, or the machine overall.

Robust sensing of fluids may be useful in mobile and stationary equipment applications. As one example, if the equipment is a vehicle engine and the fluid is engine oil, then knowledge about oil health may be used to help reduce or prevent unexpected downtime, provide savings from unnecessary oil replacement, and improve service intervals scheduling in vehicles such as locomotives, heavy and light duty trucks; mining, construction, and agriculture vehicles. Other examples of stationary equipment applications may include wind turbines and gensets. Further, knowledge about engine oil health may prevent or reduce the total life cost of passenger cars, improve control of service intervals, and extend the life of engine.

Standard (classic) impedance spectroscopy is a technique that is employed to characterize examples of material performance. In classic impedance spectroscopy, a material may be positioned between electrodes and probed over a wide frequency range (from a fraction of Hz to tens of GHz) to extract the fundamental information about dielectric properties of the material. Standard impedance spectroscopy may be limited due to its low sensitivity in reported measurement configurations and prohibitively long acquisition times over the broad frequency range.

It may be desirable to have systems and methods that differ from those systems and methods that are currently available.

BRIEF DESCRIPTION

In accordance with an embodiment, a system (e.g., a monitoring or sensing system) is provided that includes a sensor configured to be disposed within a reservoir of a machine having moving parts that are lubricated by a liquid in the reservoir. The sensor is configured to obtain a measurement of the liquid that is representative of at least one of quantities or qualities of the liquid in the reservoir related to external contaminants and oil aging. The system may also include a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader. A reader also may be referred to as a sensor reader.

In an embodiment, a system (e.g., a monitoring or sensing system) is provided that includes a sensor that is configured to be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that is configured to wirelessly communicate the first data signals to a remote reader.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train and its lubricating oil condition determined by a multivariable sensor for monitoring external contaminants and oil aging. The method also includes, responsive to determining that the drive train is operating improperly, generating signals to schedule at least one of maintenance of the drive train or replacement of an element of the drive train.

In an embodiment, a system (e.g., a monitoring or sensing system) includes a signal-processing module that is configured to receive data signals from a wireless device of a machine having a drive train. The data signals are based on a measurement of an operative condition of the drive train. The signal-processing module is configured to determine, based on the dynamic data signals provided by at least two identical sensors, whether the drive train is operating improperly. Optionally, the system also includes a planning module that is configured to generate an operating plan that is based on the operative condition.

One embodiment of the disclosure provides a system for analyzing fluid. The system may include a sensor. The sensor may include a resonant inductor-capacitor-resistor (LCR) circuit, a sensing region that includes at least a portion of the LCR circuit, a controller coupled to the sensing region. The sensing region may be placed in operational contact with a fluid of interest. The controller may receive an electrical signal from the sensor. The signal may represent resonant impedance spectra of the sensing region during operational contact with the fluid over a measured spectral frequency range. The signal may be used to analyze the resonant impedance spectra, and to determine one or more properties of the fluid such as external contaminants of the fluid and fluid aging based on the analyzed resonant impedance spectra.

In one embodiment, a method includes exciting a sensor in contact with a fluid. The sensor may include an LCR resonant circuit to operate at one or more frequencies in a frequency range of analysis. A signal may be received from the sensor across the frequency range of analysis. The signal includes information about a sensor in contact with the fluid. One or more properties of the fluid may be determined based at least in part on the resonant impedance spectra.

A system is provided in one embodiment that includes a resonant sensor and a controller. The sensor can sense a complex permittivity of a fluid across a broad dispersion range of external contaminants of the fluid and across a broad dispersion range of fluid aging compounds. The controller may be coupled to the sensor and can receive an electrical signal from the sensor. The signal may represent at least two resonant impedance spectra of the fluid over a measured spectral frequency range. The controller may determine a complex permittivity of the fluid based at least in part on the resonant impedance spectra.

In an embodiment, a system includes a sensor and a device body. The sensor has a sensing region including multiple electrode structures and at least one resonant inductor-capacitor-resistor (LCR) circuit. Each electrode structure includes at least two electrodes. The sensing region is configured to be placed in operational contact with an industrial fluid of interest. The at least one resonant LCR circuit is electrically connected to the electrode structures and configured to generate an electrical stimulus having a spectral frequency range. The electrical stimulus is applied to the industrial fluid via the electrode structures. The device body is operably coupled to the sensor. The device body includes one or more processors configured to receive an electrical signal from the sensor that is representative of a resonant impedance spectral response of the sensing region in operational contact with the industrial fluid responsive to the electrical stimulus being applied to the industrial fluid. The one or more processors are configured to analyze the resonant impedance spectral response and determine both a concentration of an external contaminant in the industrial fluid and an aging level of the industrial fluid based on the resonant impedance spectral response that is analyzed.

In another embodiment, a method includes applying an electrical stimulus to an industrial fluid using a sensor. The sensor includes at least one resonant inductor-capacitor-resistor (LCR) circuit configured to generate the electrical stimulus. The electrical stimulus is applied to the industrial fluid via multiple electrode structures at a sensing region of the sensor in operational contact with the industrial fluid. The method includes receiving an electrical signal from the sensor representative of a resonant impedance spectral response of the sensing region in operational contact with the industrial fluid responsive to the electrical stimulus being applied to the industrial fluid. The method also includes analyzing, using one or more processors, the resonant impedance spectral response to determine both a concentration of an external contaminant in the industrial fluid and an aging level of the industrial fluid based on the resonant impedance spectral response that is analyzed.

In another embodiment, a system for monitoring a condition of an industrial site includes a sensor with at least two sufficiently non-correlated output signals representative of a response of the sensor to an industrial fluid at the industrial site. The system also includes a device body operably coupled to the sensor. The device body includes one or more processors configured to receive the output signals from the sensor and analyze the output signals to determine both a concentration of an external contaminant in the industrial fluid and an aging level of the industrial fluid based on the output signals.

While multiple embodiments are disclosed, still other embodiments of the described subject matter will become apparent from the following Detailed Description, which shows and describes illustrative embodiments of disclosed inventive subject matter. As will be realized, the inventive subject matter is capable of modifications in various examples, all without departing from the spirit and scope of the described subject matter. Accordingly, the drawings and detailed description are to be regarded as illustrative in nature and not restrictive.

BRIEF DESCRIPTION OF THE DRAWINGS

FIG. 11 is a cross-section of a wireless device utilizing the sensor of FIG. 5 in accordance with an embodiment.

FIG. 12 is a cross-section of a portion of a wireless device formed in accordance with an embodiment.

FIG. 13 is a front view of the wireless device of FIG. 12.

DETAILED DESCRIPTION

Figure 1:
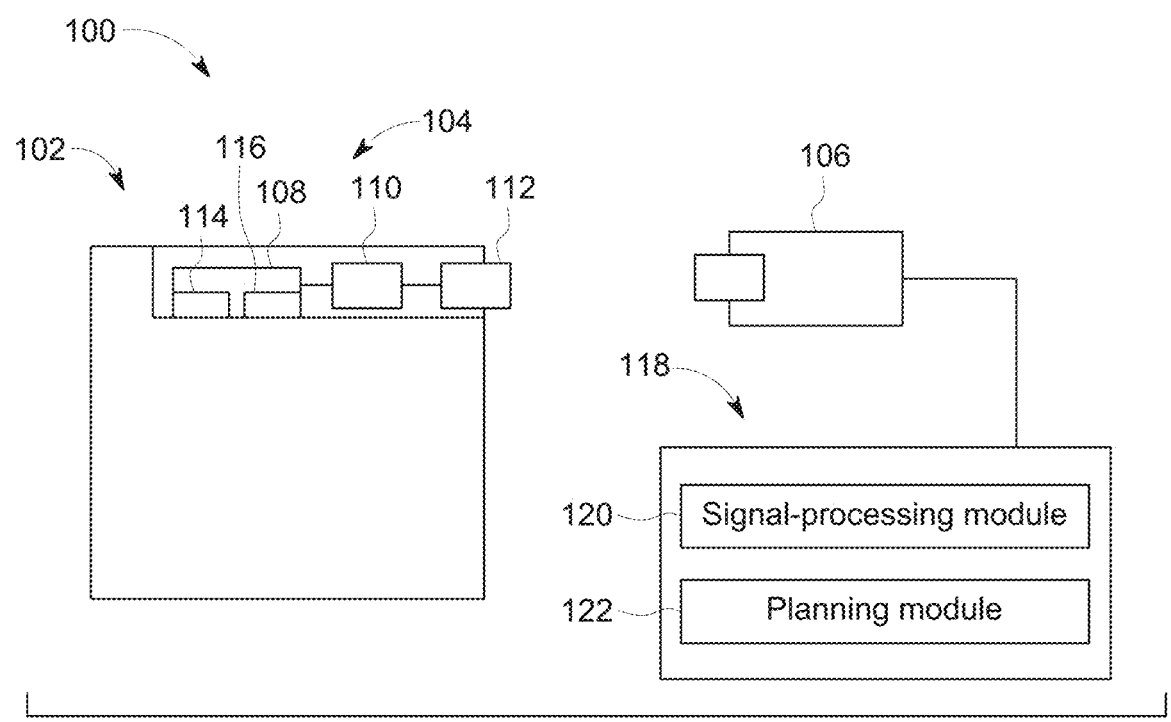
FIG. 1 is a schematic view of a system in accordance with an embodiment.

Embodiments described herein include various systems, assemblies, devices, apparatuses, and methods that may be used in a connection with obtaining one or more measurements of a machine. The measurement(s) may be representative or indicative of an operative condition of the machine. As used herein, an operative condition of the machine may refer to an operative condition of the machine as a whole or an operative condition of a component (e.g., element, assembly, or sub-system) of the machine. As used herein, the operative condition of a machine can relate to a present state or ability of the component and/or a future state or ability of the machine to perform one or more operations. For example, the measurement or operative condition may indicate that the machine or a component of the machine is not functioning in a sufficient manner, is damaged, is likely to be damaged if it continues to operate in a designated manner, is not likely to perform appropriately under designated circumstances, and/or is likely to cause damage to other components of the machine. Alternatively, the measurement or operative condition may indicate that the machine or component is operating normally or is not damaged.

As one example with respect to locomotives or other rail vehicles, one or more measurements obtained from a locomotive or other rail vehicle may indicate that a lubricant in the component (e.g., drive train, gearbox, engine, and the like) is low or has an insufficient quality. Embodiments set forth herein may generate an operating plan that is based on the measurement(s). For instance, the operating plan may include instructions to disable an axle or to limit tractive and/or braking efforts of the axle. The operating plan may indicate which element of the gearbox should be replaced and/or how the machine is to be operated until the gearbox is replaced. Such operating plans are described in greater detail below.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking. Embodiments may also comprise analyzing measurements from a plurality of sensors of the same type. For example, machines may include multiple gearboxes. Vibration measurements from the gearboxes may indicate that one of the gearboxes is operating differently than the others and, thus, may be damaged or in need of maintenance. Embodiments may also comprise analyzing different types of measurements to determine an operative condition of the machine. For example, the vibration measurements may be analyzed in light of the speed at which the gears are driven and/or current environmental conditions. Additional measurements or factors are set forth below.

The measurements may be wirelessly transmitted from a device to a reader, which may also be referred to as a receiver. For example, radio waves representative of the measurement(s) may be transmitted from a transmitter (e.g., antenna) of the wireless device to a remote reader. The reader may be a handheld reader (e.g., capable of being carried in a single hand by a technician) or an otherwise movable reader. In some embodiments, the reader may have a fixed position. For example, for embodiments in which the machine is a vehicle, the reader may have a stationary position along a designated path that is traversed by the vehicle (e.g., railroad tracks, weighing stations, tollbooths). When a vehicle passes the reader, the reader may interrogate one or more wireless devices to obtain measurements. Remote readers may also be located on-board the vehicle. For example, a locomotive or other rail vehicle may have a control system that receives data from multiple sources, including one or more wireless devices that communicate the measurements to the control system.

The measurement may be detected or obtained by a sensor when the device having the sensor is interrogated by the reader. Alternatively or additionally, the sensor may obtain data at designated intervals (e.g., one measurement/hour, one measurement/minute, and the like) and/or when a designated event occurs. For example, measurements may only be obtained after the vehicle has been interrogated or after the vehicle has remained stationary for a certain amount of time (e.g., ten minutes) or after the vehicle has started to move for a certain amount of time (e.g., one minute). In some embodiments, the wireless device includes a storage unit (e.g., memory) where multiple measurements may be stored or logged. The wireless devices may also include a power source that is integral to the device. Examples of electrical power sources include batteries and energy harvesting devices. Energy harvesting devices convert energy in the surrounding environment, such as kinetic energy (e.g., vibrations), thermal energy, and electromagnetic energy. In particular embodiments, the wireless devices may include or be coupled to a vibratory energy harvesting device that converts kinetic energy into electrical energy.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

FIG. 1 is a schematic diagram of a monitoring or sensing system 100 formed in accordance with one embodiment. The system 100 is configured to obtain one or more measurements that are representative of an operative condition of a machine 102 or a component of the machine 102 (e.g., element, assembly, or sub-system of the machine 102). By way of example only, the machine 102 may be a motive machine or vehicle, such as an off-highway vehicle (e.g., vehicles that are not designed or allowed by law or regulation to travel on public roads, highways, and the like). Off-highway vehicles include locomotives, mining vehicles, construction equipment, agricultural equipment, industrial equipment, marine vessels, and the like. In some cases, the vehicle may be part of a vehicle consist in which multiple vehicles are linked directly or indirectly to one another in a common vehicle system (e.g., train). In some embodiments, the machine is an automobile. In other embodiments, the machine is not configured to travel. For example, the machine may be a windmill or a power-generating turbine or a transformer.

The operative condition may relate to a health or status of a designated component of the machine. Non-limiting examples of such components include a gearbox, a gear case, an air compressor, a turbo-charger, or a drive train. The measurement may be analyzed to determine, for example, that a component is damaged, is operating improperly (e.g., insufficiently or not at all), and/or is operating in a manner that will lead to or cause greater damage to the component or other component of the machine 102.

In particular embodiments, the operative condition is determined based on an amount or quality of liquid used by the machine 102 and/or a vibratory state of the machine 102. For instance, in some embodiments, the component may be a gear case that has a reservoir for storing a lubricant liquid. A low level or quantity of the liquid in the reservoir may indicate that the gear case is damaged. In particular, a low level or quantity may indicate that the gear case is leaking the liquid. In other embodiments, a component may have a particular vibratory state(s) when the component is operating properly. For example, a mechanical element may be configured to oscillate in a known or expected manner during operation. However, if the mechanical element is damaged or operating improperly, the mechanical element may have a different vibratory state.

As shown, the system 100 may include a wireless device 104 that is configured to wirelessly communicate data signals to a remote reader 106. The data signals may represent the measurement(s) obtained by the wireless device 104. To this end, the wireless device 104 may include a sensor 108, a processing unit 110 (also referred to as a controller or computer), and a transmitter 112. The sensor 108 is configured to measure an operating parameter of the machine 102 and thereby obtain a measurement. In some embodiments, the sensor 108 includes a detector or transducer 114 and an activator 116. The activator 116 may be configured to provide a stimulus (e.g., sound waves, light, electric current, etc.) that causes a response by a component-of-interest or is affected by the component-of-interest. The detector 114 may be configured to detect the response that is caused by the stimulus or the affect that the component-of-interest has on the stimulus. For example, the stimulus may be sound waves that are detected to determine a liquid level (e.g., sonar). The stimulus may be light signals that are projected by a laser into a liquid to determine how much of the light signals are absorbed by the liquid. Another stimulus may be electric current. In other embodiments, the sensor 108 does not include an activator 116. Instead, the detector 114 may detect sound, vibrations, light, temperature, electrical properties, or other properties that occur in the environment without a stimulus provided by an activator.

The processing unit 110 is operably coupled to the sensor 108. The processing unit 110 is configured to receive measurement signals from the sensor 108 and process the measurement signals to provide data signals. The processing unit 110 may be an analog-to-digital converter (ADC). Alternatively or in addition to the ADC, the processing unit 110 may include a logic-based device that transforms the measurement signals into data signals. The data signals may then be configured to be transmitted to the reader 106 by the transmitter 112. For example, the processing unit 110 may be a computer processor, controller (e.g., microcontroller) or other logic-based device that performs operations based on one or more sets of instructions (e.g., software). The instructions on which the processing unit 110 operates may be stored on a tangible and non-transitory (e.g., not a transient signal) computer readable storage medium, such as a memory. The memory may include one or more types of memory, such as hard drives, flash drives, RAM, ROM, EEPROM, and the like. Alternatively, one or more of the sets of instructions that direct operations of the processing unit 110 may be hard-wired into the logic of the processing unit 110, such as by being hard-wired logic formed in the hardware of the processing unit 110.

The transmitter 112 is operably coupled to the processing unit 110 and is configured to wirelessly communicate the data signals to the reader 106. In some embodiments, the transmitter 112 is a transceiver that is configured to transmit the data signals and receive other signals, such as interrogation signals from the reader 106.

In some embodiments, the sensor 108, the processing unit 110, and the transmitter 112 are localized within and/or attached directly to the machine such that the sensor 108, the processing unit 110, and the transmitter 112 are proximate to each other and form a single device. In one embodiment, the sensor 108, processing unit 110, and transmitter 112 are located inside a single continuous or contiguous body, such as a single external housing. The sensor 108, the processing unit 110, and the transmitter 112 may be in a localized spatial region of the machine that is separate from a computing system that controls operation of the machine. For example, the processing unit 110 and the transmitter 112 may be integrated with the same component such that the processing unit 110 and the transmitter 112 have fixed positions with each other. More specifically, the processing unit 110 and the transmitter 112 may be at least partially integrated onto a common component (e.g., circuit board) and/or positioned within a common container or housing that is coupled to the machine. The common container may not be coextensive with the machine and, instead, may be a separate component that is attached to or disposed within the machine-of-interest. By way of example only, some or all of the components of the processing unit 110 and the transmitter 112 may be located within 50 cm of each other, 20 cm of each other, 10 cm of each other or, more particularly, within 5 cm of each other.

In some embodiments, the processing unit 110 and the transmitter 112 may be part of a common radio frequency identification (RFID) unit (e.g., tag, chip, card, and the like). Optionally, the sensor 108 may also be part of the common RFID unit. In other cases, the sensor 108 is separate from, but operably coupled to, the RFID unit and is only a short distance from the RFID unit. For example, the sensor 108 may be located within 50 cm or less of the RFID unit and communicatively coupled via wires or wireless communication. The RFID unit may be formed in accordance with RFID technology, which may include integrated circuit technology. For example, the RFID unit may be an electronic circuit that is capable of wireless communication. In some instances, the RFID unit may satisfy one or more established RFID standards and/or guidelines, such as standards and guidelines formed by the International Organization for Standardization (ISO), the International Electrotechnical Commission (IEC), ASTM International, the DASH7 Alliance, EPCglobal, the Financial Services Technology Consortium (FSTC).

In certain embodiments, the wireless device 104 is not physically electrically connected (e.g., not connected by wires or other conductors) to any of the one or more computers or other controller-based units in the machine. For example, in the context of trains, the wireless device 104 may be partially disposed within a reservoir and/or attached to a wall that defines the reservoir and is not physically electrically connected to the computing system that controls operation of the train. In such embodiments, the data signals from the wireless device 104 may be wirelessly transmitted from the wireless device 104 to, for example, a reader that is on-board or off-board. More specifically, the data signals may not be transmitted via wire/cables or other physical electrical connections. In one or more embodiments, at least portions of the processing unit 110 and the transmitter 112 may be directly connected to a wall that defines the reservoir (e.g., a wall that bears a pressure of and/or contacts the liquid in the reservoir) and/or to a structure immediately connected to the wall (e.g., support structure of the reservoir, gear case, or the like).

Various forms of wireless communication may be transmitted and received by the wireless device 104. For example, the transmitter 112 may be configured to receive and/or transmit radio signals, optical signals, signals based on sound, or signals based on magnetic or electric fields. In particular embodiments, the transmitter 112 is configured to receive and/or transmit radio signals in one or more radio frequencies. The wireless signals may be transmitted along a narrow radio band. In narrow band transmission, a single carrier frequency is used. Alternatively, the wireless signals may be transmitted within a spectrum of radio frequencies. For example, in spread spectrum transmission, the signals may be transmitted over a number of different radio frequencies within a radio band. The data signals may be modulated for transmission in accordance with any one of a number of modulation standards, such as frequency-hopping spread spectrum (FHSS), direct-sequence spread spectrum (DSSS), or chirp spread spectrum (CSS). One wireless communication standard that may be used by embodiments described herein is IEEE 802.15.4. The IEEE 802.15.4 standard may operate within one of three frequency bands: (1) 868.0-868.6 MHz; (2) 902-928 MHz; or (3) 2400-2483.5 MHz. A number of channels may be used in each of the frequency bands. Embodiments may also use frequency bands that are associated with RFID technology, such as 120-150 kHz, 13.56 MHz, 865-868 MHz, 902-028 MHz, 2450-5800 MHz, or 3.1-10 GHz. Ultra wideband (UWB) may also be used.

In some embodiments, a transmission range of the data signals and/or the signals from the reader 106 is about 0-10 meters or from about 0-20 meters. In other embodiments, the transmission range may be greater, such as up to 100 meters or more.

Various embodiments may be based on or consistent with RFID technology. For example, the wireless device 104 may be a passive sensor, a semi-passive sensor, or an active sensor. A passive sensor may not include a power source. Instead, the power may be based on inductive coupling or backscatter coupling with the reader. A passive sensor may operate over a frequency range from about 1 kHz to about 10 GHz. A semi-passive sensor may include a power source for only designated functions. For example, a battery and/or an energy harvesting device may be used to increase the transmission distance. The passive and semi-passive sensors may be particularly suitable for when the reader is present (e.g., within transmission range so that the sensors can be powered by the reader). An active sensor may include a power source for powering multiple functions (e.g., detection, reception, and transmission). Active sensors may be used in embodiments in which the reader is configured to only receive data signals and not transmit interrogation signals.

The reader 106 may be operably connected to a control system 118 having a signal-processing or diagnostic module 120 and, optionally, a planning module 122. Like the processing unit 110, the modules 120, 122 may be a computer processor, controller (e.g., microcontroller), or other logic-based device that performs operations based on one or more sets of instructions. The instructions on which the modules 120, 122 operates may be stored on a tangible and non-transitory (e.g., not a transient signal) computer readable storage medium, such as a memory. Alternatively, one or more of the sets of instructions that direct operations of the modules 120, 122 may be hard-wired into the logic of the modules 120, 122. The module 120, 122 may be located on separate devices (e.g., separate processors) or may be located on common processor.

The signal-processing module 120 may be configured to determine, based on the data signals received by the reader 106, whether the machine 102 is operating improperly. The signal-processing module 120 may determine whether the machine 102 is operating properly or improperly by analyzing the data signals that are representative of the measurements. For example, the signal-processing module 120 may use a look-up table or other databases that provides acceptable ranges of operation. If the measurement based on the data signals is not within the range, the signal-processing module 120 may determine that the machine 102 is not operating properly. In some cases, based on the measurement(s), the signal-processing module 120 may be able to determine whether a particular component of the machine 102 is in need of maintenance, repair, or replacement or whether the machine 102 requires an overhaul of a subsystem.

Based on the measurement(s), the signal-processing module 120 may request that an operating plan be generated by the planning module 122. The operating plan may be configured to improve the performance of the machine 102 and/or to limit the performance of the machine 102 to prevent damage or additional damage. The operating plan may include instructions for replacing, maintaining, modifying, and/or repairing a designated component or components of the machine 102.

The operating plan may be based on the operative condition, which is at least partially a function of the measurement(s) obtained. For instance, if a capacitive measurement indicates that the liquid level is less than sufficient, but a substantial amount remains in the gear case, then the operating plan may include instructions for refilling the liquid at a first facility and then resealing the gear case at a second facility located further away. However, if a capacitive measurement indicates that the liquid level quickly reduced to little or no measurable amount of liquid, then the operating plan may instruct that the gear case be replaced at a designated facility.

In the context of a locomotive or other vehicle, the operating plan may include instructions for controlling tractive and/or braking efforts of the vehicle. In particular, the operating plan may be partially based on the measurements of the operative condition of the machine. The instructions may be expressed as a function of time and/or distance of a trip along a route. In some embodiments, travel according to the instructions of the operating plan may cause the vehicle to reduce a stress on a component-of-interest of the machine than the component would typically sustain during normal operation. For example, the operating plan may instruct the vehicle to reduce horsepower delivered to an axle, to intermittently drive the axle, or to disable the axle altogether. The vehicle may be autonomously controlled according to the operating plan or the instructions of the operating plan may be presented to an operator of the vehicle so that the operator can manually control the vehicle according to the operating plan (also referred to herein as a "coaching mode" of the vehicle).

In some embodiments, the operating plan that is generated when it is determined that the machine is operating improperly is a "revised" operating plan that supersedes or replaces another operating plan. More specifically, due to the newly acquired measurements, the control system may determine that the currently-implemented operating plan should be modified and, as such, may generate a revised operating plan to replace the other.

Operating plans may be optimized to achieve designated goals or parameters. As used herein, the term "optimize" (and forms thereof) are not intended to require maximizing or minimizing a characteristic, parameter, or other object in all embodiments described herein. Instead, "optimize" and its forms may include increasing or decreasing (as appropriate) a characteristic, parameter, or other object toward a designated or desired amount while also satisfying other conditions. For example, optimized stress levels on a component may not be limited to a complete absence of stress or that the absolute minimum amount of stress. Rather, optimizing the stress level may mean that the stress is controlled, while also satisfying other conditions (e.g., speed limits, trip duration, arrival time). For example, the stress sustained by a component may be controlled so that the vehicle may arrive at its destination without the component being severely damaged.

The planning module 122 is configured to use at least one of vehicle data, route data (or a route database), part data, or trip data to generate the operating plan. The vehicle data may include information on the characteristics of the vehicle. For example, when the vehicle system is a rail vehicle, the vehicle data may include a number of rail cars, number of locomotives, information relating to an individual locomotive or a consist of locomotives (e.g., model or type of locomotive, weight, power description, performance of locomotive traction transmission, consumption of engine fuel as a function of output power (or fuel efficiency), cooling characteristics), load of a rail vehicle with effective drag coefficients, vehicle-handling rules (e.g., tractive effort ramp rates, maximum braking effort ramp rates), content of rail cars, lower and/or upper limits on power (throttle) settings, etc.

Route data may include information on the route, such as information relating to the geography or topography of various segments along the route (e.g., effective track grade and curvature), speed limits for designated segments of a route, maximum cumulative and/or instantaneous emissions for a designated segment of the route, locations of intersections (e.g., railroad crossings), locations of certain track features (e.g., crests, sags, curves, and super-elevations), locations of mileposts, and locations of grade changes, sidings, depot yards, and fuel stations. The route data, where appropriate, may be a function of distance or correspond to a designated distance of the route.

Part data may include, for example, historical data or proprietary data regarding the lifetime operability of a component. The data may include baseline data for a designated speed and/or load on the machine. Additional factors may be part of the baseline data. For example, if the lubricant has a designated quantity in the gear case, the part data may include data from identical components that operated with an approximately equal lubricant level. The data may include how long the component is capable of operating at a designated speed.

Trip data may include information relating to a designated mission or trip, such as start and end times of the trip, start and end locations, route data that pertains to the designated route (e.g., effective track grade and curvature as function of milepost, speed limits), upper cumulative and/or instantaneous limits on emissions for the trip, fuel consumption permitted for the trip, historical trip data (e.g., how much fuel was used in a previous trip along the designated route), desired trip time or duration, crew (user and/or operator) identification, crew shift expiration time, lower and/or upper limits on power (throttle) settings for designated segments, etc. In one embodiment, the planning module 122 includes a software application or system such as the Trip Optimizer™ system developed by General Electric Company.

Figure 2:
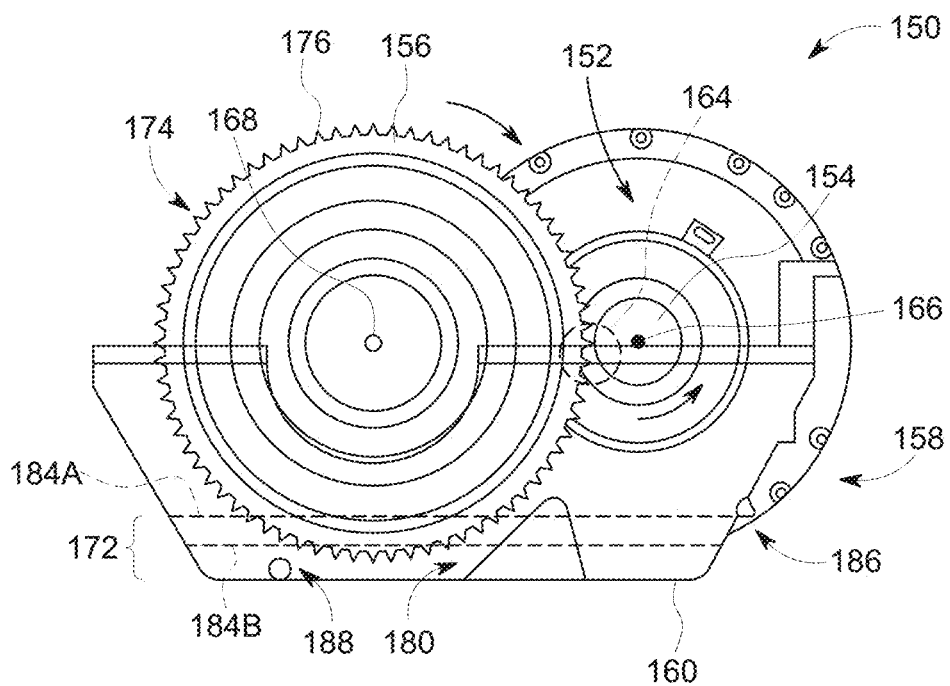
FIG. 2 is a side view of a drive train in accordance with an embodiment.
Figure 3:
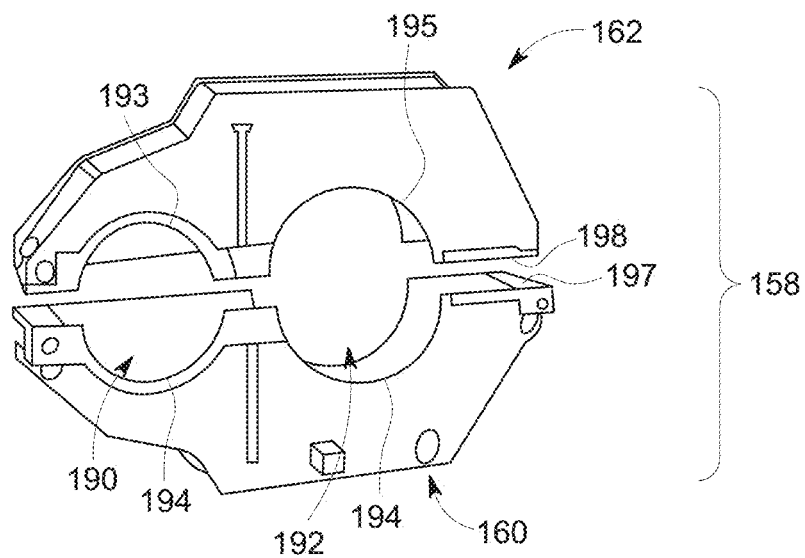
FIG. 3 is a partially exploded view of a gear case that may be used by the drive train of FIG. 2.

FIG. 2 is a side view of a drive train (or final drive) 150 in accordance with one embodiment. The drive train 150 includes a traction motor 152, a first (or pinion) gear 154, a second gear 156, and a base portion or shell 160 of a gear case 158. A top portion or shell 162 of the gear case 158 is shown in FIG. 3. As shown in FIG. 2, the first gear 154 and the second gear 156 engage each other at a gear mesh 164. During operation of the drive train 150 the traction motor 152 drives the first gear 154 by rotating an axle (not shown) coupled to the first gear 154 about an axis of rotation 166. The first gear 154 may be rotated, for example, in a counter-clockwise direction as viewed in FIG. 2. Due to the engagement at the gear mesh 164, the first gear 154 rotates the second gear 156 in a clockwise direction about an axis of rotation 168. The second gear 156 is coupled to an axle (not shown) that rotates with the second gear 156. The axle of the second gear 156 is coupled to wheels (not shown) that are rotated with the axle. The wheels engage a surface (e.g., rails or tracks) to move the machine.

The gear case 158 includes a reservoir 172 that is configured to hold a lubricant liquid 180 (e.g., oil). The gear case 158 has a fill or inlet port 186 and a drain or outlet port 188. The liquid 180 may be provided to the reservoir 172 through the fill port 186 and drained through the drain port 188.

As shown in FIG. 2, the second gear 156 has teeth 176 along an edge 174 of the second gear 156. When the liquid 180 is held within the gear case 158, the liquid 180 may have a fill level 184. FIG. 2 illustrates a first fill level 184A and a second fill level 184B. The second fill level 184B is lower than the first fill level 184A. In some embodiments, when the drive train 150 is operating properly, the quantity of the liquid 180 correlates to the first fill level 184A such that the edge 174 of the second gear 156 is sufficiently submerged within or bathed by the liquid 180. However, when the fill level is lowered to, for example, the fill level 184B, the edge 174 and teeth 176 may be insufficiently lubricated. Such circumstances may occur when the gear case 158 has a leak.

FIG. 3 is a partially exploded view of the gear case 158 and illustrates the base and top portions 160, 162 before the base and top portions 160, 162 are coupled to the drive train to surround the first and second gears 154, 156. As shown, the gear case 158 may include first and second gear-receiving openings 190, 192 that are sized to receive the first and second gears 154, 156 (FIG. 2), respectively. The gear-receiving openings 190, 192 may be defined by opening edges 193-196 and the base and top portions 160, 162 may engage each other along case edges 197, 198.

When the drive train 150 is fully constructed and operational, the opening edges 193-196 engage the portions of the drive train 150 along sealable interfaces. The case edges 197, 198 may also be coupled to each other along a sealable interface. During operation of the drive train 150, however, the interfaces may become damaged or worn such that the interfaces are no longer sufficiently sealed. For example, when the drive train 150 is part of a locomotive, the opening edges 193-196 or the case edges 197, 198 may become worn, damaged, or separated such that the liquid 180 is permitted to escape the reservoir 172. Accordingly, the amount of liquid 180 may reduce such that the fill level 184 (FIG. 2) lowers.

Embodiments described herein may be configured to detect that the amount of liquid 180 has reduced. In addition, due to the wear, damage, or separation of the base and top portions 160, 162, the gear case 158 (or portions thereof) may exhibit different vibratory characteristics. For example, a gear case that is sufficiently sealed with respect to the drive train 150 and has a sufficient fill level 184 may exhibit a first vibratory state when the drive train 150 is driven at a first speed. However, a gear case that is insufficiently sealed with respect to the drive train 150 and/or has an insufficient fill level 184 may exhibit a second vibratory state that is different than the first vibratory state when the drive train 150 is driven at the first speed. Embodiments described herein may be configured to detect and measure the different vibratory states. In certain embodiments, a wireless device, such as those described herein, is at least partially disposed within the reservoir 172 and/or directly attached to a portion of the gear case 158. For example, at least a portion of the wireless device 104 may be directly secured or affixed to a wall of the gear case 158, such as the wall that defines the reservoir 172. In some embodiments, the wireless device 104 is not physically electrically connected to other components of the machine, such as a computing system that controls operation of the machine.

In addition to liquid level and vibrations, embodiments may be configured to detect other characteristics. For example, other measurements may relate to a quality (e.g., degree of contamination) of the liquid. Contaminants may include water, metallic particles, and/or non-metallic particles. Furthermore, embodiments are not limited to the drive train or a gear case of the drive train. For example, measurements that may be obtained for a drive train may also be obtained for a turbo-charger, an air compressor, an engine, and the like. Other components of a machine may also be measured by wireless devices described herein.

Figure 4:
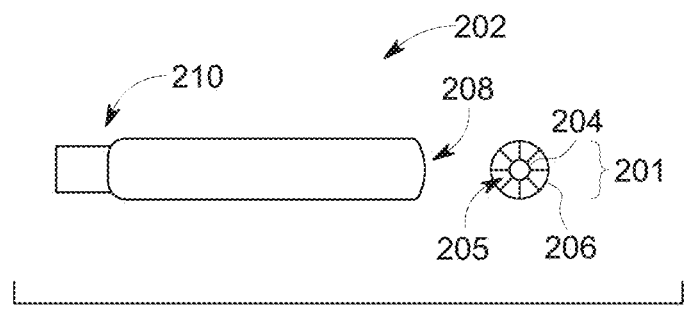
FIG. 4 is a side view of a capacitive-type sensor in accordance with an embodiment.
Figure 5:
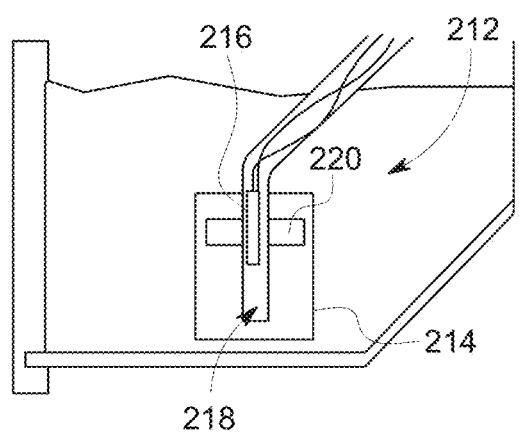
FIG. 5 is a schematic view of a magnetic float/reed switch sensor in accordance with an embodiment.
Figure 6:
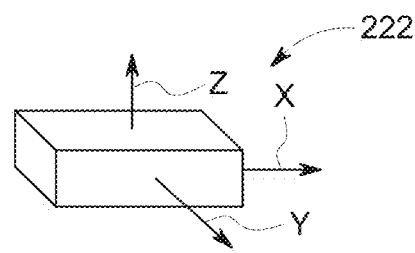
FIG. 6 is a schematic view of an accelerometer in accordance with an embodiment.

FIGS. 4-6 illustrate sensors 202, 212, 222, respectively. The sensors, which may also be referred to as transducers, may be a portion of the wireless devices described herein. Each of the sensors may be configured to measure (e.g., detect) a designated property or characteristic in the environment proximate to the sensor and provide a signal that is representative of the measured property or characteristic. The signal provided by the sensor may be the measurement.

Various types of measurements may be obtained by the sensors. Some non-limiting examples include a capacitance of a liquid, a temperature of a liquid and/or temperatures of certain parts of a machine, a fluid conduction of a liquid, a dielectric constant of a liquid, a dissipation factor of a liquid, an impedance of a liquid, a viscosity of a liquid, or vibrations of a mechanical element. A measurement may be directly obtained (e.g., temperature) by the sensor, or a designated measurement may be obtained after using information provided by the sensor to calculate the designated measurement. For example, the viscosity of the liquid may be calculated based on multiple level measurements obtained by a sensor.

Embodiments may include a single wireless device that is configured to measure and communicate only a single type of measurement (e.g., capacitance). However, in some embodiments, a single wireless device may be configured to measure and communicate multiple types of measurements (e.g., capacitance of the liquid, temperature of the liquid, temperature of the sensor, shock and/or vibration of the gear case, etc.). In such embodiments, the wireless device may have multiple sensors.

The sensor 202 is configured to measure a capacitance of a liquid, such as a lubricant in a tank (e.g., gear case). The sensor 202 is hereinafter referred to as a capacitive level probe 202. For reference, a cross-section 201 of the level probe 202 is also shown in FIG. 4. The level probe 202 extends lengthwise between a leading end 208 and a trailing end 210. The level probe 202 includes an inner or measurement electrode 204 and an outer or reference electrode 206. As shown, a space 205 exists between the inner and outer electrodes 204, 206. A capacitance of the material that exists within the space 205, such as a combination of a liquid and gas, may be measured by the level probe 202. In some embodiments, a wall of the tank that holds the liquid may be used as the reference electrode.

The level probe 202 is configured to be immersed into the liquid (e.g., oil) held by the tank. For example, the leading end 208 may be inserted into the liquid. As the leading end 208 is submerged, the liquid may flow into the space 205 thereby changing a ratio of liquid to gas within the space 205. As such, the measured capacitance changes as the level of the liquid within the space 205 changes. If the liquid is a lubricant, the measured value of capacitance decreases as an amount or level of the liquid decreases. As an amount or level of the liquid increases, the measured value of capacitance also increases.

The level probe 202 may also be configured to determine a quality of the liquid. More specifically, the level probe 202 may detect an amount or percentage of contaminations in the liquid based on capacitance measurements. For example, contaminant detection may be based on a dissipation factor of a dielectric of the liquid. In general, the dissipation factor is a function of an applied frequency, a liquid temperature, a composition of the liquid (e.g., the desired composition of the liquid), and contaminants. The dissipation factor may be substantially independent of the base capacitance or liquid level.

In some cases, movement of the machine may cause a displacement of the liquid which may introduce an error in the measurements. Accordingly, in some embodiments, the level probe 202 is only activated when the machine or component thereof is at rest (e.g., inactive). To this end, an accelerometer or other inertial type sensor may be part of or operably coupled to the wireless device that includes the level probe 202. The accelerometer may determine that the machine is in an inactive or stationary state such that measurements may be obtained by the level probe 202.

As shown in FIG. 5, the sensor 212 includes a body float 214 and a reed switch 216. The body float 214 includes a cavity 218 that is sized and shaped to receive the reed switch 216. The body float 214 is configured to float along the reed switch 216 (e.g., vertically) based on a level of the liquid in the reservoir. The body float 214 includes a permanent magnet 220, and the reed switch 216 includes a magnetically actuated switch or switches (not shown). As the body float 214 moves up and down, the permanent magnet 220 may activate or deactivate the switch (e.g., close or open a circuit, respectively, in the reed switch 216). The activated switch indicates that the body float 214 is at a designated level and, consequently, that the liquid is at a designated level.

As described above, one or more embodiments may also include a sensor that is an accelerometer. FIG. 6 illustrates one such sensor, which is referenced as an accelerometer 222. In some embodiments, the accelerometer 222 is a micro-electro-mechanical system (MEMS) tri-axis accelerometer. The accelerometer 222 may be used for a variety of functions. For example, the accelerometer 222 may be coupled to a mechanical element, such as a tank, and determine whether the mechanical element has remained stationary for a designated amount of time. In some embodiments, other measurements (e.g. liquid level) may be obtained only after it has been determined that the mechanical element has remained stationary for the designated amount of time.

Alternatively or additionally, the accelerometer 222 may be configured to detect vibratory states experienced by the mechanical element. For example, the accelerometer 222 may be configured to obtain numerous shock and vibrations measurements per second in each of x-, y-, and z-axes. For example, the accelerometer 222 may be able to log hundreds or thousands of data points per second in each of the x-, y-, and z-axes.

Figure 7:
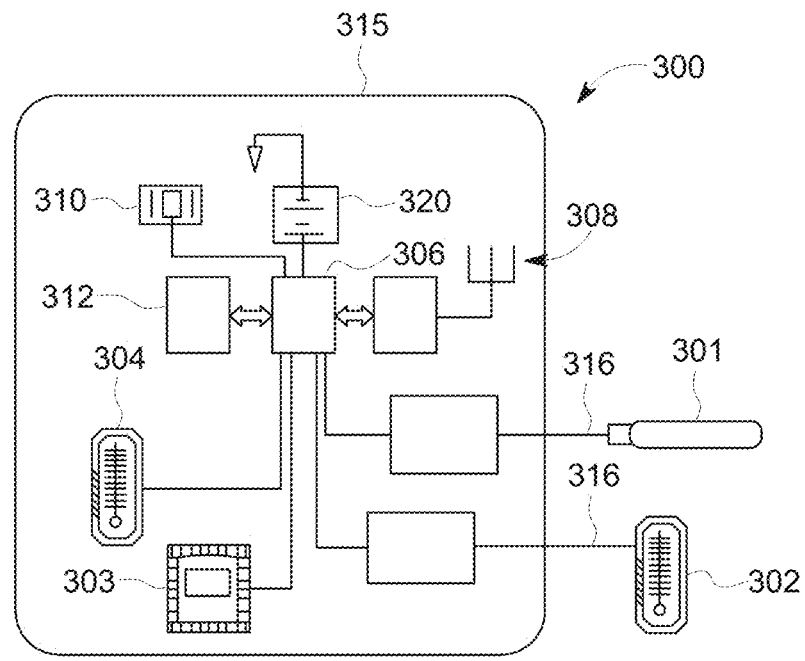
FIG. 7 is a schematic diagram of a wireless device formed in accordance with an embodiment.

FIG. 7 is a schematic diagram of a wireless device 300 formed in accordance with one embodiment. The wireless device 300 includes sensors 301-304, a processing unit 306 (e.g., microprocessor), a transmitter 308, an internal clock 310 (e.g., real-time clock crystal), and a memory 312 (e.g., non-volatile memory). The wireless device 300 has a device body 315, which may include a printed circuit board (PCB) or a die (e.g., semiconductor wafer) in some embodiments. In the illustrated embodiment, the device body 315 includes the sensors 303, 304, the processing unit 306, the transmitter 308, the internal clock 310, and the memory 312. In alternative embodiments, however, the wireless device 300 may have multiple bodies (e.g., multiple dies) that are coupled to each other and/or the components described herein may be separate from the device body 315. The sensors 301 and 302 may be operably coupled to the device body 315 through, for example, wires 316. In other embodiments, the sensors 301, 302 are wirelessly coupled to the device body 315.

The sensor 301 may be a level probe, such as the level probe 202 described with respect to FIG. 4. The sensor 301 is configured to be inserted into a liquid (e.g., lubricant) of a machine. The sensor 302 may be a thermometer that is configured to obtain a temperature of the liquid. The sensor 303 is an accelerometer, such as the accelerometer 222 (FIG. 6), and the sensor 304 is another thermometer that is configured to determine a temperature of the device body 315 of the wireless device 300. Each of the sensors 301-304 is communicatively coupled to the processing unit 306 and configured to communicate signals to the processing unit 306. The signals may be representative of a property or characteristic detected by the sensor.

The processing unit 306 may be configured to store or log data (e.g., data based on the signals obtained from the sensors) in the memory 312. In some embodiments, the processing unit 306 is configured to query the sensors 301-304 to request measurements from the sensors 301-304. The queries may occur at predetermined times or when a designated event occurs. For example, the queries may occur once an hour as determined by the internal clock 310 until, for example, the wireless device 300 is interrogated by a reader (not shown). At such an event, the processing unit 306 may query the sensors 301-304 for numerous data points. For example, the data points may be provided almost continuously after interrogation. The processing unit 306 may also receive data from the memory 312. The data received from the sensors 301-304 and/or the memory 312 may be transformed into data signals that are communicated by the transmitter 308 to the reader.

The wireless device 300 may be characterized as an active or semi-passive device. For example, the wireless device 300 may include a power source 320, such as a battery (e.g., lithium thionyl chloride battery) and/or kinetic energy harvesting device. The wireless device 300 may utilize the power source 320 to increase the transmission range of the transmitter 308. In such embodiments, the reader may be located tens or hundreds of meters away from the wireless device 300. In addition to the transmitter 308, the power source 320 may be used to supply power to other components of the wireless device 300, such as the sensors 301-304 or the processing unit 306.

Figure 8:
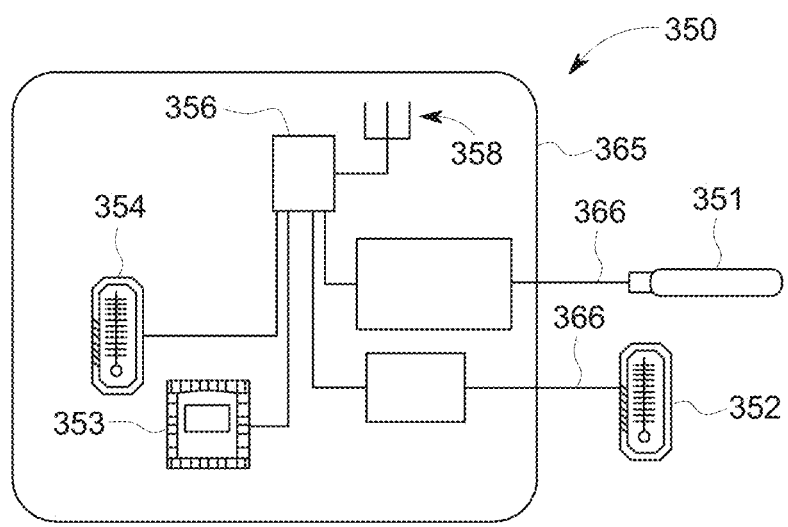
FIG. 8 is a schematic diagram of a wireless device formed in accordance with an embodiment.

FIG. 8 is a schematic diagram of a wireless device 350 formed in accordance with one embodiment. The wireless device 350 may be a passive device such that the wireless device 350 is powered by inductive or backscatter coupling with the reader (or some other non-internal power source). As shown, the wireless device 350 includes sensors 351-354, a processing unit 356, and a transmitter 358. The wireless device 300 has a device body 365 that includes, in the illustrated embodiment, the sensors 353, 354, the processing unit 356, and the transmitter 358. The device body 365 may be formed by integrated circuit technology. For example, the device body 365 may include one or more printed circuit boards (PCBs). The sensors 351 and 352 may be operably coupled to the device body 365 through, for example, wires 366. Similar to the wireless device 300 (FIG. 7), the sensors 351-354 may be a level probe, external thermometer, an accelerometer, and an internal thermometer, respectively.

In some embodiments, the processing unit 356 executes fewer calculations or conversions of the signals from the sensors 351-354 than the processing unit 306 (FIG. 7). For example, the processing unit 356 may be an ADC that converts the analog signals from the sensors 351-354 to digital signals. The digital signals may be the data signals that are then transmitted by the transmitter 358. In the illustrated embodiment, the processing unit 356 may only query the sensors 351-354 after being interrogated by a reader (not shown). More specifically, the interrogation signals from the reader may power the processing unit 356 to query the sensors 351-354 and transmit the data signals.

Figure 9:
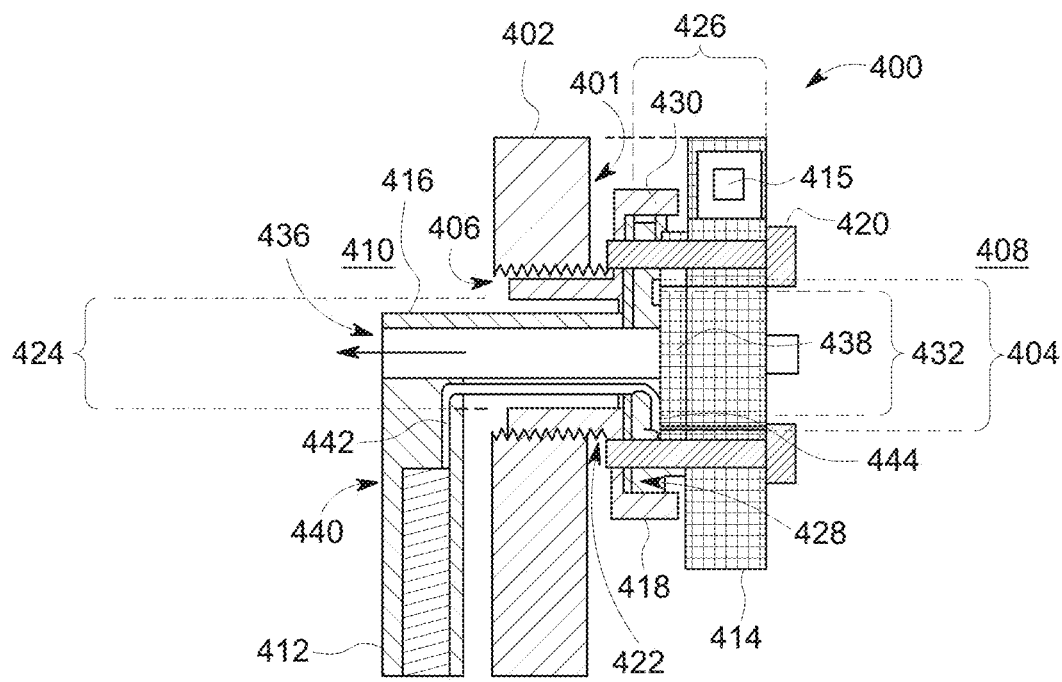
FIG. 9 is a cross-section of a portion of a wireless device utilizing the sensor of FIG. 4 in accordance with an embodiment.

FIG. 9 is a cross-section of a portion of a wireless device 400 attached to a wall 402 of a tank 401. The tank 401 may be part of a machine, such as a locomotive or other machines described herein. The tank 401 is configured to have a reservoir 410 for holding a liquid (not shown), such as a lubricant. The reservoir 410 is accessed through a fill port 404 of the wall 402 that is defined by interior threads 406 of the wall 402 as shown in FIG. 9. The fill port 404 provides access from an exterior 408 of the tank 401 to the reservoir 410.

As shown, the wireless device 400 includes a sensor 412, a device body 414, and an intermediate cable portion 416 that joins the sensor 412 and the device body 414. The wireless device 400 also includes a coupling component 418 that is configured to be secured to the device body 414 through, for example, fasteners 420 and attached to the wall 402. In the illustrated embodiment, the coupling component 418 includes threads 422 that complement and are configured to rotatably engage the threads 406 of the wall 402. However, in other embodiments, different methods of attaching the coupling component 418 to the tank may be used, such as latches, interference fits (e.g., plugs), and/or adhesives.

To assemble the wireless device 400, the coupling component 418 may be rotatably engaged to the wall 402. The sensor 412 and the cable portion 416 may be inserted through an opening 424 of the coupling component 418 and the fill port 404. As shown, the coupling component 418 has a mating face 428 that faces in a direction away from the wall 402. The cable portion 416 has a mating end 426 that is located in the exterior 408 of the tank 401 and may be pressed toward the mating face 428 with a gasket 430 located therebetween. The device body 414 has a cable opening 432 that receives an end of the cable portion 416. The device body 414 may be secured to the cable portion 416 and the coupling component 418 using the fasteners 420. As shown, the cable portion 416 includes a fill channel 436 that permits access to the reservoir 410. During operation, the fill channel 436 may be closed with a plug 438 at the mating end 426 of the cable portion 416.

The sensor 412 may be similar or identical to the level probe 202 described with respect to FIG. 4. For example, a trailing end 440 of the sensor 412 is shown in FIG. 9. The trailing end 440 is coupled to wires 442 that communicatively couple the sensor 412 to the device body 414. In other embodiments, the sensor 462 may be similar or identical to the sensor 212 (FIG. 5). The cable portion 416 is configured to surround and protect the wires 442 from the surrounding environment. As shown, the wires 442 terminate at a contact ring 444 along the device body 414. The sensor 412 is configured to transmit signals to the device body 414 through the wires 442 and the contact ring 444. The device body 414 is configured to process and transmit data signals that represent measurements obtained by the sensor 412. The device body 414 may include an integrated circuit unit 415. Although not shown, the integrated circuit unit 415 of the device body 414 may have a processing unit, power source, internal clock, additional sensors, and/or a transmitter, such as those described above. In some embodiments, the integrated circuit component 415 is formed as an RFID unit.

Figure 10:
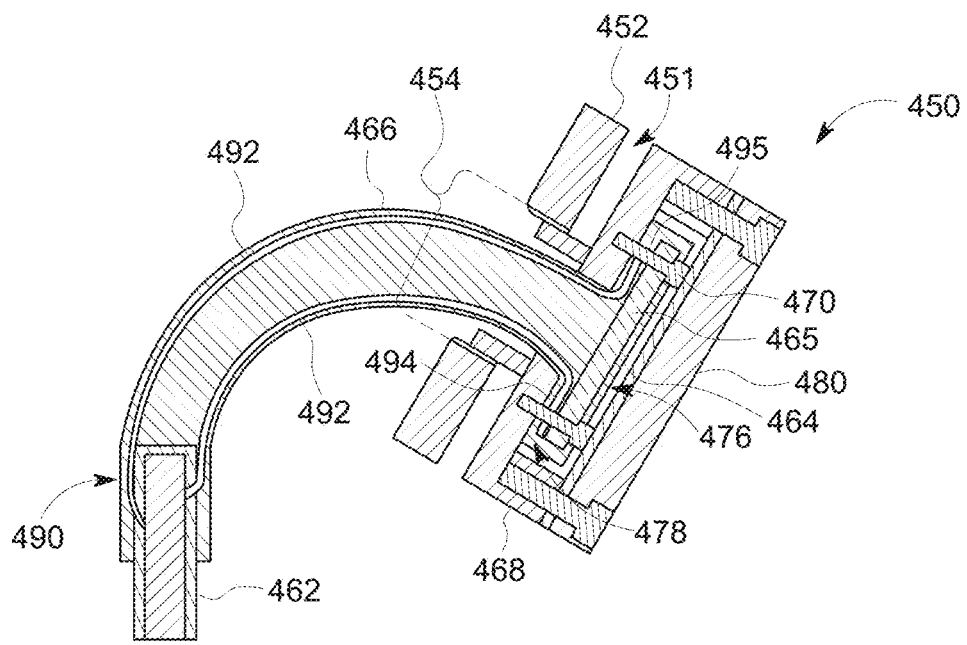
FIG. 10 is a cross-section of a portion of a wireless device utilizing the sensor of FIG. 4 in accordance with an embodiment.

FIG. 10 is a cross-section of a portion of a wireless device 450, which is also configured to be coupled to a wall 452 of a tank 451. The wireless device 450 may include similar features as the wireless device 400 (FIG. 9). For example, the wireless device 450 includes a sensor 462, a device body 464, and an intermediate cable portion 466 that joins the sensor 462 and the device body 464. The wireless device 450 also includes a coupling component 468 that is configured to be secured directly to the device body 464 and the cable portion 466 through fasteners 470. In the illustrated embodiment, the coupling component 468 is rotatably engaged to the wall 452 in a similar manner as the coupling component 418 (FIG. 9). However, other methods of attaching the coupling component 468 to the wall may be used.

To assemble the wireless device 450, the coupling component 468 may be rotatably engaged to the wall 452. The sensor 462 and the cable portion 466 may be inserted through the coupling component 416 and a fill port 454 of the wall 452. The device body 464 may be encased within a mating end 476 of the cable portion 466. As shown, the coupling component 468 has a mating face 478 that faces in a direction away from the wall 452. Accordingly, the cable portion 466 and the device body 464 may be secured to the coupling component 468 using the fasteners 470. A cover body 480 may then be positioned over the cable portion 466 to hold the device body 464 between the cover body 480 and the coupling component 468. Unlike the wireless device 400, the cable portion 466 does not include a fill channel that permits access to the reservoir.

The sensor 462 may be similar or identical to the level probe 202 described with respect to FIG. 4. For example, a trailing end 490 of the sensor 462 is shown in FIG. 10. The trailing end 490 is coupled to wires 492 that communicatively couple the sensor 462 to the device body 464. In other embodiments, the sensor 462 may be similar or identical to the sensor 212 (FIG. 5). As shown, the wires 492 terminate at contacts 494, 495 that are coupled to the device body 464. The device body 464 may include an integrated circuit component 465, which, in the illustrated embodiment, is a RFID unit. The sensor 462 is configured to transmit signals to the integrated circuit component 465 through the wires 492. Like the integrated circuit component 415, the integrated circuit component 465 is configured to process and transmit data signals that represent measurements obtained by the sensor 462. The integrated circuit component 465 may include a processing unit, power source, internal clock, additional sensors, and/or a transmitter, such as those described above.

FIG. 11 is a cross-section of a portion of a wireless device 500. The wireless device 500 may be similar to the wireless device 400 (FIG. 9) and the wireless device 450 (FIG. 10). However, as shown in FIG. 11, the wireless device 500 utilizes a sensor 502 that may be similar to or identical to the sensor 212 (FIG. 5). The wireless device 500 also includes a coupling component 504 that is configured to attach to a wall 506 of a tank 508, which is a gear case in the illustrated embodiment. The coupling component 504 may be similar to the coupling components described above. For example, the coupling component 504 may rotatably engage the wall 506.

Also shown, the wireless device 500 includes a device body 530 that is operably coupled to the sensor 502 through a base support 510 and an intermediate beam 512. The base support 510 is disposed within an opening 514 of the coupling component 504. The beam 512 extends between and joins the sensor 502 and the base support 510. The beam 512 may be fabricated from, for example, stainless steel and is configured to provide a passageway 516 for wires 518 that communicatively couple the device body 530 and the sensor 502.

The base support 510 includes a mating face 520 that faces away from the tank 508. The mating face 520 has contacts 524, 525 thereon. The contact 524 may be a contact pad, and the contact 525 may be a ring contact that extends around the contact pad. A device body 530 is configured to be rotatably engaged to the coupling component 504. The device body 530 includes a mounting surface 532 that faces the mating face 520 and has corresponding contacts that are configured to engage the contacts 524, 525. More specifically, when the device body 530 is rotated to engage the coupling component 504, the mounting surface 532 of the device body 530 may advance toward the mating face 520 so that the contacts of the device body 530 press against and engage the contacts 524, 525.

Accordingly, the device body 530 may be communicatively coupled to the sensor 502. Similar to the device bodies described above, the device body 530 may include an integrated circuit component 515 having a processing unit and a transmitter (not shown). Optionally, the integrated circuit component 515 may also include a memory, an internal clock, and one or more other sensors. The integrated circuit component 515 may transform the signals from the sensor 502 (or memory or other sensors) into data signals. The data signals may then be transmitted to a reader (not shown). In some embodiments, the integrated circuit component 515 is formed as an RFID unit.

FIG. 12 is a cross-section and FIG. 13 is a front view, respectively, of a portion of a wireless device 550. The wireless device 550 may include a sensor (not shown) and a device body 552 that are communicatively coupled through wires 554. The sensor may be similar to the sensor 202 (FIG. 4) or the sensor 212 (FIG. 5). The device body 552 is secured to a faceplate 556 that is coupled to an exterior surface of a tank 560 (FIG. 13). FIGS. 12 and 13 illustrate an embodiment in which no electrical contacts are required along the device body 552 to electrically join the sensor. Instead, wires 554 (FIG. 12) from the sensor may extend through potting 562 that mechanically couples the sensor to the tank 560. Like the wireless device 400 (FIG. 9), the wireless device 550 may permit access to a fill port 566 through a plug 568. Although not shown, the device body 552 may include an integrated circuit component, such as those described above, that processes data signals and transmits data signals. The integrated circuit component may be an RFID unit that is directly coupled to one of the wires 554.

Figure 14:
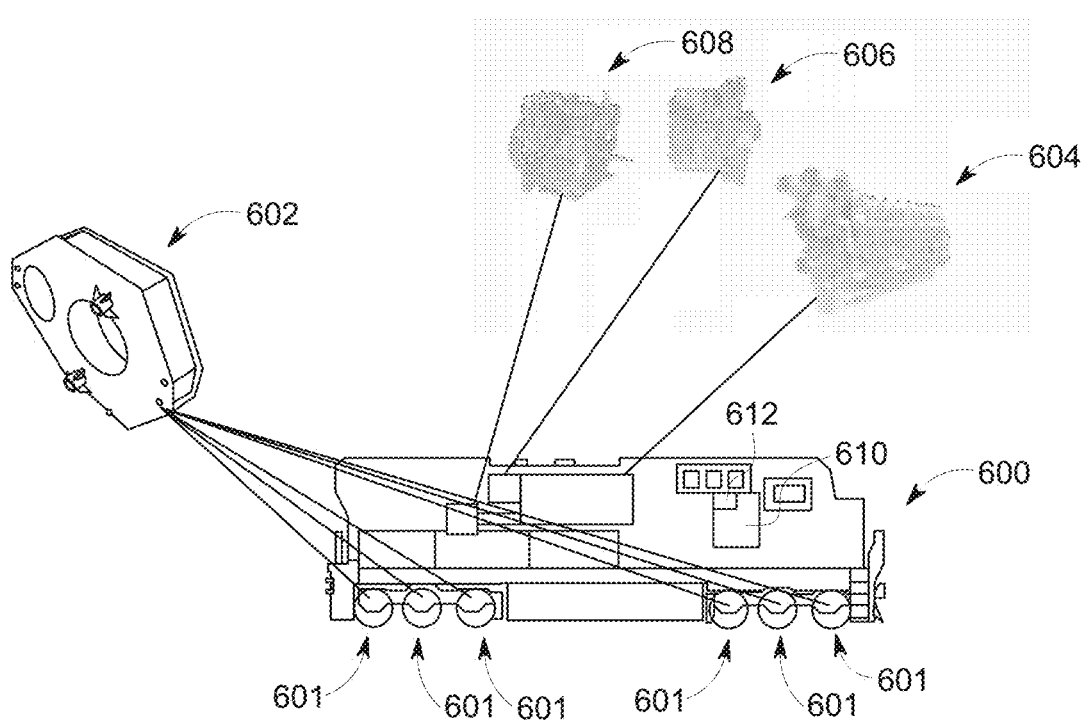
FIG. 14 is a schematic view of a locomotive and illustrates a plurality of components of the locomotive in accordance with an embodiment.

FIG. 14 is a schematic view of a locomotive 600 and illustrates a plurality of components of the locomotive 600 that may include one or more wireless devices, such as the wireless devices described herein. For example, the locomotive 600 may include a plurality of drive trains 601 that each has a gear case 602. The locomotive 600 may also include an engine 604, a turbo-charger 606 operably coupled to the engine 604, and an air compressor 608. Each of the components may have one or more of the wireless devices described herein operably coupled thereto. For example, the gear cases 602 and the engine 604 may have at least one of the wireless devices 202, 212, 222, 400, 450, 500, or 550 described above. In particular, each of the gear cases 602 and the engine 604 may have a reservoir that includes a liquid lubricant. The turbo-charger 606 and the air compressor 608 may use, for example, an accelerometer similar to the wireless device 222.

As shown, the locomotive 600 may also include an on-board control system 610. The control system 610 can control the tractive efforts and/or braking efforts of the locomotive 600 and, optionally, other locomotives that are directly or indirectly coupled to the locomotive 600. Operations of the control system 610 may be based on inputs received from an operator of the locomotive and/or remote inputs from, for example, a control tower, a dispatch facility, or the like. In addition, the control system 610 may receive inputs from various components of the locomotive 600. In some cases, the inputs may be data signals received through wireless communication. For example, the wireless devices of the gear cases 602, the engine 604, the turbo-charger 606, and the air compressor 608 may be configured to wirelessly communicate data signals to the control system 610. The control system 610 may include a reader 612 for receiving the wireless data signals. The control system 610 may also include a signal-processing module and a planning module that are similar to the signal-processing and planning modules 120, 122 described in FIG. 1. The planning module may generate operating plans for the locomotive 600 based on the inputs received.

Figure 15:
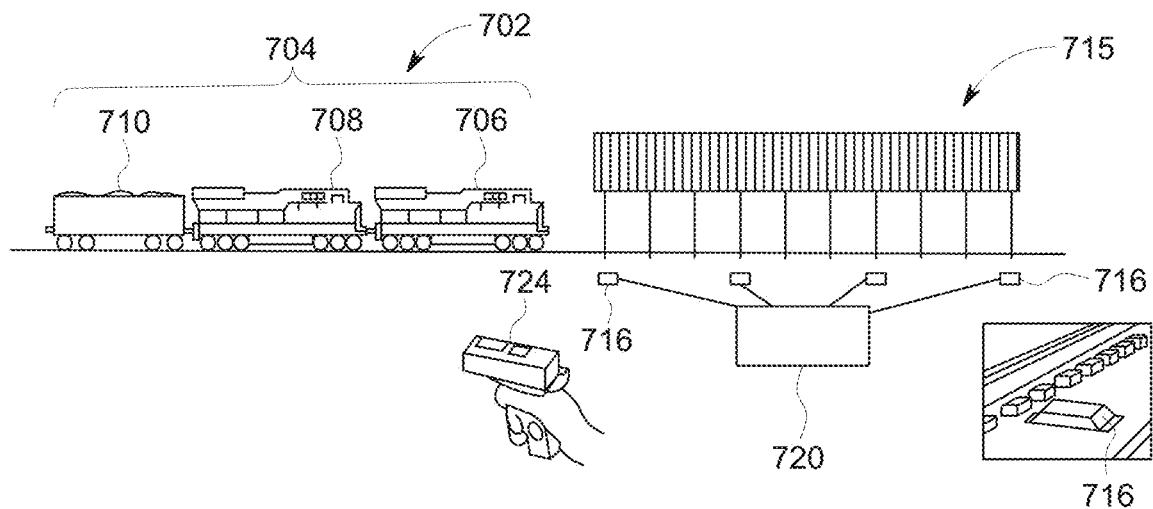
FIG. 15 illustrates a system in accordance with an embodiment for obtaining data signals from one or more wireless devices.
Figure 16:
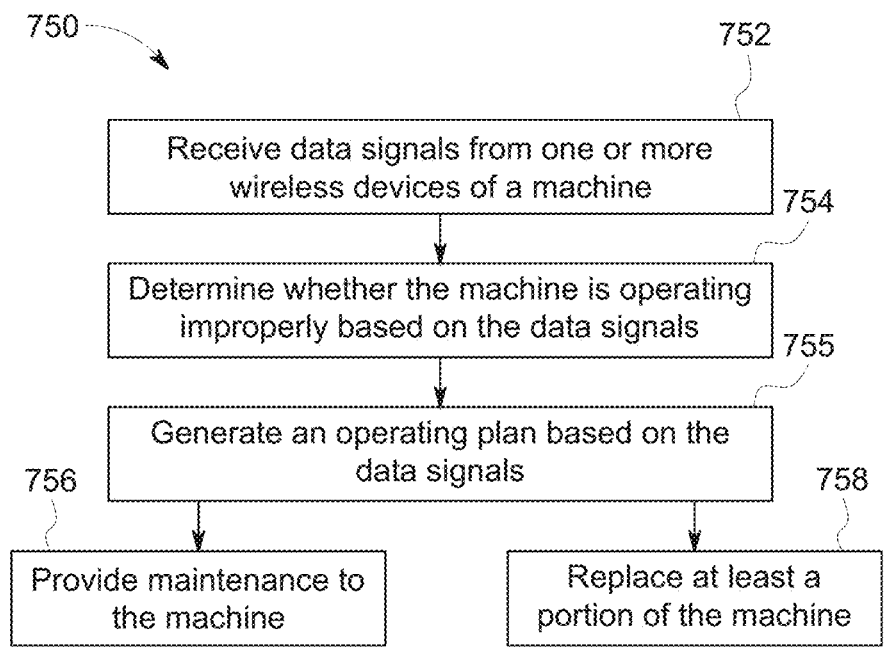
FIG. 16 is a flowchart illustrating a method in accordance with an embodiment.

FIG. 15 illustrates a system 700 in accordance with one embodiment for obtaining data signals from one or more wireless devices. FIG. 16 illustrates a flowchart of a method 750 that may be executed or performed by the system 700. In some embodiments, the locomotive 600 (FIG. 14) may also execute or perform the method 750. The system 700 and the method 750 may employ structures or examples of various embodiments discussed herein. In some embodiments, certain steps of the method 750 may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Likewise, the system 700 is not required to include each and every feature of each and every embodiment described herein.

With respect to FIG. 15, the system 700 includes a vehicle system 702 (e.g., train) including a locomotive consist 704. The locomotive consist 704 may include at least one locomotive that is linked (directly or indirectly) to one or more rail cars. For example, FIG. 15 shows the locomotive consist 704 including first and second locomotives 706, 708 and a rail car 710. In other embodiments, the vehicle system 702 may include more rail cars 710. Each of the locomotives 706 and 708 may include a plurality of components that are each monitored by one or more wireless devices. For example, each of the locomotives 706, 708 may include an engine, a turbo-charger, an air compressor, and a plurality of gear cases, such as those described herein.

As shown in FIG. 15, the vehicle system 702 is approaching a designated reading location 715. The reading location 715 is a maintenance facility in the illustrated embodiment. However, the reading location 715 may be a variety of other locations that are capable of receiving wireless data signals from the locomotives. For example, the reading location 715 may be a depot, fuel station, wayside location, rail yard entry point or exit point, designated sections of the track(s), and the like. The reading location 715 includes a plurality of readers 716. Each of the readers 716 is communicatively coupled (e.g., wirelessly or through communication wires) to a control system 720. Alternatively or additionally, a handheld reader 724 may be carried by an individual and used to receive the data signals. The reader 724 may also communicate data signals with the control system 720.

The control system 720 may include a signal-processing module and a planning module, such as the signal-processing and planning modules 120, 122 described in FIG. 1. For example, the control system 720 may generate operating plans that include instructions for operating the vehicle system 702 and other similar vehicle systems.

The method 750 may include receiving (at 752) data signals from one or more of the wireless devices of a machine. In the illustrated embodiment, the machine is the vehicle system 702 or one of the locomotives 704, 706. However, embodiments described herein are not necessarily limited to locomotives. The machine may have one or components with moving mechanical elements or parts. For example, the machine may have a drive train, engine, air compressor, and/or turbo-charger. The data signals may be representative of a measurement of an operative condition of the component. By way of example the measurement may be at least one of a vibration measurement, a capacitance of a liquid, a temperature of a liquid, a fluid conduction of a liquid, a dielectric constant of a liquid, an impedance of a liquid, or a viscosity of a liquid. In particular embodiments, the measurement is representative of a vibratory state of a gear case or of a liquid condition of a lubricant held in the gear case.

The receiving operation (at 752) may include receiving the data signals at one or more fixed readers having stationary positions. For example, the readers 716 may have fixed positions with respect to tracks 730. The readers 716 may be located at designated distance from the tracks 730 so that the readers 716 are capable of receiving the data signals. The receiving operation (at 752) may also include receiving the data signals through one or more movable readers, such as the handheld reader 724.

In an alternative embodiment, as described above, the receiving operation (at 752) may occur with an on-board control system, such as the control system 610 (FIG. 14).

The method 750 also included determining (at 754), based on the data signals, whether the component of the machine is operating improperly. For example, the control system 720 may analyze the data signals and, optionally, other inputs to determine whether the component is operating sufficiently. If the component is operating improperly, the method 750 also includes generating (at 755) an operating plan that is based on the data signals. The operating plan may be a new (or revised) operating plan that is configured to replace a currently-implemented operating plan. The method 750 may also include at least one of providing maintenance (at 756) to the component or replacing (at 758) an element of the component.

In an embodiment, a system (e.g., a monitoring system) is provided that includes a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system may also include a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

In one example, the transmitter is configured to be energized by the reader when the reader interrogates the transmitter.

In one example, the system includes a power source that is configured to supply power to the transmitter for transmitting the data signals. The power source may include, for example, a battery and/or energy harvesting device.

In one example, the sensor is configured to be at least partially submerged in the liquid.

In one example, the measurement is at least one of a capacitance of the liquid, a temperature of the liquid, a fluid conduction of the liquid, a dielectric constant of the liquid, an impedance of the liquid, or a viscosity of the liquid.

In one example, the device body is configured to be affixed to a wall of the machine in which the wall at least partially defines the reservoir.

In one example, the sensor and the device body collectively form a first wireless device. The system may also include a second wireless device that is configured to obtain and wirelessly communicate second data signals that are representative of a measurement of a different reservoir.

In one example, the sensor is configured to be disposed in a gear case of a locomotive, the gear case having the reservoir.

In one example, the transmitter is included in a radio-frequency identification (RFID) element.

In one example, the sensor, the processing unit, and the transmitter collectively form a first wireless device. The system may also include a second wireless device that is configured to obtain and wirelessly transmit data signals that are representative of a measurement of a different reservoir. The system may include a signal-processing module. The signal-processing module may be configured to determine, based on the data signals, whether the machine is operating improperly by comparing the data signals of the first wireless device to the data signals of the second wireless device.

In one example, the data signals are configured to be transmitted to a handheld reader. In another example, the data signals are configured to be transmitted to a fixed reader located along a railway track. In yet another example, the data signals are configured to be transmitted to an on-board reader located on a locomotive.

In one example, the sensor includes a multi-conductor capacitive sensor configured to detect a capacitance of a fluid. The fluid may function as a dielectric, wherein a level of the fluid affects the capacitance detected. In another example, the sensor includes a body float and a position transducer configured to detect a position of the body float. The position transducer may include, for example, a reed switch.

In an embodiment, a system (e.g., a monitoring system) is provided that includes a sensor that is configured to be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that is configured to wirelessly communicate the first data signals to a remote reader.

In one example, the system includes a power source configured to supply power to the transmitter for transmitting the data signals.

In one example, the system includes a memory. The memory is configured to log a plurality of the measurements obtained at different times. The transmitter is configured to transmit data signals that include the measurements.

In one example, the sensor, the processing unit, and the transmitter collectively form a first wireless device. The system may include a second wireless device configured to obtain and wirelessly transmit data signals that are based on a measurement of a different drive train.

In one example, the device body includes a radio-frequency identification (RFID) unit. The RFID unit may have the processing unit and the transmitter.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train. The method also includes, responsive to determining that the drive train is operating improperly, generating signals to schedule at least one of maintenance of the drive train or replacement of an element of the drive train.

In one example, the measurement is representative of vibratory state of a gear case or a liquid condition of a lubricant held in the gear case.

In one example, the measurement is at least one of a vibration measurement of a gear case, a capacitance of a lubricant stored by the gear case, a temperature of the lubricant, a fluid conduction of the lubricant, a dielectric constant of the lubricant, impedance of the lubricant, or a viscosity of the lubricant.

In one example, the data signals are received from a plurality of wireless devices. The data signals are based on a common type of measurement.

In one example, the data signals are received at a handheld reader.

In one example, the machine is a locomotive and the data signals are received at a fixed reader located along a railway track.

In one example, the machine is a locomotive and the data signals are received at a reader located on-board the locomotive.

In one example, the method also includes operating the machine according to a first operating plan and generating a second operating plan that is based on the operative condition.

In an embodiment, a system (e.g., a monitoring system) includes a signal-processing module that is configured to receive data signals from a wireless device of a machine having a drive train. The data signals are based on a measurement of an operative condition of the drive train. The signal-processing module is configured to determine, based on the data signals, whether the drive train is operating improperly. Optionally, the system also includes a planning module that is configured to generate an operating plan that is based on the operative condition.

In another embodiment, a system (e.g., wireless liquid monitoring system) comprises a sensor, a processing unit, and a transmitter. The sensor is configured to be disposed within a reservoir of a machine having moving parts that are lubricated by a liquid in the reservoir. The sensor is configured to obtain a measurement of the liquid that is representative of at least one of a quantity or quality of the liquid in the reservoir. The processing unit is operably coupled to the sensor and configured to generate first data signals representative of the measurement of the liquid. The transmitter is operably coupled to the processing unit and configured to wirelessly communicate the first data signals to a remote reader.

In another embodiment of the system, alternatively or additionally, the transmitter is an RFID unit, which may be, for example, similar to an RFID tag, chip, card, or label.

In another embodiment of the system, alternatively or additionally, the system is configured to be disposed in the machine (and when installed is actually disposed in the machine), which comprises a vehicle or other powered system comprising the reservoir, the moving parts, and one or more computers or other controller-based units (e.g., a vehicle controller) other than the processing unit. The system may not be physically electrically connected (e.g., not connected by wires or other conductors) to any of the one or more computers or other controller-based units in the machine. Thus, the first data signals may only wirelessly transmitted from the system to the reader or elsewhere, and are not transmitted via wire/cables or other physical electrical connections.

In another embodiment of the system, alternatively or additionally, the processing unit and transmitter are co-located proximate to one another (e.g., at least partially integrated onto a common circuit board, positioned within a common box/housing that is positioned within the machine—that is, the common box/housing is not coextensive with the outer body/structure of the machine, but is located within the outer body/structure—and/or some or all of the components of the processing unit and transmitter are located within 10 cm of each other, within 5 cm of each other, etc., for example), and/or at least portions of the processing unit and transmitter are directly connected to a wall of the reservoir (e.g., a wall that bears a pressure of and/or contacts the liquid in the reservoir) and/or to a structure immediately connected to such a wall (e.g., support structure of the reservoir, gear case, or the like).

In another embodiment of the system, alternatively or additionally, the transmitter is configured to wirelessly communicate the first data signals to the remote reader that comprises: a remote reader located within the machine (e.g., if the machine is a vehicle, the remote reader is located with the vehicle); a remote reader located on a wayside of a route of the machine, the machine comprising a vehicle; a portable (handheld, or otherwise able to be carried by a human operator) remote reader.

Additional embodiments are disclosed that relate to sensing methods and systems. The sensors, such as resonant sensors, may include inductor-capacitor-resistor (LCR) sensors that can be used as sensors or transducers for sensing fluids. Provided herein are sensors having a part that is a resonant structure that exhibits resolvable changes in the presence of a fluid and various components or contaminants in the fluid.

In one embodiment, the sensor may include an inductor-capacitor-resistor (LCR) resonator circuit with a resonance frequency response provided by the resonant impedance (Z) of this circuit. The sensors as provided herein may be capable of sensing properties of interest in the presence of variable noise sources and operating over the variable temperature conditions to provide stable sensor performance over time. Disclosed herein are sensors that include inductor-capacitor-resistor (LCR) resonators, which may function as a sensor or as a transducer. The resonant impedance spectrum of the sensor may be measured either via inductive coupling between pick up coil and sensor or directly by connecting to a sensor reader. The electrical response of the sensor may be translated into the resonant impedance changes of the sensor.

Non-limiting examples of signal changes of an individual sensor may include combined and simultaneous resonant impedance change, inductance change, resistance change, and capacitance change (referred to herein as electrical characteristics). Suitable sensors and systems disclosed herein may enhance the ability to measure changes in a fluid, such as engine oil or fuel, by contacting it with the sensor between the electrodes that constitute a resonant circuit of the sensor. The resonant circuit of the sensor may be an electrical resonant circuit. Other resonant circuits may include a mechanical resonator, where a change of viscosity and/or density of the fluid cause a response of the mechanical resonators.

Suitable mechanical resonators may include tuning fork resonators, thickness shear mode resonators, quartz crystal microbalance resonators, surface acoustic wave resonators, bulk acoustic wave resonators, and others. Unlike these and other mechanical resonators, the electrical resonators may be not predictably affected by the changes change of viscosity and/or density of the fluid. Instead, they may be predictably affected by the changes in the complex permittivity of the fluid. Electrical resonators may be very complicated in their design, for example marginal oscillators require complicated multi-component circuits.

The degradation of at least some oils and lubricants may generate molecules and/or other moieties that may be relatively more polar than the oil and lubricant from which they were formed. The base oil or lubricant may include long chain hydrocarbon molecules that are weakly polar. Thus, the presence of polar contaminants may increase of one or more parts of the oil's complex permittivity.

The degradation of at least some oils and lubricants may generate molecules and/or other moieties that may be relatively low molecular weight and may be in the form of volatiles or gases. For example, an insulating oil of an oil-fitted transformer is employed to insulate and suppress corona and arcing and to serve as a coolant. However, the insulating oil gradually deteriorates under the impact of electrical, thermal and environmental stresses during the life of the transformer. Different types of gases are generated in the insulating oil depending on the deterioration processes. Examples of these gases include hydrogen, carbon monoxide, carbon dioxide, methane, ethane, ethylene, and acetylene. For example, thermal decomposition of mineral oil produces hydrogen and methane. Thermal decomposition of cellulose and other solid insulation materials produces carbon monoxide, carbon dioxide, and water vapor. Such gases are detected and monitored in real time using multivariable sensors as described in more detail below. For this application the sensor is coated with a sensing material that is responsive to one or more gases of interest. When the sensor is in operational contact with the oil, dissolved gases in oil also interact with the sensor and produce a predictable multivariable sensor response. The operational contact may be achieved by direct immersion of the sensor into oil when the sensing material is wetted by oil or through a gas permeable membrane that may allow dissolved gases in oil to diffuse through the membrane to the sensing material while the oil is not wetting the sensing material.

According to one example, the resonant transducers operate as re-configurable resonant structures and operate at multiple frequencies for monitoring of a status of fluids (and, further, for example, the health of equipment in contact with such fluids) and to probe more accurately dielectric properties of any samples in the presence of uncontrolled ambient environmental noise contributions. Monitoring the health of fluids involves a determination of composition or a determination of contamination of such fluid.

Non-limiting examples of interferents and ambient environmental noise contributions include temperature and presence of interferences in a sample. The term "interference" includes any undesired environmental parameter that adversely affects the accuracy and precision of measurements of the sensor. The term "interferent" refers to a material or environmental condition that potentially may produce an erroneous response by the sensor. Filters (physical, chemical, and/or electronic) may be employed, based on the application specific parameters, to reduce, eliminate, or account for the presence and/or concentration of such interferents.

Figure 17:
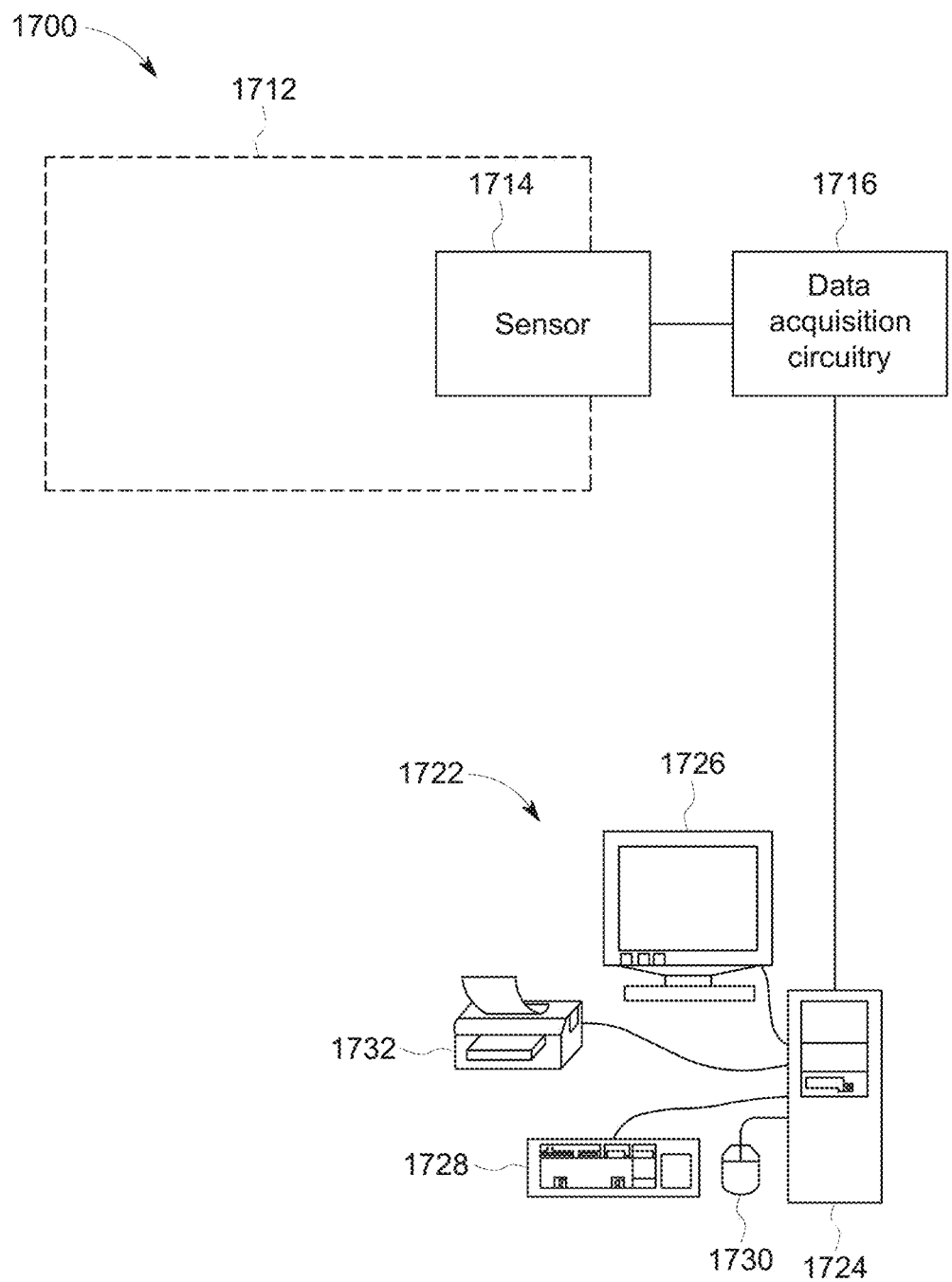
FIG. 17 is a block diagram of a system for assessing fluid according to an embodiment of the disclosure.

With reference to FIG. 17, a sensing system 1700 is shown that may be useful for assessing a fluid in contact therewith. The system 1700 may represent one embodiment of the system 100 shown in FIG. 1. For purposes of illustration, a representative fluid may be engine oil. The system may include a fluid reservoir 1712 for a fluid and a sensor 1714. The sensor 1714 may represent one embodiment of the sensor 108 shown in FIG. 1. Alternatively, the sensor may be set in a flow path of the fluid. The sensor may be a resonant sensor that is disposed in, or on, the reservoir, or may be coupled to in-line connectors in fluid communication with the fluid reservoir that define a flow path. In one embodiment, the sensor may provide continuous monitoring of the fluid within the reservoir or flow path.

Suitable fluids may include hydrocarbon fuels and lubricants. Suitable lubricants may include engine oil, gear oil, hydraulic fluid, lubricating oils, synthetic based lubricants, lubricating fluids, greases, silicones, and the like. Suitable fuels may include gasoline, diesel fuel, jet fuel or kerosene, bio-fuels, petrodiesel-biodiesel fuel blends, natural gas (liquid or compressed), and fuel oils. Still other fluids may be insulating oils in transformers, solvents, or mixtures of solvents. Still other fluids may be included with correspondingly appropriate sensor parameters, such as water, air, engine exhaust, biologic fluids, and organic and/or vegetable oils. The fluid may be a liquid, or may in in a gaseous phase. Further contemplated are multiphase compositions. The fluids may be disposed in and/or used in connection with the operation of another system, such as the machine 102 shown in FIG. 1.

Non-limiting examples of various fluid components include unintended leaks from proximate systems (e.g., radiator fluid into engine oil, or water condensation in diesel fuel or transformer oil) and/or from fluid-transport devices (e.g., valves, flanges, pipes, tubes). Other detectable fluid components may include degradation products of the fluid caused due to elevated temperature of operation, or due to contact with oxidants (air, others). System operation may introduce fluid components such as dirt, salt, soot or carbon, wear metal particles, wear products, and others. In some environments, fouling due to bacteria or the like may be the fluid component. And in all instances, indirect measurement may be useful, such as a pH rise that indicates the presence of an acidic component. Other detectable fluid components may include external contaminants of the fluid.

The sensor may detect characteristics of the fluid via a resonant impedance spectral response. One or more of the LCR resonators may measure the resonant impedance spectral response. As opposed to simple impedance measurements, the disclosed embodiments probe the sample with at least one resonant electrical circuit. The resonant impedance spectrum of the sensor in proximity to the sample (the sensor in operational contact with the fluid) varies based on sample composition and/or components and/or temperature. The measured resonant impedance values Z' (which may be the real part of resonant impedance, Zre) and Z" (which may be the imaginary part of resonant impedance, Zim) reflect the response of the fluid (for example, the portion of the fluid in proximity to the sensor) to a stimulus of the electric field of the resonant electrical circuit.

The electrical field may be applied by the sensor via electrodes. The electrodes may be in direct or indirect electrical contact with the sample. For example, a sensor may be a combination of a sensing region and associated circuits. The sensing region may be either bare or coated with a protective dielectric layer or a sensing layer. In each of the disclosed cases, the sensing region may be considered to be in operational contact with a fluid. In such embodiments, the tuning circuits may not contact the fluid directly. One example of indirect electrical contact with the sample may be when a sensing electrode structure is coated with a dielectric protective coating and when the electric field that may be generated between the electrodes interacts with the fluid after penetrating through the dielectric protective coating. A suitable dielectric protective coating may be conformally applied to the electrode.

Suitable sensors may include single use or multi-use sensors. A suitable multi-use resonant sensor may be a re-usable sensor that may be used during the lifetime of a system in which it may be incorporated into. In one embodiment, the resonant sensor may be a single use sensor that may be used during all or part of a reaction or process. For example, the resonant sensor may include one or more pairs of electrodes and one or more tuning elements, e.g., a resistor, a capacitor, an inductor, a resonator, impedance transformer, or combinations of two or more thereof to form an inductor-capacitor-resistor (LCR) resonant circuit operated at one or more resonant frequencies. In certain embodiments, different resonant circuits of a plurality of resonant circuits of a resonant sensor may be configured to resonate at different frequencies. Different frequencies may be selected to be across the dispersion profile of the measured fluid composition. The dispersion profile may be a dependence of the dielectric properties of the fluid composition on the probing frequency. Various components of the fluid have different dispersion profiles. When measured at multiple resonance frequencies, concentrations of different components of the fluid may be determined.

Figure 18:
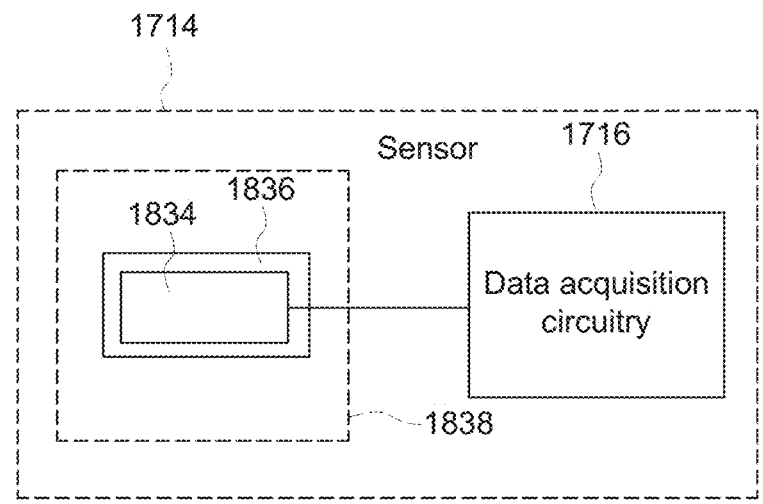
FIG. 18 is a schematic view of a resonant sensor according to an embodiment of the disclosure.

Data from the resonant sensor may be acquired via data acquisition circuitry 1716, which may be associated with the sensor or which may be associated with a control system, such as a controller or workstation 1722 including data processing circuitry, where additional processing and analysis may be performed. The controller or workstation may include one or more wireless or wired components, and may also communicate with the other components of the system. Suitable communication models include wireless or wired. At least one suitable wireless model includes radio frequency devices, such as RFID wireless communications. Other wireless communication modalities may be used based on application specific parameters. For example, where there may be EMF interference certain modalities may work where others may not. The data acquisition circuitry can be disposed within the fluid reservoir as shown in FIG. 18. Other suitable locations may include disposition being within the workstation. Further, the workstation can be replaced with a control system of the whole process where the resonant sensor and its data acquisition circuitry may be connected to the control system of process.

During operation, the monitoring process may couple to, among other things, operation of an internal combustion engine, an oil-filled transformer, a chemical reaction process, a biological reaction process, purification and/or separation process, a catalytic process, a general combustion process, production of raw oil, production of raw gas, material extraction, material transport, and other industrial processes. The data acquisition circuitry may be in the form of a sensor reader, which may be configured to communicate wirelessly or wired with the fluid reservoir and/or the workstation. For example, the sensor reader may be a battery-operated device and/or may be powered using energy available from the main control system or by using harvesting of energy from ambient sources (light, vibration, heat, or electromagnetic energy).

Additionally, the data acquisition circuitry may receive data from one or more resonant sensors 1714 (e.g., multiple sensors formed in an array or multiple sensors positioned at different locations in or around the fluid reservoir). The data may be stored in short or long term memory storage devices, such as archiving communication systems, which may be located within or remote from the system and/or reconstructed and displayed for an operator, such as at the operator workstation. Non-limiting examples of positioning and installations of sensors and sensor systems of the present techniques include fuel or fluid reservoirs, associated piping components, connectors, flow-through components, and any other relevant process components.

In addition to displaying the data, the operator workstation may control the above-described operations and functions of the system. The operator workstation may include one or more processor-based components, such as general purpose or application specific computers 1724. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation or by associated components of the system. Alternatively, the programs and routines may be stored on a computer accessible storage and/or memory remote from the operator workstation but accessible by network and/or communication interfaces present on the computer. The computer may also comprise various input/output (I/O) interfaces, as well as various network or communication interfaces. The various I/O interfaces may allow communication with user interface devices, such as a display 1726, keyboard 1728, electronic mouse 1730, and printer 1732, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

The sensor may include a plurality of resonant circuits that may be configured to probe the fluid in the fluid reservoir with a plurality of frequencies. The fluid reservoir may be a reservoir bound by the engineered fluid-impermeable walls or by naturally formed fluid-impermeable walls or by the distance of the electromagnetic energy emitted from the sensor region to probe the fluid. Further, the different frequencies may be used to probe a fluid sample at different depths. In certain embodiments, an integrated circuit memory chip may be galvanically coupled to the resonant sensor. The integrated circuit memory chip may contain different types of information. Non-limiting examples of such information in the memory of the integrated circuit chip include calibration coefficients for the sensor, sensor lot number, production date, end-user information. In another embodiment, the resonant sensor may comprise an interdigital structure that has a fluid-sensing region.

In certain embodiments, when an integrated circuit memory chip may be galvanically coupled to the resonant sensor, readings of the sensor response may be performed with a sensor reader that contains circuitry operable to read the analog portion of the sensor. The analog portion of the sensor may include resonant impedance. The digital portion of the sensor may include information from the integrated circuit memory chip.

FIG. 18 illustrates a non-limiting example of a design of the resonant sensor. A sensing electrode structure 1834 of the sensor may be connected to the tuning circuits and the data acquisition circuitry. The sensing electrode structure 1834 can be bare and in direct contact with the fluid. Alternatively, the sensing electrode structure can be coated with a protective or sensing coating 1836. The sensing electrode structure, without or with the protective or sensing coating, forms a sensing region 1838. The coating may be applied conformably, and may be a dielectric material. The sensing electrode structure, without or with the protective coating that forms the sensing region, may operationally contact a fluid. The fluid contains the analyte or contaminant(s). The sensing electrode structure may be either without (bare) or with a protective coating. A bare sensing electrode structure may generate an electric field between the electrodes that interacts directly with the fluid. A dielectric protective coated sensing electrode structure may generate an electric field that is between the electrodes that interacts with the fluid after penetrating through the dielectric protective coating. In one embodiment, the coating may be applied onto electrodes to form a conformal protective layer having the same thickness over all electrode surfaces and between electrodes on the substrate. Where a coating has been applied onto electrodes to form a protective layer, it may have a generally constant or variable final thickness over the substrate and sensor electrodes on the substrate. In another embodiment, a substrate simultaneously serves as a protective layer when the electrodes are separated from the fluid by the substrate. In this scenario, a substrate has electrodes on one side that do not directly contact the fluid, and the other side of the substrate does not have electrodes that face the fluid. Detection of the fluid may be performed when the electric field from the electrodes penetrates the substrate and into the fluid. Suitable examples of such substrate materials may include ceramic, aluminum oxide, zirconium oxide, and others.

Figure 19:
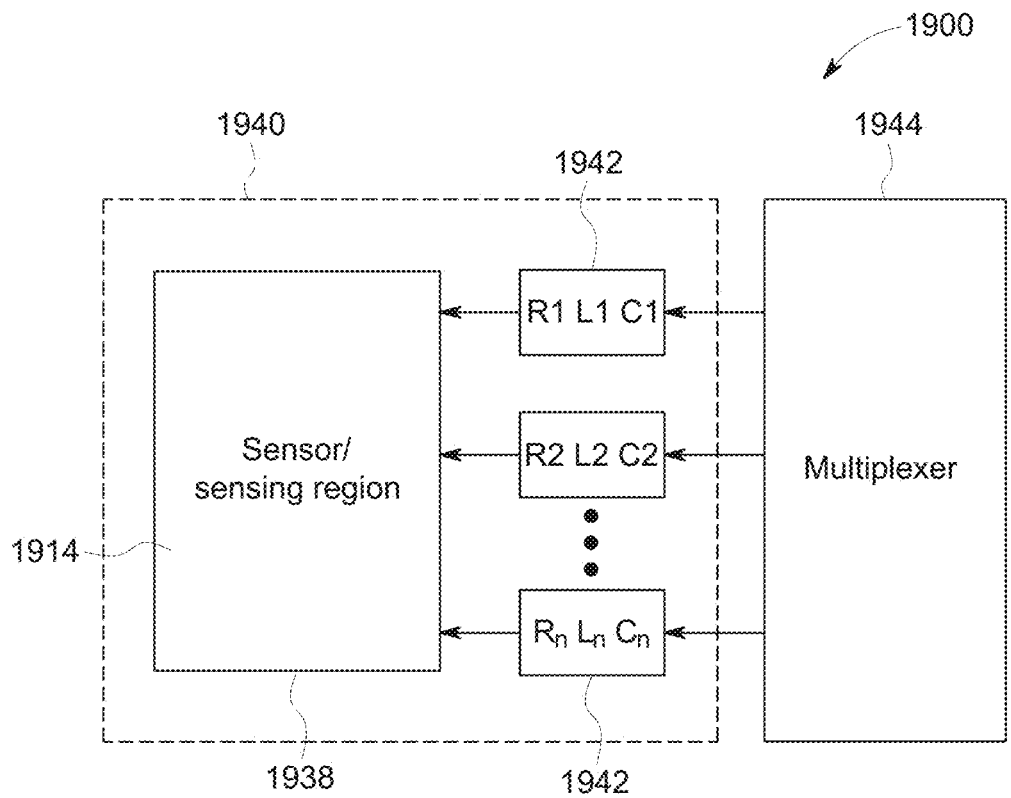
FIG. 19 is a schematic view of a portion of one example sensor system employing a sensor assembly configured for sensing of a fluid using a plurality of frequencies, in accordance with embodiments of the present disclosure.

FIG. 19 illustrates a portion of a resonant sensor system 1900 having a single sensing region 1938, and employed in a sensor assembly 1940 useful to probe a fluid sample using a plurality of frequencies. The sensing region may be disposed on a substrate and may include a suitable sensing material. In some embodiments, the substrate of the sensor may be a dielectric substrate. In some embodiments, the sensor assembly may include a plurality of tuning elements 1942. The plurality of tuning elements may be operatively coupled to the single sensing region to define a plurality of resonant circuits. The tuning elements along with the single sensing region may define a plurality of resonant circuits. Each resonant circuit of the plurality of resonant circuits may include one or more tuning elements of the plurality of tuning elements. Not shown is a semi-permeable film, semi-permeable membrane, or semi-permeable inorganic barrier (collectively a "selective barrier") that allows (or prevents) selective analytes or contaminants through the selective barrier and into the sensing region.

Suitable interdigital electrode structures for probing a fluid sample include two- and four-electrode structures. Suitable materials for electrodes include stainless steel, platinum, gold, noble metals, and others. Suitable materials of a substrate and/or a dielectric protective layer may include silicon dioxide, silicon nitride, parylene, silicone, fluorinated polymers, alumina, ceramics, and others. Suitable examples of sensing layers include semiconducting materials, metal oxides, nanocomposites, polymers, or the like. Suitable electrodes may be formed using metal etching, screen-printing, ink-jet-printing, and mask-based metal deposition techniques. The thickness of fabricated electrodes on the substrates may be in a range of from about 10 nanometers to about 1000 micrometers. The materials for the interdigital electrode structures, substrate, dielectric protective layer, sensing layer, and electrode formation methods may be selected based at least in part on the application specific parameters.

As shown in the illustrated embodiment, the plurality of tuning elements may be disposed external to the sensor. However, in one embodiment, the tuning elements may be disposed on the substrate of the sensor. In another embodiment, some of the plurality of tuning elements may be external to the sensor substrate, while other tuning elements may be disposed on the substrate. The tuning elements may comprise a resistor, a capacitor, an inductor, a resonator, impedance transformer, or combinations thereof.

The sensor assembly 1940 may include a controller that has a multiplexer 1944. The multiplexer may facilitate electronic switching between the tuning elements. The multiplexer may select one or more signals associated with the probing frequencies and forward the selected signal to an output device or a reader, such as the reader 106. In one embodiment, the multiplexer may selectively send signals to an output device or a reader. The multiplexer may send a plurality of signals simultaneously to a sensor reader. The multiplexer may facilitate electronic switching between the sensing regions.

During operation, each resonant circuit may resonate at a defined frequency. At least one resonant circuit may resonate at a frequency that may be different from the resonating frequency of the other resonant circuits. By way of example, if the sensing region includes a pair of electrodes, the tuning elements may be a resistor, a capacitor, and an inductor to form an inductor-capacitor-resistor (LCR) resonant circuit. The tuning elements may be electrically coupled to the sensing region. In one embodiment, the tuning elements may be in parallel connection to the sensing region. In certain embodiments, the different resonant circuits of the plurality of resonant circuits may be configured to resonate at different frequencies. The different resonant circuits may be configured to probe the fluid sample with a plurality of resonant frequencies. The different resonant frequencies may be used to probe a fluid sample over the frequency range of spectral dispersions of fluid components. The spectral dispersions of fluid components may include spectral dispersions of external contaminants of the fluid and aging of the fluid. The spectral dispersions that may be monitored with the sensors of the present disclosure may be over a frequency range of from about 0.1 Hz to about 100 GHz and include alpha, beta, gamma, delta, and other types of spectral dispersions as constrained by application specific parameters.

Figure 20:
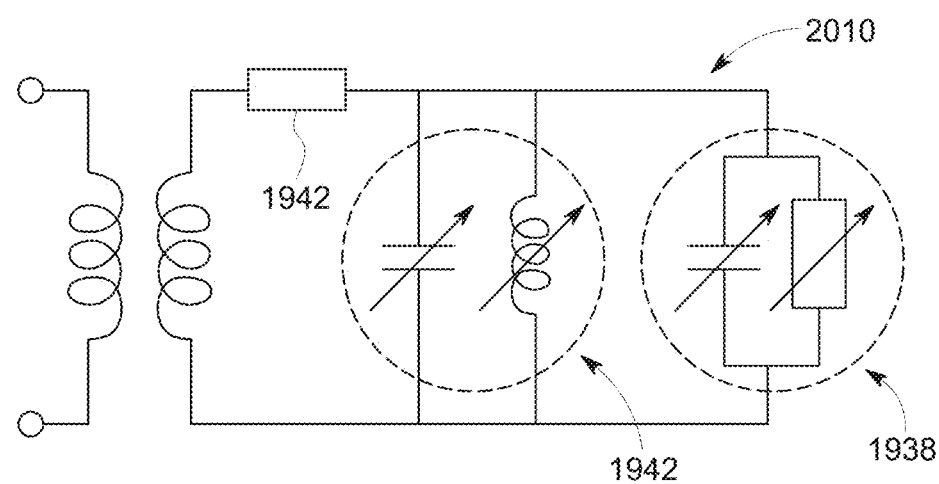
FIG. 20 is one example of an equivalent circuit of the resonant sensor according to an embodiment of the disclosure.

FIG. 20 illustrates another sensor circuit 2010. The sensing region 1938 (shown with variable resistor and capacitor) is combined with tuning components 1942 (shown with variable inductance and capacitance). To realize sensor response at different frequency range, additional circuit elements may be utilized to tune the frequency range. Therefore, a sensor can be operating at multiple frequency ranges by using a defined or selected combination of extra circuit components—such as inductors, capacitors, and impedance transformers. These components may be connected in parallel or in series, as needed, to the sensor to vary the operating frequency range. The controller may control the impedance transformer ratio to affect the sensitivity. A sensor's frequency response and its magnitude may be based at least in part on the overall input resonant impedance changes due to the sensor's response to the cell's status, its behavior, and the like. Thus, the sensor's sensitivity may be controlled through the dynamic tunability of the transformer ratio. Tuning the response of each channel may be achieved, for example, by using one or more inductors. In one embodiment, wireless readout from the electrodes may provide an improvement in response selectivity and sensitivity. In one embodiment, transformer based coupling may reject parasitic LCR components from instrumentation (analyzer, cables, amongst others). The LCR resonator in FIG. 20 has a relatively simple design as compared to other resonators, for example as compared to marginal oscillators that require complicated multi-component circuits for their operation that include a current feedback amplifier and other components.

Figure 21:
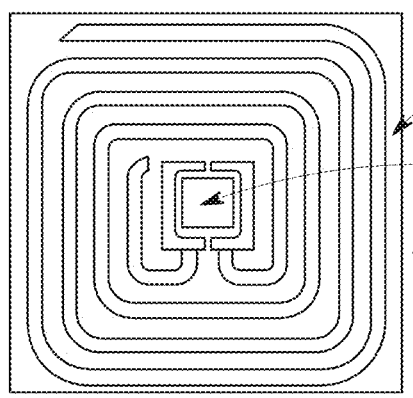
FIG. 21 is one example of an adapted radio frequency identification (RFID) tag for resonant sensing in which the sensing region constitutes a whole or a portion of the resonant antenna according to an embodiment of the disclosure.
Figure 22:
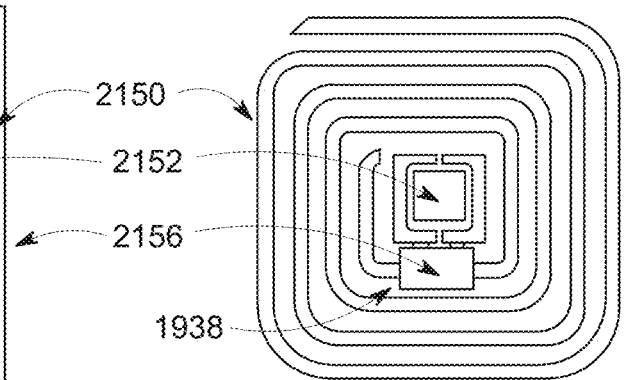
FIG. 22 is one example of an adapted RFID tag for resonant sensing in which the sensing region is in galvanic contact with the antenna and memory chip according to an embodiment of the disclosure.

As noted herein, a suitable wireless sensor may be radio-frequency identification (RFID) sensor where a passive RFID tag may be adapted to perform a sensing function. With reference to FIGS. 21 and 22, an embodiment is shown in which the resonant sensor may be an adapted RFID tag. In FIG. 21 a resonant antenna 2150 and memory chip 2152 may be coated with a protective material or sensing material 2156. The sensing material may be a sensing region of the RFID tag. In FIG. 22, the sensing region 1938 (that can optionally include the protective or sensing material) may be attached across an antenna. In both cases (FIGS. 21 and 22), the electrical response of the sensing region may be translated into changes in the resonant impedance response of the sensor. An RFID sensor having a memory chip may operate with a frequency determined at least in part by the operating frequency used the memory chip. That is, some operating frequencies (of the sensor and the chip) may interfere with each other and may be less desirable to have disruptive harmonics or destructive waveforms. And, the sensor can have a circular, square, cylindrical, rectangular, or other appropriately-shaped sensing region and/or antenna.

The resonant frequency of an antenna circuit may be set to a higher frequency than a resonant frequency of the sensor circuit. The frequency differential may be in a range of from, for example, as much as about 4 times to about 1000 times higher. In one embodiment, the sensor circuit may have a resonant frequency that may respond to a determined sensed environmental condition. The two resonant circuits may be connected so that when alternating current (AC) energy is received by the antenna resonant circuit, it may apply direct current energy to the sensor resonant circuit. The AC energy may be supplied through the use of a diode and a capacitor, and the AC energy may be transmitted to the sensor resonant circuit through an LC tank circuit through either a tap within the L of the LC tank circuit or a tap within the C of the LC tank circuit. Further, the two resonant circuits may be coupled such that voltage from the sensor resonant circuit may change the impedance of the antenna resonant circuit. The modulation of the impedance of the antenna circuit may be accomplished through the use of a transistor, for example a FET (field-effect transistor).

The RFID sensor's memory chip may be optional. The RFID sensor without a memory chip can be a resonant LCR sensor and can operate at different frequency ranges from a kilohertz to several gigahertz. That is, the memory chip's absence may widen the available frequency range.

Suitable sensing materials and sensing films as disclosed herein may include materials deposited onto the sensor to perform a function of predictably and reproducibly affecting the resonant impedance sensor response upon interaction with the environment. For example, a conducting polymer, such as polyaniline, changes its conductivity upon exposure to solutions of different pH. That is, the resonant impedance sensor response changes as a function of pH when such a conducting polymer film is deposited onto the RFID sensor surface. Thus, such an RFID sensor works as a pH sensor.

As one example of gaseous fluid detection, when such a polyaniline film is deposited onto the RFID sensor for detection in gas phase, the complex resonant impedance sensor response also changes upon exposure to basic (for example, $NH_3$) or acidic (for example, HCl) gases. Suitable sensor films include polymer, organic, inorganic, biological, composite, and nano-composite films that change their electrical and or dielectric property based on the environment in which they may be placed. Other examples of sensor films may be a sulfonated polymer such as commercially available Nafion, an adhesive polymer such as silicone adhesive, an inorganic film such as sol-gel film, a composite film such as carbon black-polyisobutylene film, a nano-composite film such as carbon nanotube-Nafion film, gold nanoparticle-polymer film, metal nanoparticle-polymer film, zeolites, metal-organic frameworks, cage compounds, clathrates, inclusion compounds, semiconducting materials, metal oxides, electrospun polymer nanofibers, electrospun inorganic nanofibers, electrospun composite nanofibers, and other sensor materials selected based on application specific parameters. To reduce or prevent the material in the sensor film from leaking into the liquid environment, the sensor materials may be attached to the sensor surface using standard techniques, such as covalent bonding, electrostatic bonding and other techniques. Some sensing materials may require a certain temperature for efficient operation. A non-limiting range of operating temperatures of the sensing materials and associated sensors onto which the sensing materials are deposited is between −260 degrees Celsius and 1600 degrees Celsius.

In one embodiment, the system may measure a resonant impedance $2(f)$ (represented by Eq. (1)) of the sensor.

$$(f)=Z_{re}(f)+jZ_{im}(f) \qquad \text{Eq. (1)}$$

where $Z_{re}(f)$ may be the real part of the resonant impedance and $Z_{im}(f)$ may be an imaginary part of the resonant impedance. In one embodiment, the resonant impedance spectral response of the sensor may be a multivariable response as more than one frequency may be utilized to measure sensor response across the resonance of the sensor. In some embodiments, the resonant impedance response of the sensor may be a multivariable response because more than one frequency may be utilized to measure sensor response outside the resonance peak of the sensor. In some embodiments, the sensor response may be measured at multiple frequencies across the resonance of the sensor. For example, if the sensor resonates at about 1 MHz, the measured frequencies and associated sensor responses may be measured from about 0.25 MHz to about 2 MHz. This multivariable response may be analyzed by multivariate analysis. The multivariable response of the sensor includes the sensor's full resonant impedance spectral response and/or several individually measured properties, such as but not limited to $F_p$, $Z_p$, $F_z$, $F_1$, $F_2$, $Z_1$, and $Z_2$. As used herein, the term "resonant impedance spectral response" may be referred to as "resonant impedance spectra".

Figure 23:
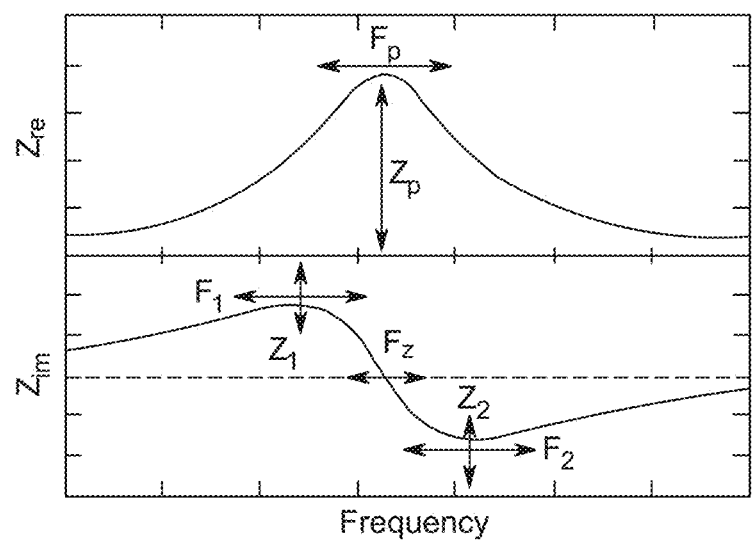
FIG. 23 is a graph of measured resonant impedance parameters of an embodiment of the resonant sensor, in accordance with embodiments of the present technique.

FIG. 23 depicts a graph of measured resonant impedance parameters of an embodiment of the resonant sensor, in accordance with embodiments of the present technique. These and other measured properties may be "spectral parameters." The measured properties may be also called "signals" or "output signals". These properties include the frequency of the maximum of the real part of the resonant impedance ($F_p$, resonance peak position), magnitude of the real part of the resonant impedance ($Z_p$, peak height), zero-reactance frequency ($F_z$, frequency at which the imaginary portion of resonant impedance may be zero), resonant frequency of the imaginary part of the resonant impedance ($F_1$), and anti-resonant frequency of the imaginary part of the resonant impedance ($F_2$), signal magnitude ($Z_1$) at the resonant frequency of the imaginary part of the resonant impedance ($F_1$), and signal magnitude ($Z_2$) at the anti-resonant frequency of the imaginary part of the resonant impedance ($F_2$). Other parameters may be measured using the entire resonant impedance spectra, for example, quality factor of resonance, phase angle, and magnitude of resonant impedance. The measured "output signals" may be from a resonant sensor or from a non-resonant sensor.

Figure 24:
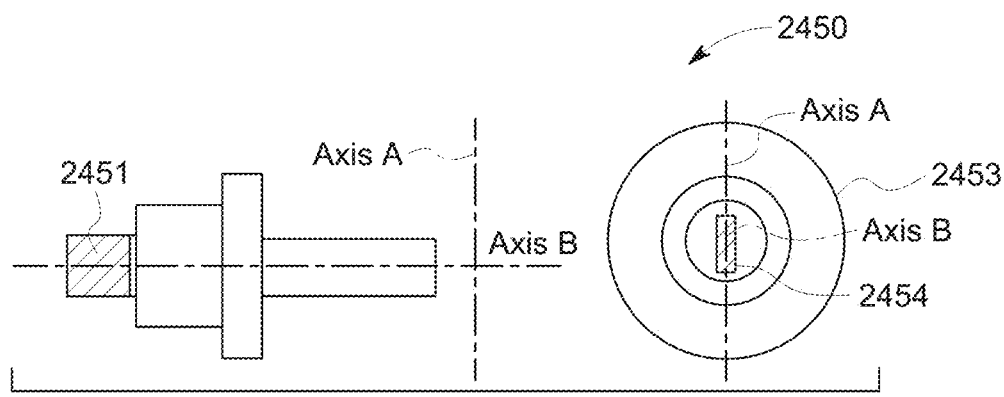
FIG. 24 is one example of a resonant sensor in which the sensing region is arranged parallel to the sensor axis insertion into the measured fluid, and therefore, perpendicular to the insertion port of the sensor according to an embodiment of the disclosure.
Figure 25:
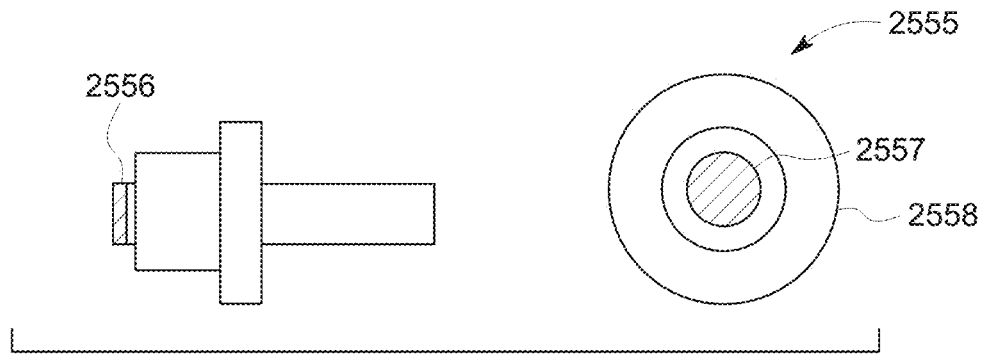
FIG. 25 is one example of a resonant sensor in which the sensing region is arranged perpendicular to the sensor axis insertion into the measured fluid, and therefore, parallel to the insertion port of the sensor according to an embodiment of the disclosure.

For measurements of fluid properties in fluid reservoirs, sensors with their sensing regions can be designed to fit standard ports or specially made ports in the reservoirs. Suitable design examples are depicted in FIG. 24 and FIG. 25. One example is provided of a resonant sensor 2450 with an aligned sensing region 2451. The sensing region defines a first Axis A, which is perpendicular to a transverse axis labeled Axis B. An insertion port structure 2453 defines an insertion aperture 2454 that is elongated along Axis A. The sensing region, then, is arranged parallel to the port's elongated aperture, translation along Axis B allows for sensor region insertion into the port and to contact a measured fluid. One example of another resonant sensor 2555 in which the sensing region 2556 is not constrained by its shape relative to an aperture 2557 defined by a port structure 2558 is depicted in FIG. 25. Alignment pins, not shown, may be used to align the sensor, and the sensing region, relative to the port aperture, as may be desired.

Figure 26:
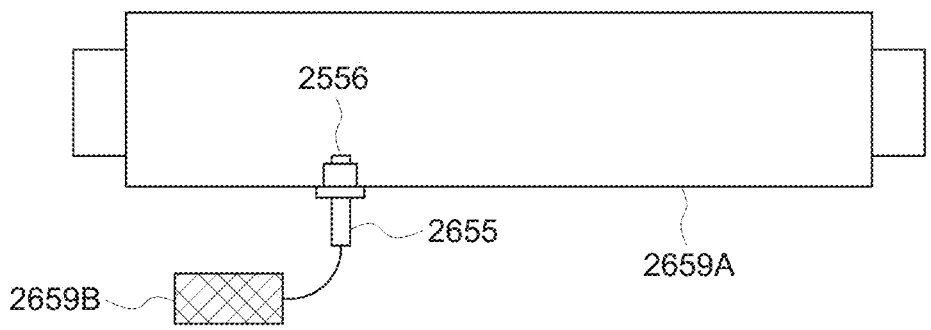
FIG. 26 is one example of sensing of fluid properties with a sensor in a fluid reservoir when the sensor is incorporated into the reservoir with the sensing region of the sensor exposed to the fluid and the sensor reader located near the sensor and connected to the sensor with a cable according to an embodiment of the disclosure.
Figure 27:
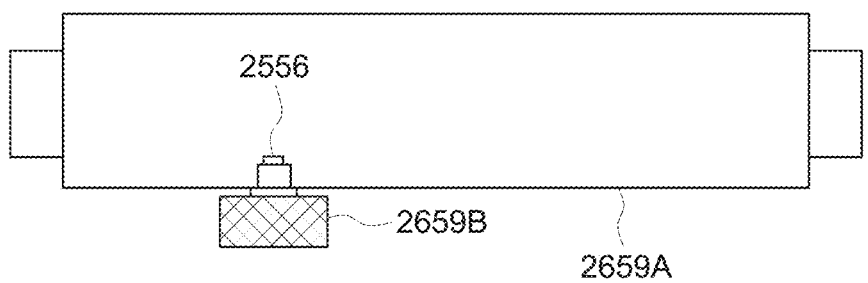
FIG. 27 is one example of sensing of fluid properties with a sensor in a fluid reservoir when the sensor is incorporated into the reservoir with the sensing region of the sensor exposed to the fluid and the sensor reader directly connected to the sensor according to an embodiment of the disclosure.

Measurements of fluid properties in fluid reservoirs may be performed using sensors with their sensing regions exposed to the fluid as shown in FIGS. 26 and 27. The sensor 2655 shown in FIG. 26 is installed in a fluid transfer pipe 2659A, and is coupled to a sensor reader 2659B. The sensor reader 2659B may be coupled by wire or cable, and located proximate to the sensor 2655 as shown in FIG. 26. In another embodiment, the sensor reader 2659B may be directly connected to the sensor without a cable—as shown in FIG. 27. During operation, a fluid flows through the pipe and contacts the sensing region 2556. As the sensing region 2556 senses an analyte of interest it signals the sensor reader 2659B.

Figure 28A:
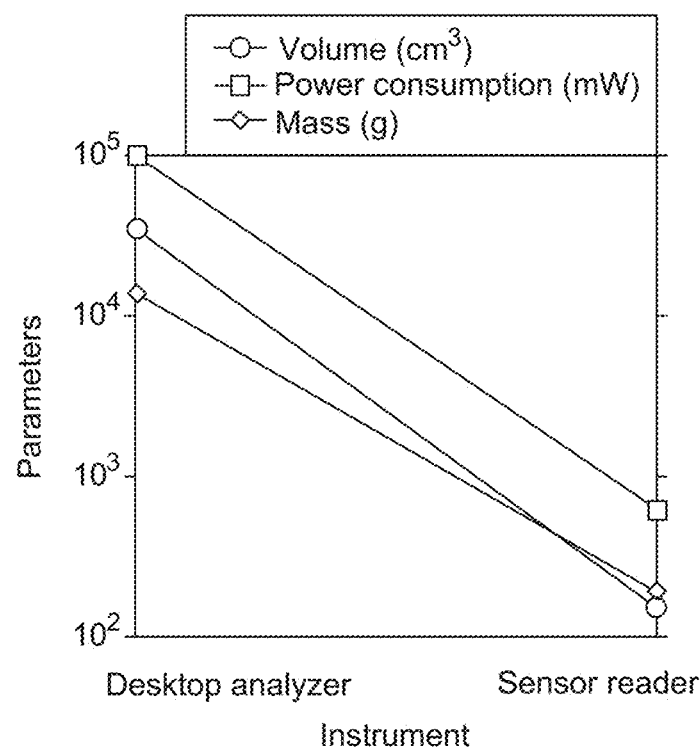
FIGS. 28A-C are graphs depicting measurements related to the sensor reader according to one embodiment.
Figure 28B:
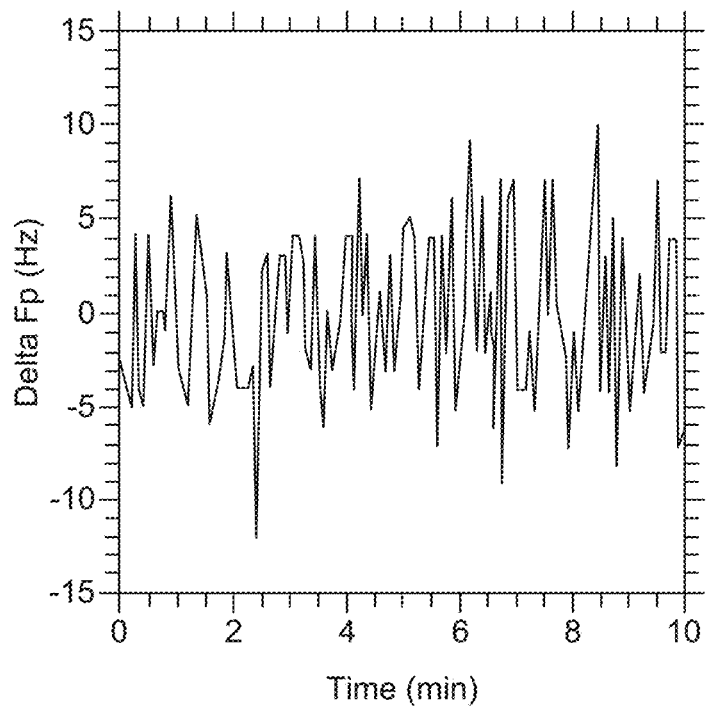
Figure 28C:
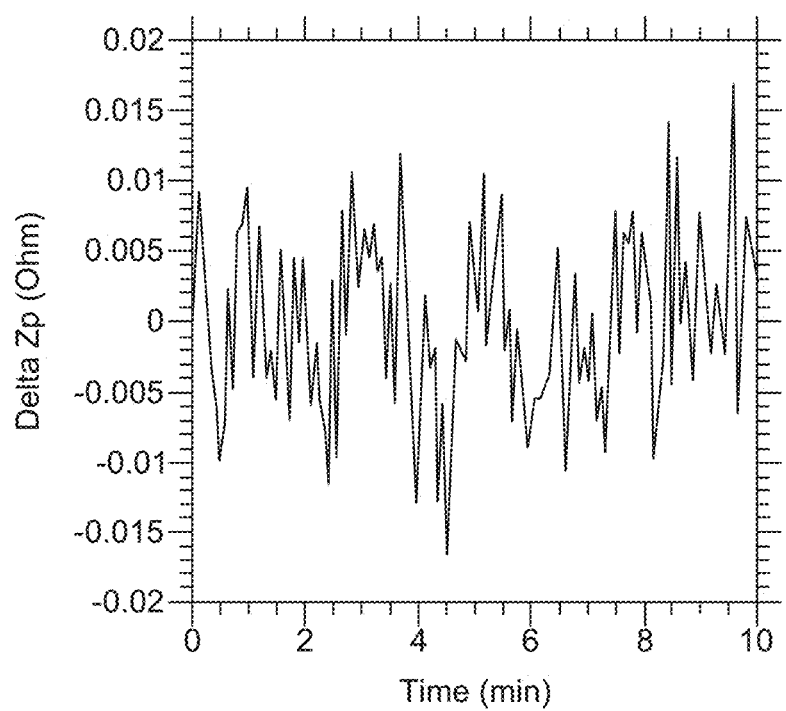

The sensor reader (also referred to as micro-analyzer) has been developed with a small form factor, low power consumption and low cost of components. FIGS. 28A-C are graphs depicting measurements related to the sensor reader according to one embodiment. FIG. 28A is a comparison of power consumption, size, and weight between a desktop analyzer and the developed micro-analyzer. FIG. 28A depicts that the design of the micro-analyzer provided 100-500-fold reduction in power consumption, size, and weight as compared to desktop analyzers. These advancements make the sensor reader attractive for a wide range of applications including monitoring of industrial fluids, where laboratory analyzers are size-, power-, and cost-prohibitive. FIGS. 28B and 28C depict measured Fp and Zp noise levels of the developed micro-analyzer, respectively. The developed sensor reader has a 1 ☐☐Fp noise of ~5 Hz and 1 ☐Zp noise of 0.006 ohm. This electronic design of the sensor reader provided 4-14 times reduction in noise levels in measurements of (f) spectra as compared to measurements with a laboratory desktop analyzer with Fp noise=60 Hz and Zp noise=0.025 Ohm.

Figure 29:
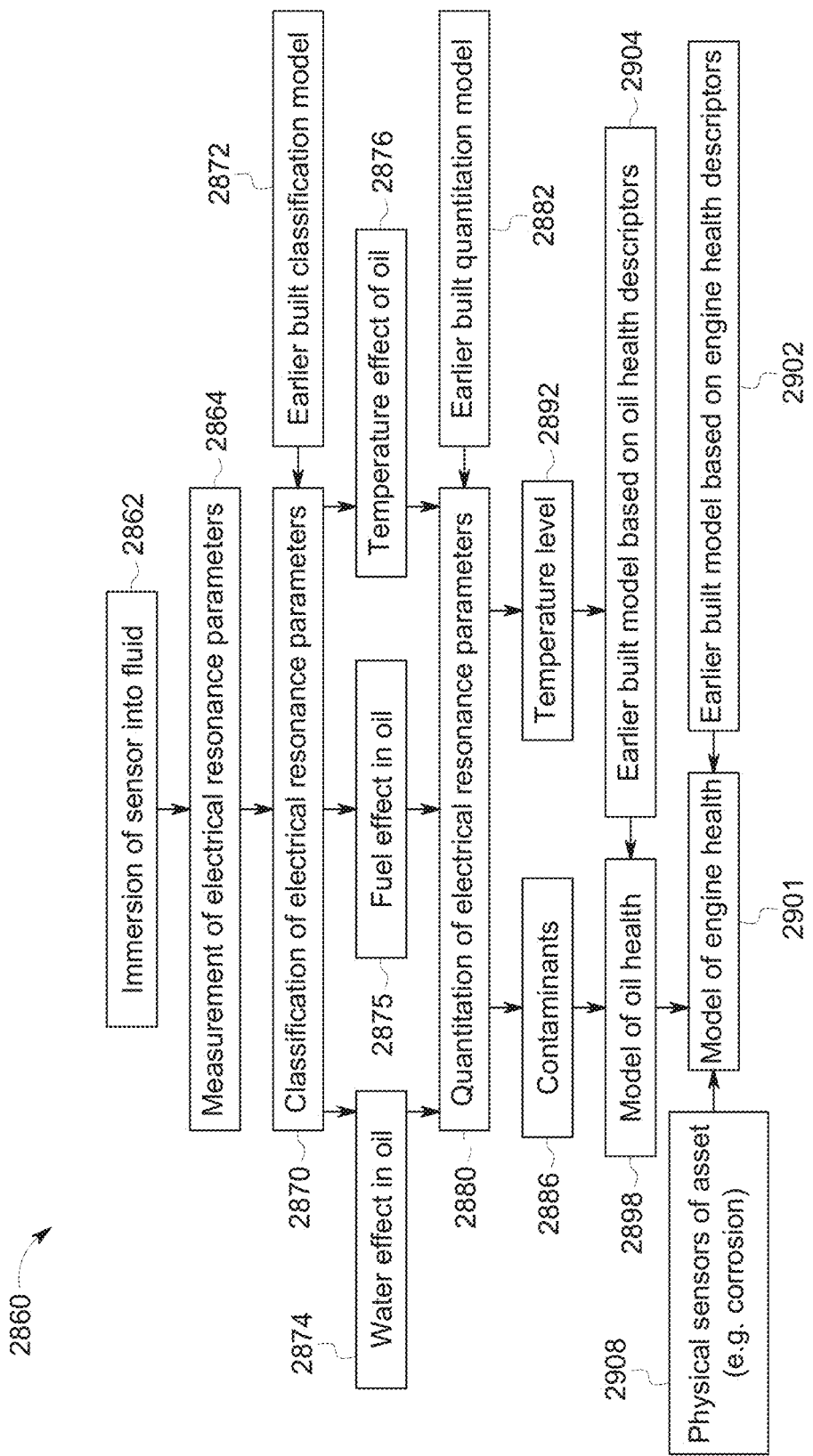
FIG. 29 is a flow diagram of fluid assessment according to an embodiment of the disclosure.

A flow diagram of a method 2860 is shown in FIG. 29. In one embodiment, a method for monitoring of oil health includes immersion of the sensor into an fluid, such as oil (step 2862) and measurement of electrical resonance parameters of the resonance spectra (step 2864) at several resonances of a single sensor. For quantitation of contamination of engine oil by water, fuel leaks, and soot with a sensor, the sensor may be placed into operational contact with the fluid at step 2862. In a specific embodiment, the resonant impedance spectra $(f)=Z_{re}(f)+jZ_{im}(f)$ of a sensor may be determined at step 2864. For example, the parameters from the measured $Z(f)$ spectra such as the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_z$ of $Z_{im}(f)$, may be calculated. In another embodiment, the electrical resonance parameters may include capacitance parameters of the sensor in operational contact with the fluid, instead or in addition to impedance parameters.

The method 2860 classifies the electrical resonance parameters at step 2870. This may be done using a determined classification model 2872 to assess, for example, one or more of water effects 2874, fuel effects 2875, and temperature effects 2876. Quantitation of the electrical resonance parameters may be performed at step 2880 by using a predetermined, earlier saved quantitation model 2882, and determination of components 2886 in oil such as water, fuel, soot, and wear metal particles 2890 as well as the temperature 2892, and prediction of the oil health 2898 and the engine health 2901. This may be done by using one or more of determined engine health descriptors 2902 and oil health descriptors 2904 as well as inputs from any additional sensors 2908. Suitable additional sensors may include those sensing corrosion, temperature, pressure, system (engine) load, system location (e.g., by GPS signal), equipment age calculator, pH, and the like.

For example, in one embodiment, a sensor system may be an electrical resonator that may be excited with a wired or wireless excitation and where a resonance spectrum may be collected and analyzed to extract at least four parameter that may be further processed upon auto scaling or mean centering of the parameters and to quantitatively predict the concentrations of water and fuel in engine oil and to predict the remaining life of the engine oil and/or the remaining life of the engine. The spectral response of the resonance spectrum such as $F_p$, $Z_p$, $F_z$, $F_1$, $F_2$, $Z_1$, and $Z_2$ or the whole resonance spectrum with a single or multiple resonators can be used for data processing.

The classification model (see model 2872 in FIG. 29) may be built using the predicted contributions of the spectral parameters for an uncontaminated fluid and for fluid contamination using previously determined component effects and their corresponding spectral parameters. Such effects may be quantified (e.g., see quantitation model 2882 in FIG. 29) to predict if a measured or sensed fluid has any water effects, fuel leak effects, or temperature effects. That is, based on previously or empirically determined effects of components on a particular fluid, the resonance parameters, both real and imaginary, may be affected in a quantifiable manner if components of interest are present. Further, based on the measured parameters, a concentration of a particular component may also be predicted, and multi-component models may be generated. The disclosed techniques may be used to sense a suitable fluid and to build a component and environmental effect model.

In one embodiment, measurements of properties of fluids may be performed at two or more temperatures of the fluid. Measurements at different temperatures provide information about species of interest and other species (chemical constituents) in the fluid when measured as the frequency dispersion profiles over the broad frequency range or when measured as frequency responses over the relatively narrow frequency range. Performing analysis of resonant impedance spectra of the sensor collected at different temperatures and determining two or more properties of the fluid per temperature based on the analyzed resonant impedance spectra allows an improvement of the sensor accuracy of determinations of properties of species of interest. This improvement may be due to differences of frequency responses of species of interest and other species in the fluid as a function of temperature caused by the molecular structure of these different species. Measurements at different temperatures may be performed with a resonant sensor that has a thermal element in thermal contact with the sensing region of the resonant sensor. The thermal element produces a local change in temperature of the fluid which may be in proximity to the sensing region. This local temperature change can be above or below the temperature of the bulk of the fluid in the container with the sensor. Non-limiting examples of thermal elements include a Peltier cooler, thin-film heater, and pencil heater. The thermal element can produce a local change in temperature of the fluid in the range from about 1 degree Celsius to about 50 degrees Celsius.

In one embodiment, measurements of properties of fluids may be performed to determine dynamic signatures of the changes of chemical constituents in the fluid. The time scales of these dynamic signatures may vary greatly. Suitable timescale in a range of from about 1 second to about 200 days may be useful to determine different types of leaks of fluids in engines. Such determinations allow the identification of dynamic signatures of the leaks in an engine, relation of the identified signature with the known leak signature from a specific engine component, and determination of the location of the leak based on the signature.

Measurements of properties of fluids may be performed at extreme temperature conditions. Depending on the application, these conditions may range from temperatures down to about −260 degrees Celsius and to temperatures up to about +1600 degrees Celsius. Such harsh temperature conditions with negative temperature down to about −260 degrees Celsius may be useful in relation to liquefied natural gas (LNG) and in the storage of biological and other types of samples. Harsh temperature conditions with positive temperature of up to about +1600 degrees Celsius may be useful in monitoring equipment where the temperature of operating components of the equipment can reach about +1600 degrees Celsius. Examples of equipment that operates at about 250 degrees Celsius may include downhole equipment in oil and gas production and the operations of an internal combustion engine (diesel, natural gas, hydrogen (direct combustion or fuel cells), gasoline, combinations thereof, and the like) for one or more of the fuel, the lubrication system, and the cooling/radiator system. Another example of such equipment may include an oil-filled transformer. Examples of equipment that operates at about 1000 and up to 1500 degrees Celsius include gas turbines. Examples of equipment that operates at about 1600 degrees Celsius include aircraft jet engines.

The applicability of multivariable electrical resonators may be demonstrated by detection of engine oil contamination from water and diesel fuel and determinations of water in model fluid such as dioxane that has the dielectric constant similar to oil. Determination of resolution of the sensor measurements may be performed using hexane and toluene as model systems. Samples of some engine oil were obtained from GE Transportation, while other chemicals may be commercially obtained from Aldrich.

Measurements of the resonant impedance of sensors may be performed with a network analyzer (Agilent) or a precision impedance analyzer (Agilent), under computer control using LabVIEW. Collected resonant impedance data may be analyzed using KaleidaGraph (Synergy Software, Reading, Pa.) and PLS Toolbox (Eigenvector Research, Inc., Manson, Wash.) operated with Matlab (The Mathworks Inc., Natick, Mass.).

Different amounts of fuel and water leaks into oil may be determined quantitatively and experimentally with a single multivariable resonant sensor. Suitable oil may be railroad internal combustion engine oil. Suitable fuel may be diesel fuel. Binary and ternary mixtures of water and fuel in oil may be produced in different proportions. Concentrations of water may be 0, 0.1% and 0.2% (by volume). Concentrations of fuel may be 0, 3% and 6% (by volume).

Figure 30:
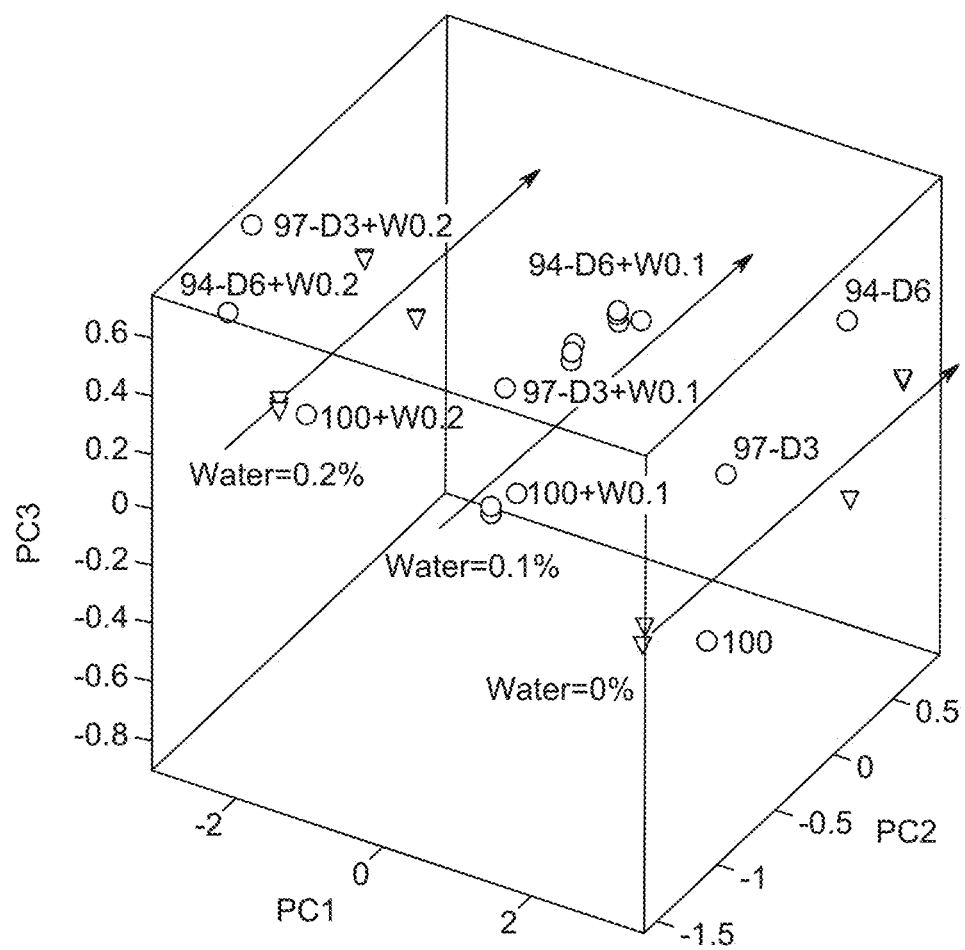
FIG. 30 is a plot of a resonant impedance data for detection of engine oil, water, and fuel with a highlighted water leak.
Figure 31:
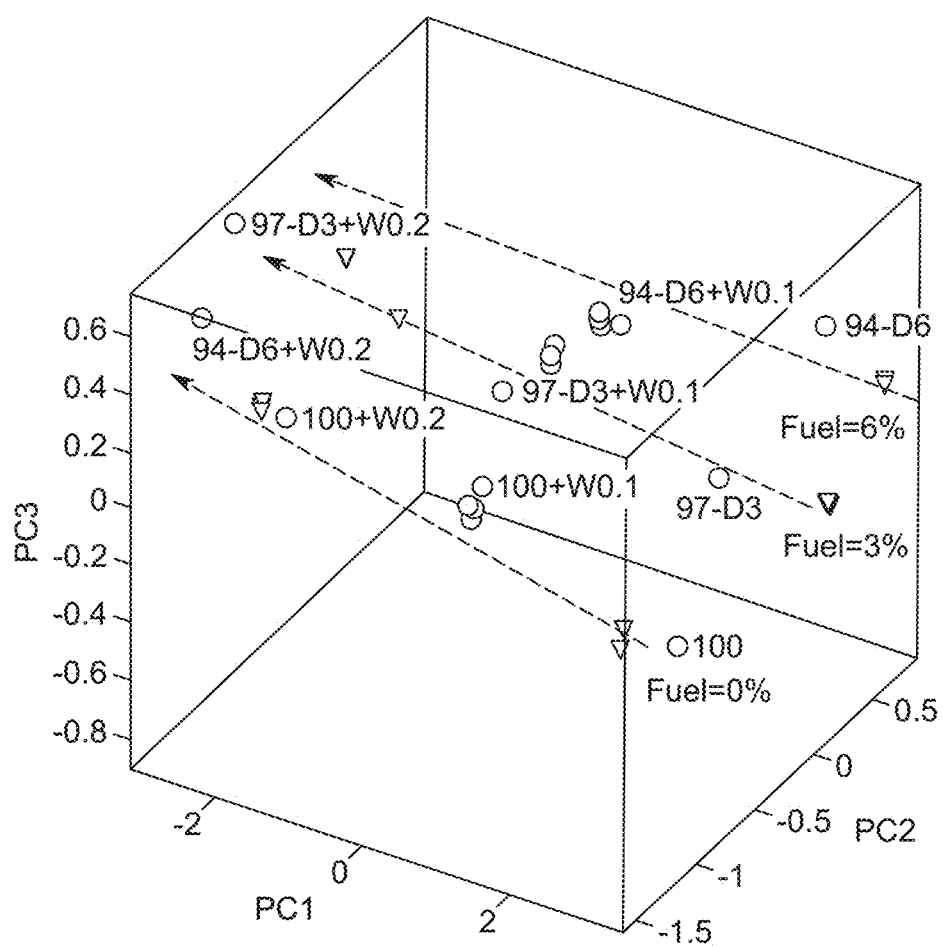
FIG. 31 is a plot of a resonant impedance data for detection of engine oil, water, and fuel with a highlighted fuel leak.

The resonance spectra from measured samples may be processed and the processed data served as inputs to the principal components analysis (PCA) tool. PCA may be a pattern recognition method that explains the variance of the data as the weighted sums of the original variables, known as principal components (PCs). A highlight of detection of water in mixtures of engine oil, water, and fuel may be illustrated in FIG. 30 that depicts a scores plot of a developed PCA model. A highlight of detection of fuel in mixtures of engine oil, water, and fuel may be illustrated in FIG. 31 that depicts a scores plot of a developed PCA model. In FIGS. 30 and 31, concentrations of water of 0.1% and 0.2% are labeled as W0.1 and W0.2, respectively. Concentrations of fuel of 3% and 6% are labeled as D3 and D6, respectively. The multivariable response of the resonant transducers originates from the measured whole resonance spectra of the transducer followed by the processing of these spectra using multivariate analysis tools. For quantitation of contamination of engine oil by water and fuel leaks with a single multivariable sensor, the resonant impedance spectra $(f)=Z_{re}(f)+jZ_{im}(f)$ of the resonant transducer may be measured. Several parameters from the measured (f) spectra may be calculated that included the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_z$ of $Z_{im}(f)$ as shown in FIG. 23.

Figure 32:
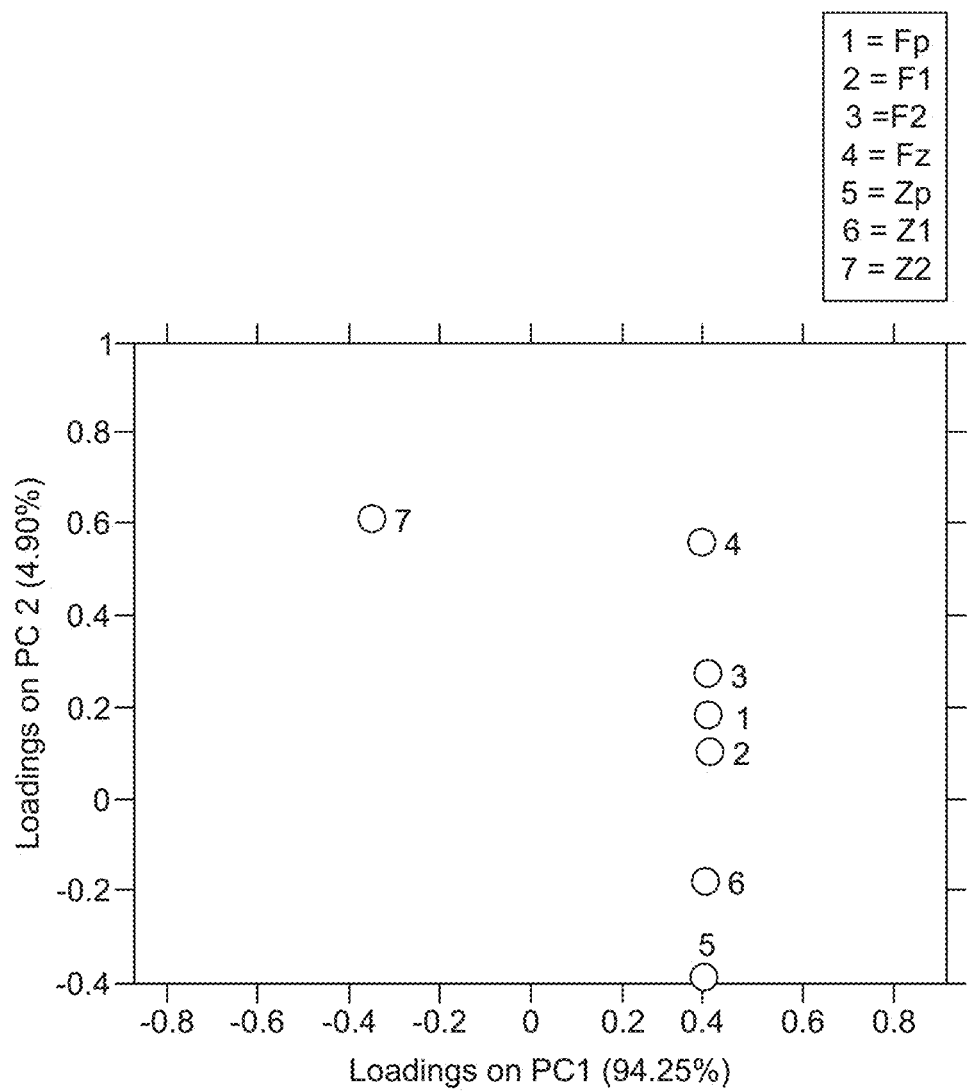
FIG. 32 is a principal components analysis of resonant impedance spectral parameters.

By using multivariate analysis of calculated parameters of (f) spectra, classification of analyte may be performed. Suitable analysis techniques for multivariate analysis of spectral data from the multivariable sensors may include Principal Components Analysis (PCA), Independent Component Analysis (ICA), Linear Discriminant Analysis (LDA), and Flexible Discriminant Analysis (FDA). PCA may be used to discriminate between different vapors using the peptide-based sensing material. A loadings plot of the PCA model is illustrated in FIG. 32. This plot illustrates the contributions of individual components from the resonance spectrum. The plot shows that all components such as Fp, F1, F2, Fz, Zp, Z1, and Z2 had contributions to the sensor response.

Figure 33:
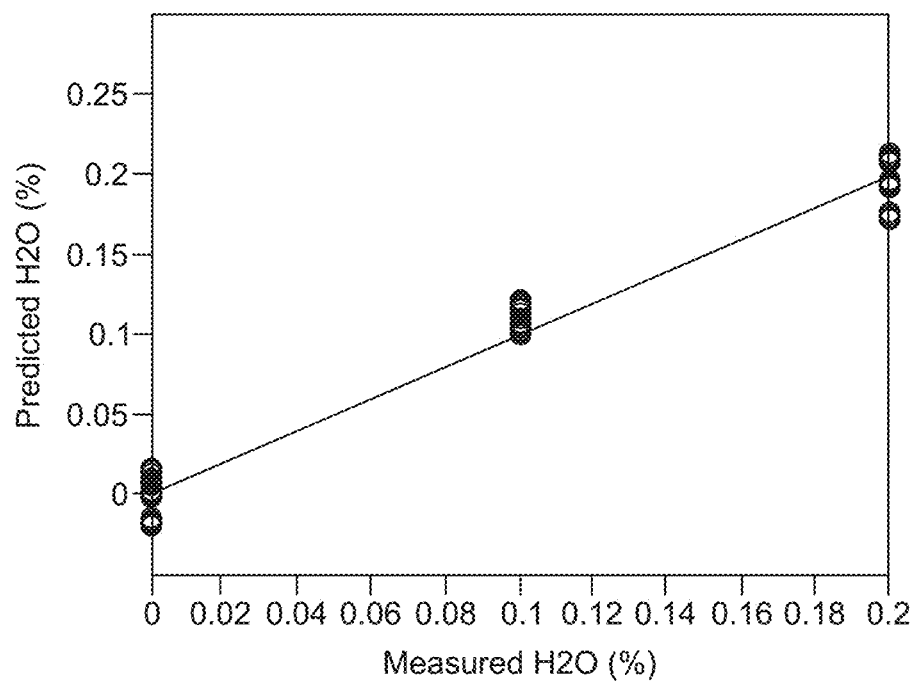
FIG. 33 is a correlation plot between the actual (measured) and predicted concentrations of water in water/fuel/oil mixtures using a single resonant sensor.
Figure 34:
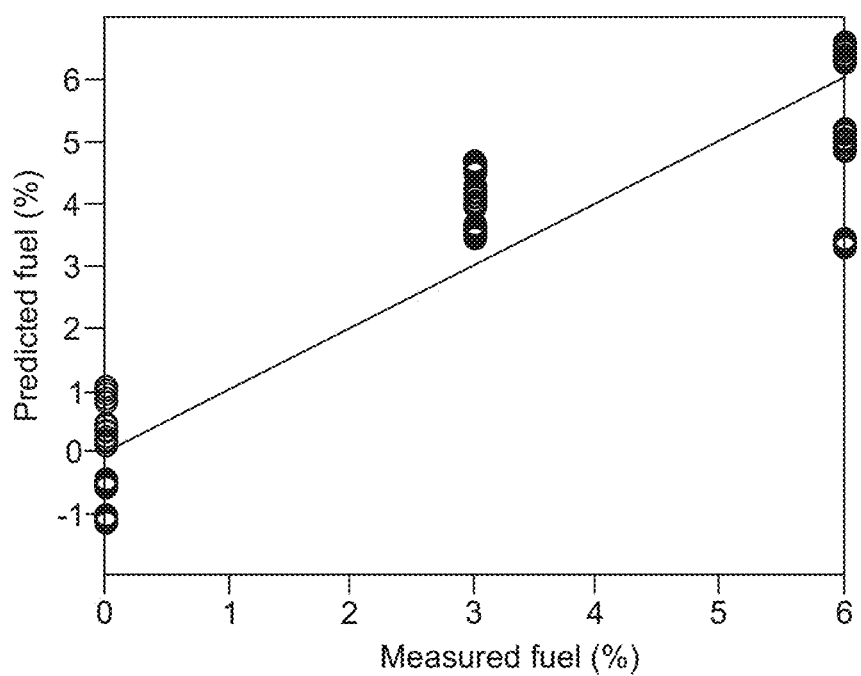
FIG. 34 is a correlation plot between the actual (measured) and predicted concentrations of fuel in water/fuel/oil mixtures using a single resonant sensor.

Quantitation of water and fuel in oil in their binary and ternary mixtures may be further performed with a single multivariable resonant sensor using PLS Toolbox (Eigenvector Research, Inc., Manson, Wash.) operated with Matlab (The Mathworks Inc., Natick, Mass.). FIG. 33 shows a correlation plot between actual (measured) and predicted concentrations of water in water/fuel/oil mixtures using a single resonant sensor. FIG. 34 shows a correlation plot between measured and predicted concentrations of fuel in water/fuel/oil mixtures using a single resonant sensor. Prediction errors of simultaneous quantitation of water and fuel in oil with the single sensor may be 0.02% of water and 1.3% of fuel.

Figure 35:
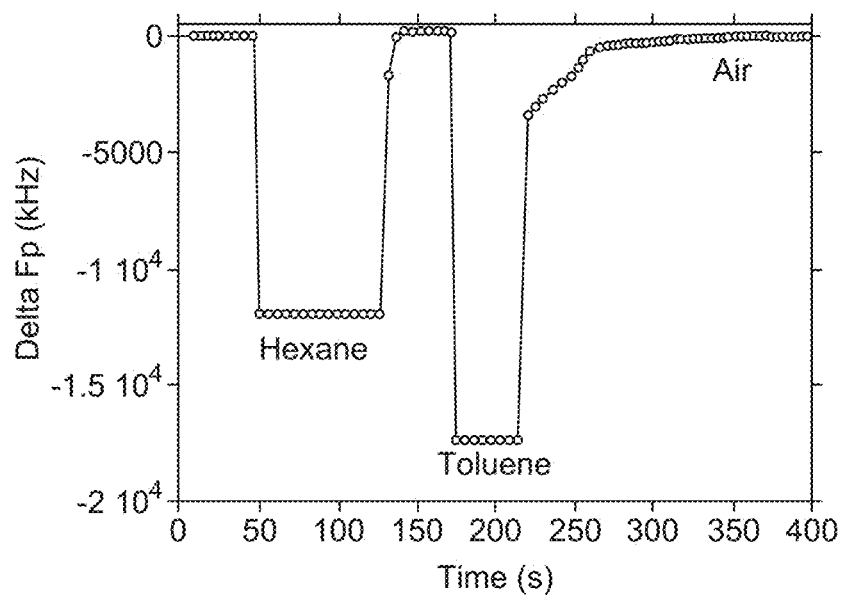
FIG. 35 is a plot of a spectral parameter showing resolution of a resonant sensor to distinguish between hexane and toluene.
Figure 36:
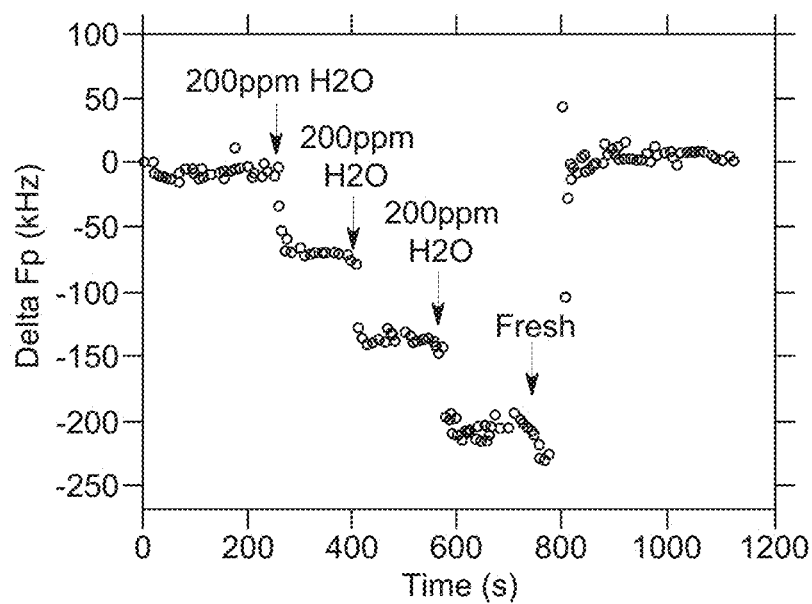
FIG. 36 is a plot of a spectral parameter showing resolution of water addition into dioxane.

In another example, sensor resolution may be determined in multi-part experiments. In a first experiment, hexane and toluene may be used as model chemicals to determine the ability of the sensor to resolve differences in the dielectric constant. Hexane has the dielectric constant of 1.88 while toluene has the dielectric constant of 2.38. A developed sensor may resolve these two liquids with the resolution of the dielectric constant of 0.0004-0.0012. Expected results are shown in FIG. 35. In the second experiment, 1,4-dioxane may be used as a model chemical for oil because of its the dielectric constant similar to oil and the ability to be easily miscible with water. The sensor may resolve water additions into dioxane down to 7-20 ppm. Expected results are shown in FIG. 36 illustrating that the developed sensor may be able to resolve water additions into dioxane (model system for oil) down to 7-20 ppm with water additions done in increments of 200 ppm.

Figure 37:
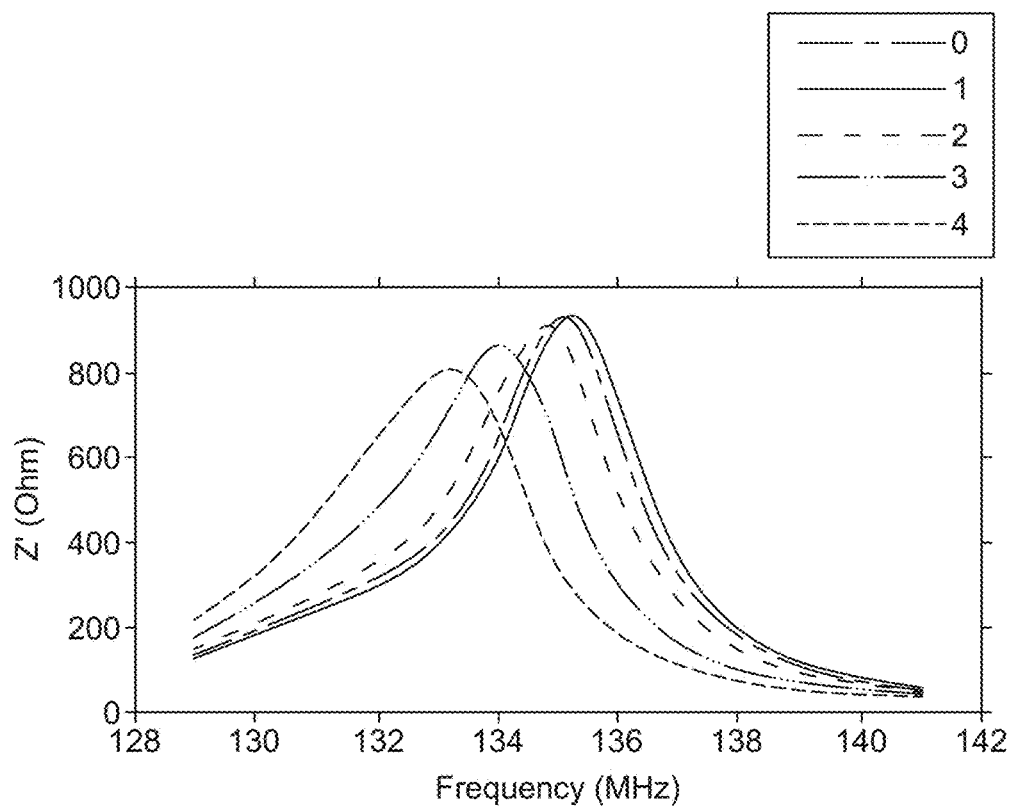
FIG. 37 is a plot of the real part of resonant impedance spectra after soot and water addition.
Figure 38:
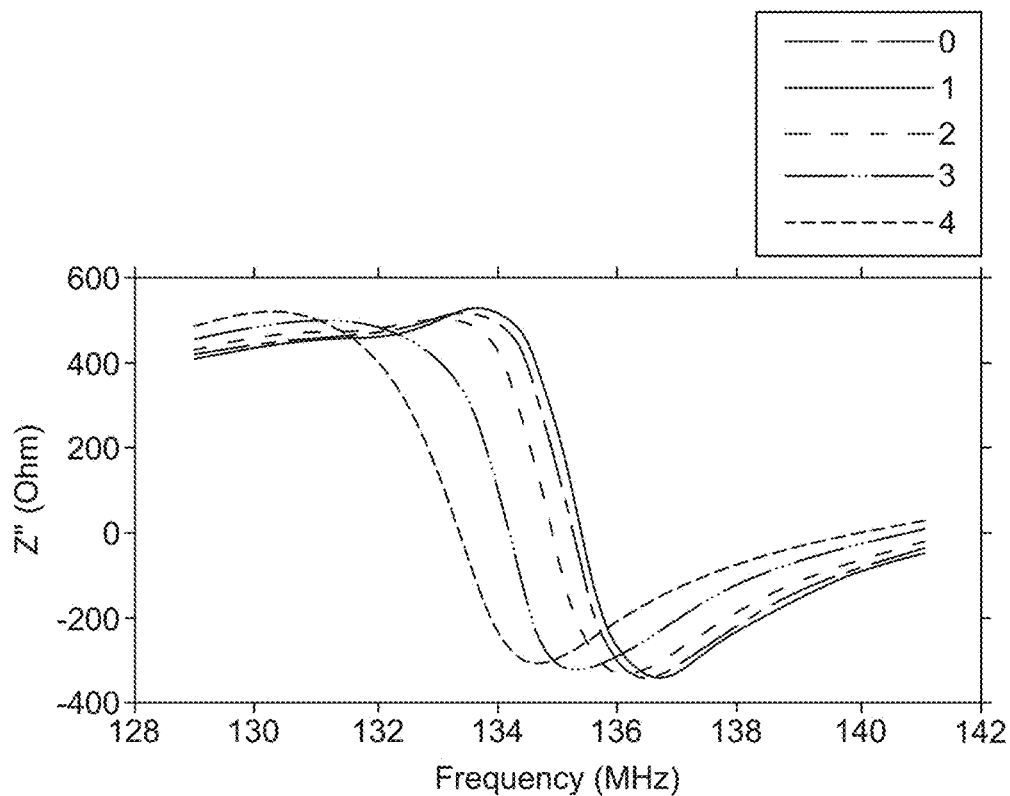
FIG. 38 is a plot of the imaginary part of resonant impedance spectra after soot and water addition.
Figure 39:
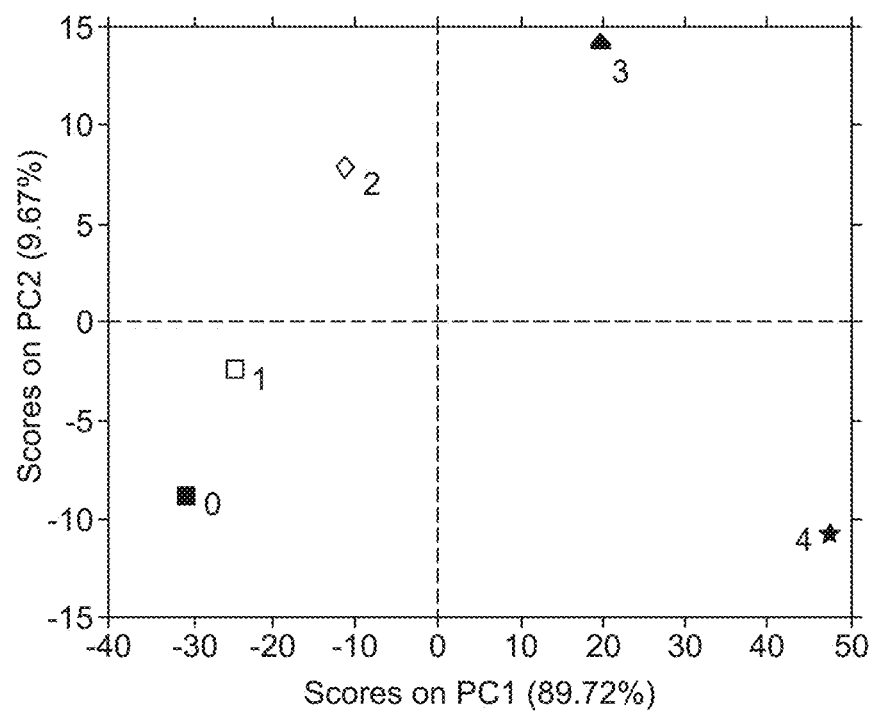
FIG. 39 depicts the PCA scores plot of PC1 vs. PC2 upon exposure of sensor to five solutions and performing resonance impedance measurements.

In another example, water and soot (carbon black) additions may be done to dioxane and measured with a sensor. Water additions may be done as 500 ppm, 1000 ppm, and 2500 ppm additions. Soot (carbon black) may be added as 100 ppm carbon black with 2500 ppm of water. Exemplary resonance spectra of a sensor are presented in FIGS. 37 and 38. Results of multivariate analysis are presented in FIG. 39. FIG. 37 shows the real part $Z_{re(f)}$ and FIG. 38 shows imaginary part $Z_{im(f)}$ of resonant impedance. Measured samples may be: (0) clean model oil (dioxane); (1) addition of 500 ppm of water; (2) addition of 1000 ppm of water, (3) addition of 2500 ppm of water; (4) addition of 2500 ppm of water and 100 ppm of soot (carbon black). FIG. 39 shows a scores plot of Principal component 1 (PC1) vs. Principal component 2 (PC2) illustrating spectral relation between sensor responses to different types of contamination. Samples may be: (0) clean model oil (dioxane); (1) addition of 500 ppm of water; (2) addition of 1000 ppm of water; (3) addition of 2500 ppm of water; (4) addition of 2500 ppm of water and 100 ppm of soot (as carbon black).

Figure 40:
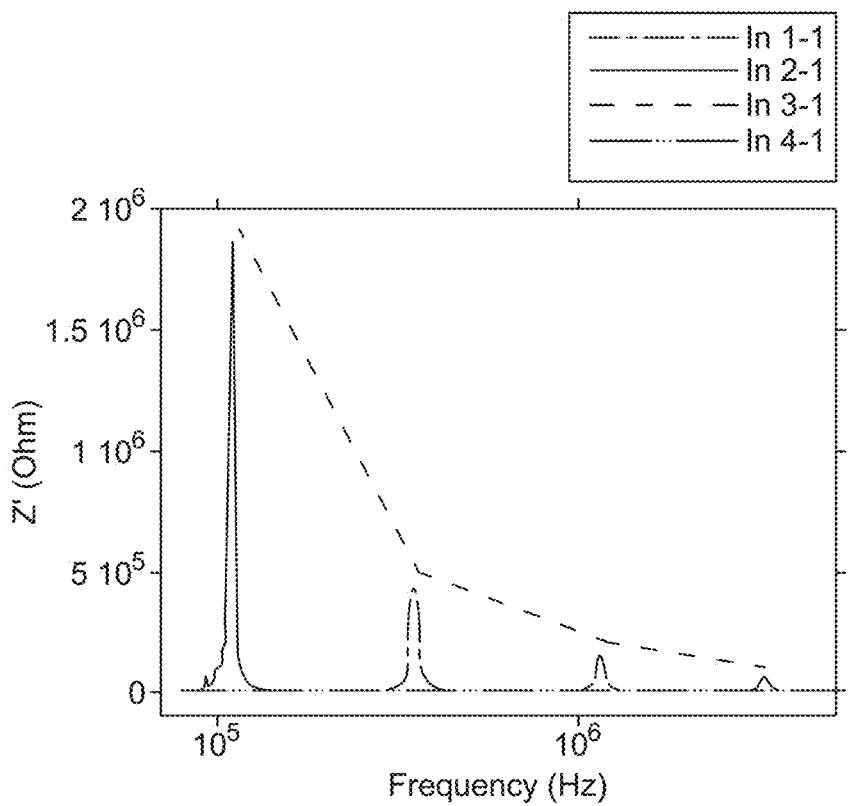
FIG. 40 displays a plot of four resonant spectral profiles from a single sensor for uncontaminated dioxane.
Figure 41:
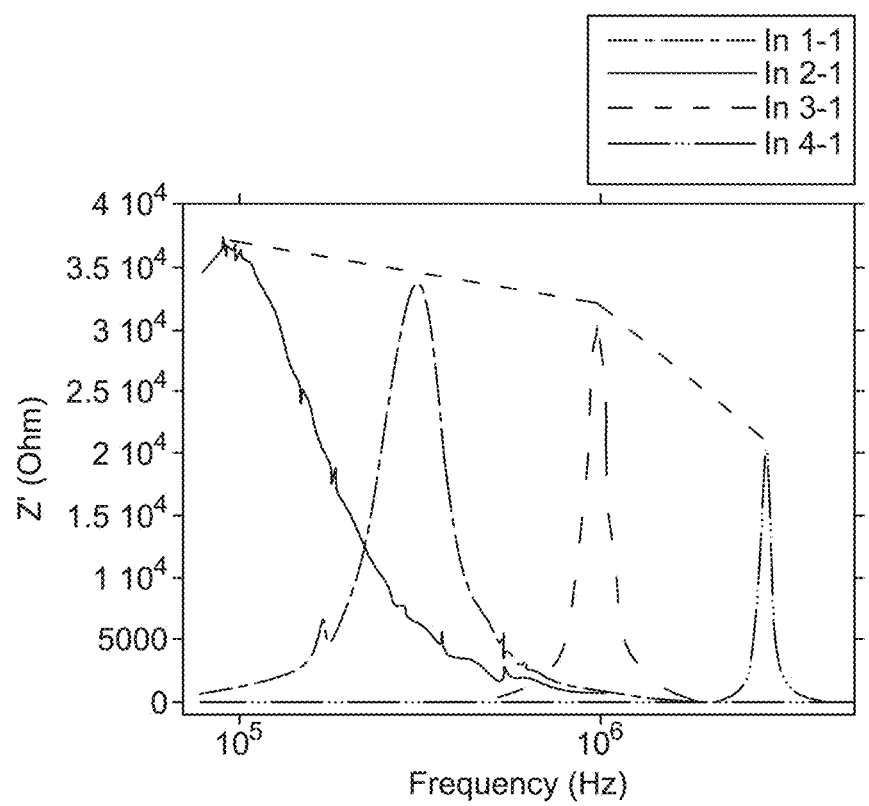
FIG. 41 displays a plot of resonant spectral profiles from a single sensor upon addition of water into the dioxane.

In another example, a multiresonant sensor system may be built with four resonant frequencies. The 1,4-dioxane can be used as a model chemical for oil, because its dielectric constant is somewhat similar to oil and it is miscible with water. Water additions may be done to dioxane and measured with a sensor. Four example resonance spectra of the sensor are presented in FIGS. 39 and 40. These values illustrate that the dispersion profile of the sensor in non-contaminated dioxane (as shown in FIG. 40) has changed its shape upon addition of water (as shown in FIG. 41). Also, the widths and the magnitudes of the resonance peaks have been modified by water addition.

Figure 42:
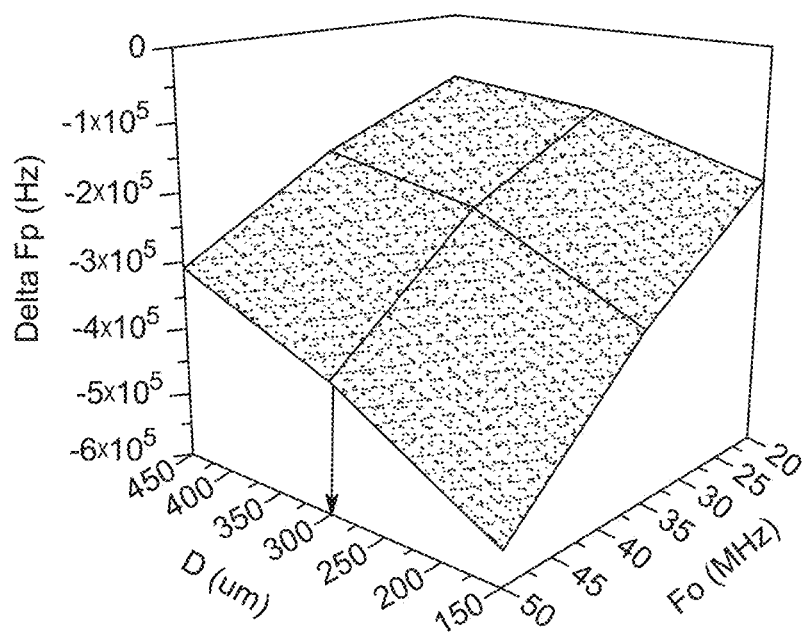
FIG. 42 is plot of effects of sensor design on sensitivity of Fp measurements.
Figure 43:
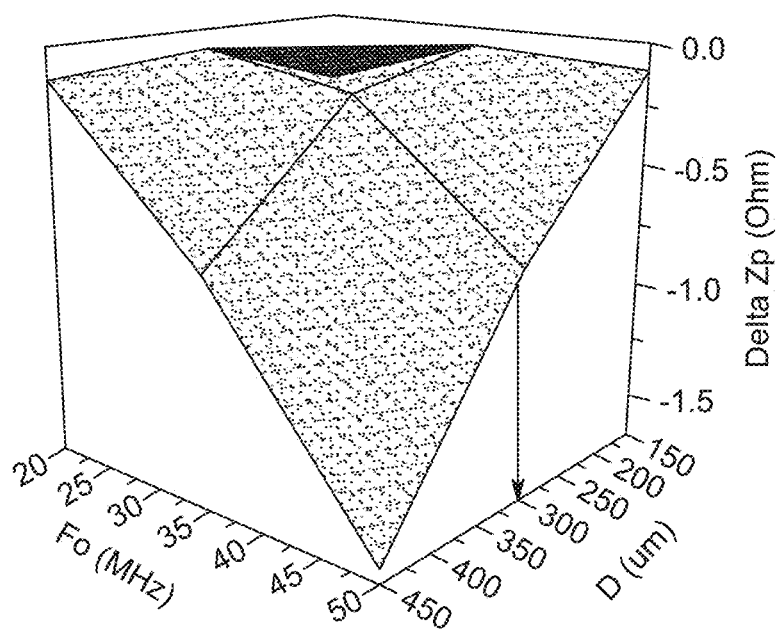
FIG. 43 displays effects of sensor design on sensitivity of Zp measurements.

In another example, sensor electrode geometries and resonant frequency may be optimized for the maximum Fp and Zp responses to water. A two-factor design of experiments may be done by varying interdigital electrode (IDE) spacing D and electrode width W, where D=W=150, 300, 450 micrometers (μm) and varying resonance frequency, Fp, as Fp=20, 35, 50 MHz (in air). Measurements may be performed by adding water to dioxane at 5000 ppm concentration. FIG. 42 shows effects of sensor design on sensitivity of Fp measurements. FIG. 43 shows effects of sensor design on sensitivity of Zp measurements. A 300 μm IDE spacing and 50 MHz operation frequency yielded both strong Fp and Zp signals.

Figure 44:
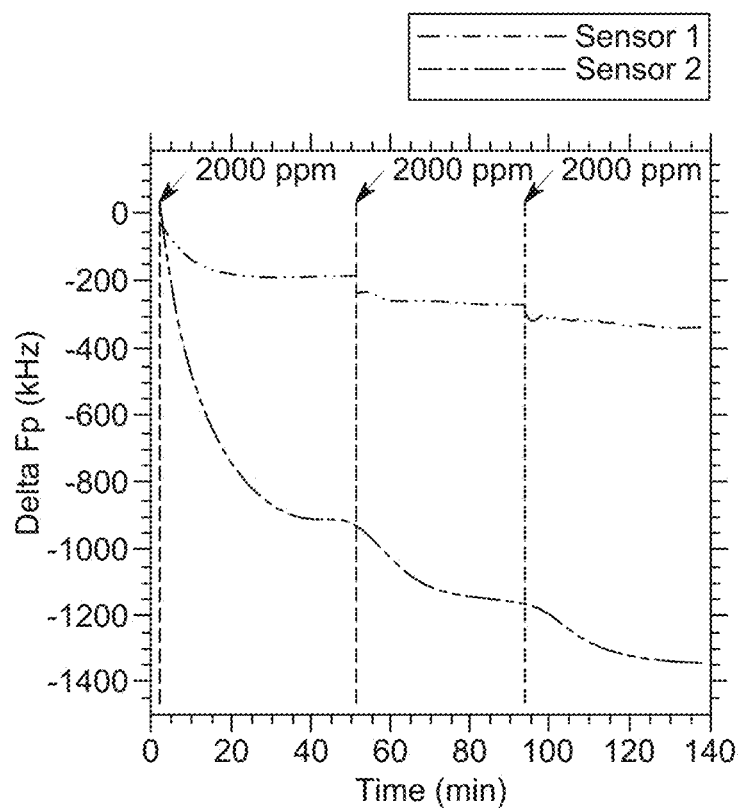
FIG. 44 is plot of results of measurements of water in oil with two multivariable resonant sensors.

In another example shown in FIG. 44, determination of water in oil may be performed by circulating oil in a test loop and adding water at 2000 ppm increments to generate water concentrations in oil of 2000 ppm, 4000 ppm, and 6000 ppm. Measurements may be performed using two resonant sensors. Sensor 1 had area of 2 cm$^2$ with the electrode width/spacing of 0.4 mm/0.4 mm and resonating at 80 MHz in air. Sensor 2 may be one of geometries from the design of experiments and had area of 4 cm$^2$ with the electrode width/spacing of 0.15 mm/0.15 mm and resonating at ~50 MHz in air. The limit of detection of water in oil may be determined at the signal-to-noise level of three to be 3-12 ppm (Sensor 1) and 0.6-2.6 ppm (Sensor 2) based on the measured sensor noise levels and signal levels at 2000 ppm of added water.

Figure 45:
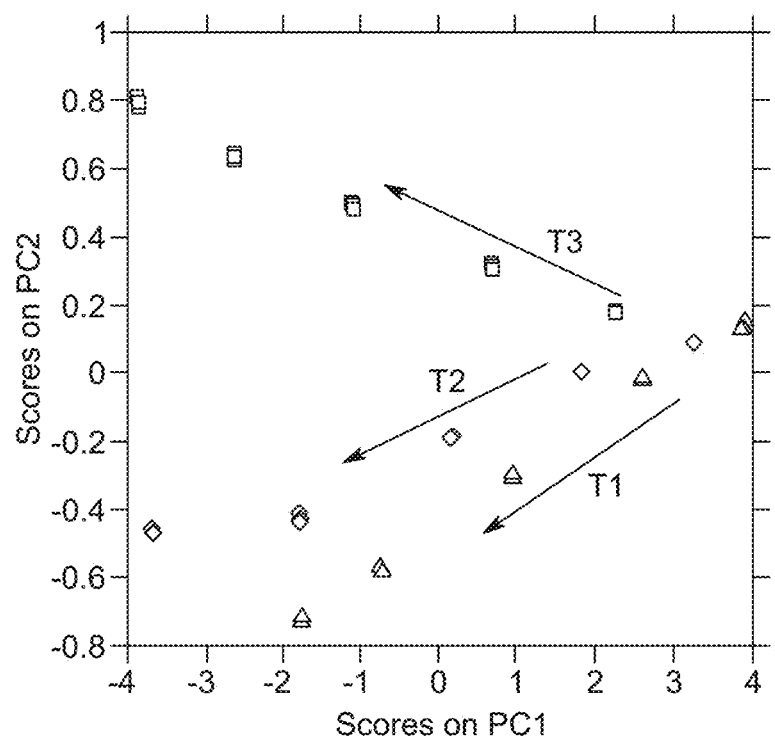
FIG. 45 is a scores plot of a developed PCA model of responses of the resonant sensor to additions of water at different temperatures, showing different response directions.
Figure 46:
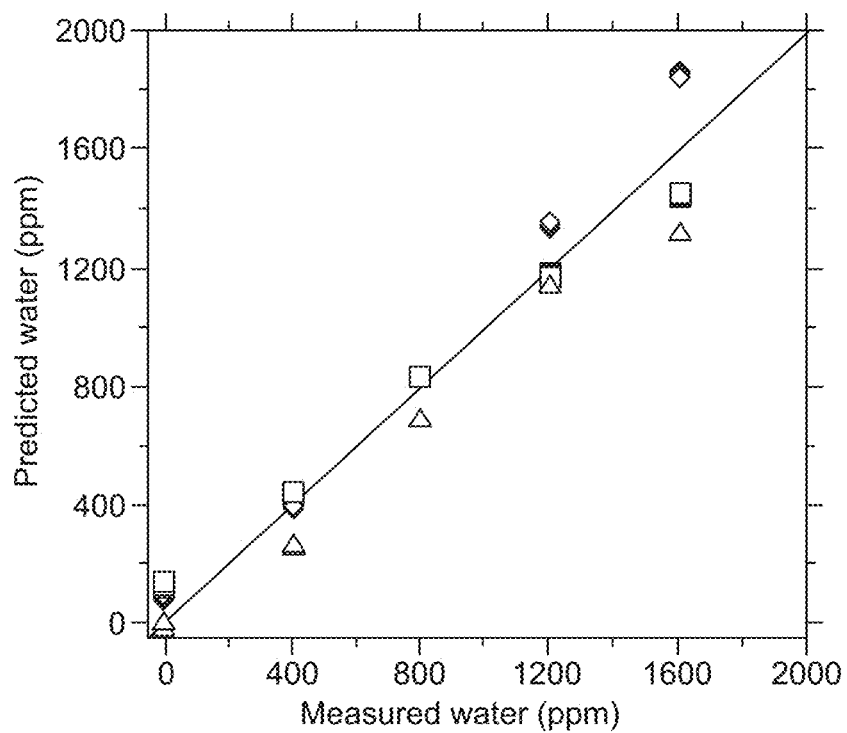
FIG. 46 is plot of results of multivariate linear regression model using partial least squares technique to quantify water concentrations in oil using responses of the single sensor.
Figure 47:
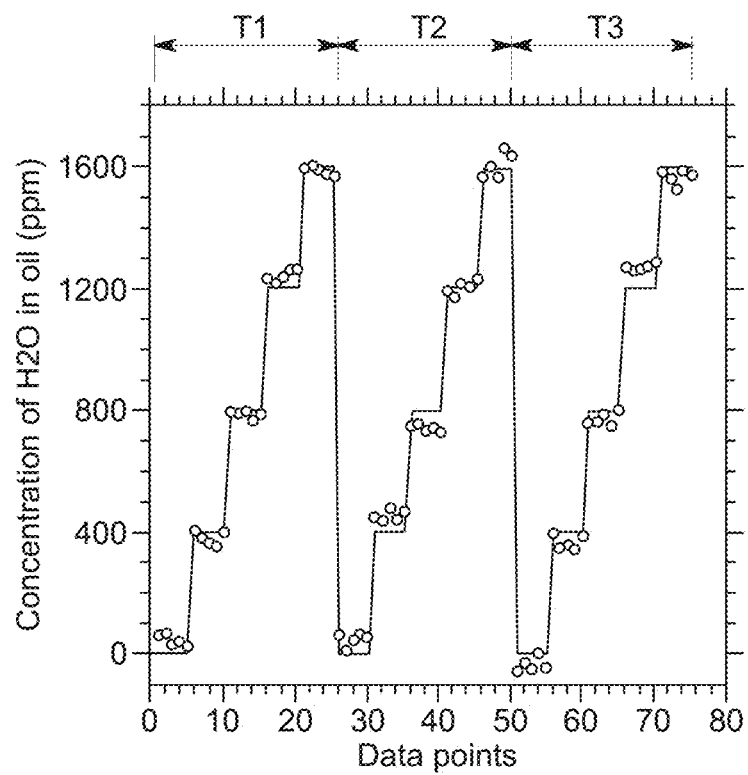
FIG. 47 is a plot of the actual (measured) concentrations of water in oil over time at three temperatures (solid line) and predicted concentrations (open circles).

In another example, determination of water in oil at different oil temperatures may be performed by circulating oil in a test loop and adding water at 400 ppm increments to generate water concentrations in oil of 400 ppm, 800 ppm, 1200 ppm, and 1600 ppm. The nominal temperatures of oil may be T1=80 degrees Celsius, T2=100 degrees Celsius, and T3=120 degrees Celsius as produced by a thermal bath. FIG. 45 depicts a scores plot of a developed PCA model illustrating that responses of the resonant sensor to additions of water at different temperatures may be in different directions. Each individual arrow in FIG. 45 points in the direction of increasing water concentrations at oil temperatures T1, T2, and T3. FIG. 46 may depict results of multivariate linear regression model using partial least squares (PLS) technique to quantify water concentrations in oil using responses of the single sensor. The PLS technique may determine correlations between the independent variables and the sensor response by finding the direction in the multidimensional space of the sensor response that explains the maximum variance for the independent variables. FIG. 47 shows that such multivariate linear regression may be able to predict water concentrations independent of oil temperature.

Figure 48:
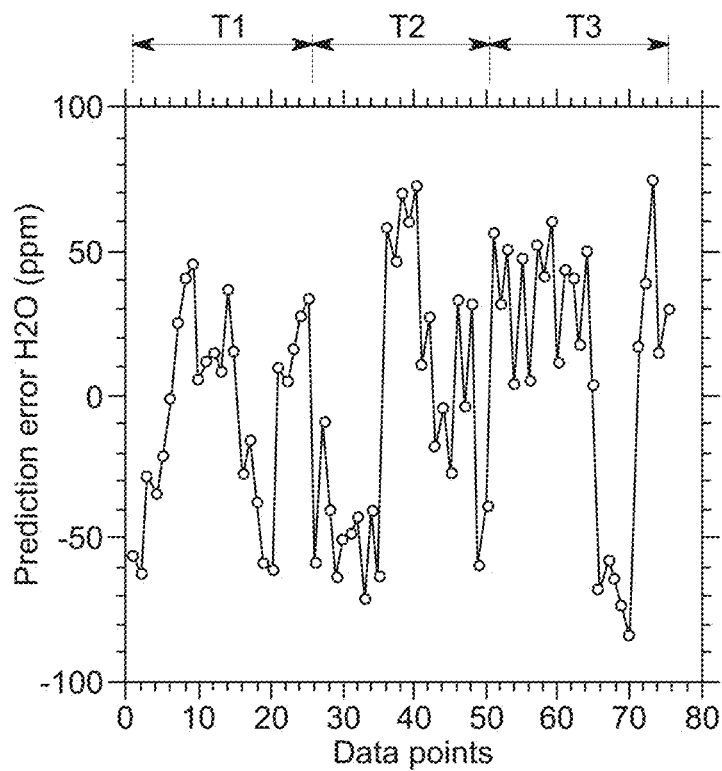
FIG. 48 is a plot of prediction error between actual and predicted concentrations of water in oil over time at three temperatures.
Figure 49:
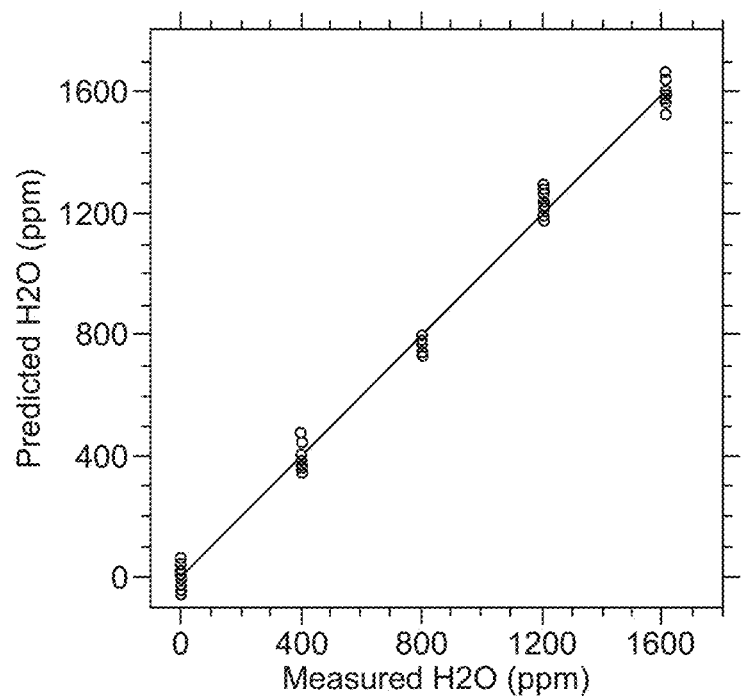
FIG. 49 is a plot of correlation between actual (measured) and predicted concentrations of water in oil at three temperatures.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be performed using a multivariate non-linear (quadratic) regression. FIG. 47 depicts the actual (measured) concentrations of water in oil at three temperatures (solid line) and predicted concentrations (open circles). FIG. 48 depicts prediction error between actual and predicted concentrations of water in oil at three temperatures. FIG. 49 depicts a correlation plot between actual (measured) and predicted concentrations of water in oil at three temperatures.

Figure 50:
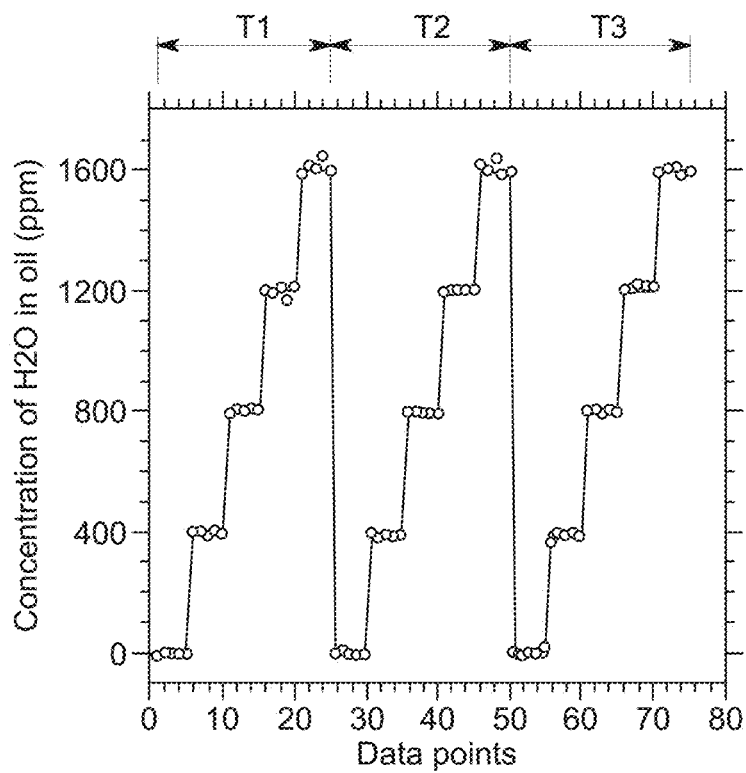
FIG. 50 is a plot of the actual (measured) concentrations of water in oil over time at three temperatures (solid line) and predicted concentrations (open circles) using responses of a multivariable resonant sensor and oil temperature sensor.
Figure 51:
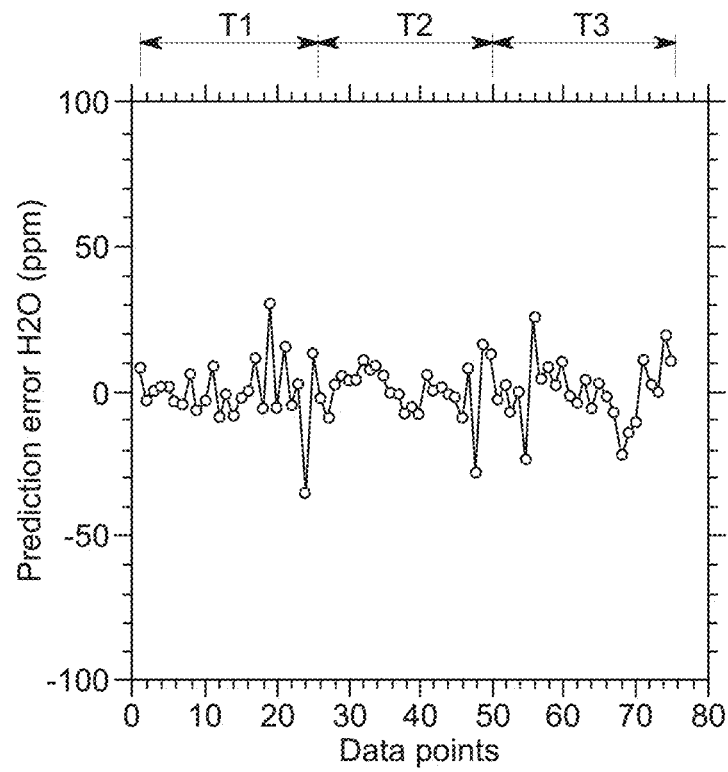
FIG. 51 is a plot of prediction error between actual and predicted concentrations of water in oil over time at three temperatures using responses of a multivariable resonant sensor and oil temperature sensor.
Figure 52:
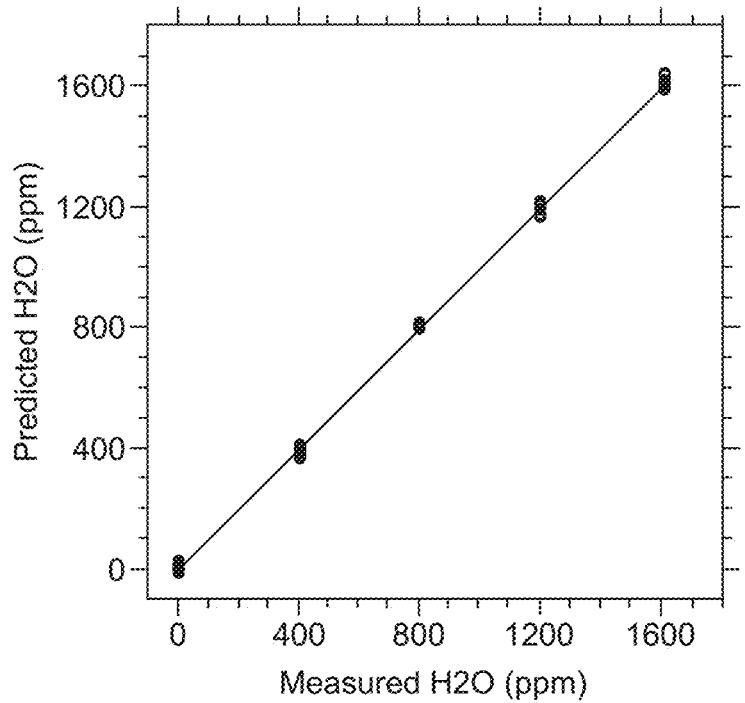
FIG. 52 is a plot of correlation between actual (measured) and predicted concentrations of water in oil at three temperatures using responses of a multivariable resonant sensor and oil temperature sensor.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be further performed using a multivariate non-linear (quadratic) regression with an additional input from a temperature sensor positioned in measured oil. FIG. 50 depicts the actual (measured) concentrations of water in oil at three temperatures (solid line) and predicted concentrations (open circles). FIG. 51 depicts prediction error between actual and predicted concentrations of water in oil at three temperatures. FIG. 52 depicts a correlation plot between actual (measured) and predicted concentrations of water in oil at three temperatures.

Figure 53:
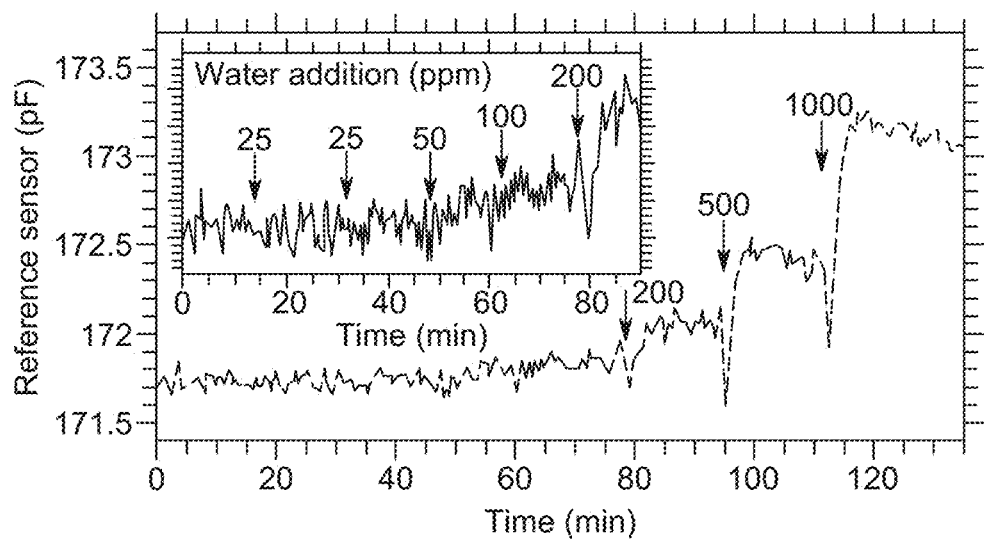
FIG. 53 is a response of a reference capacitance sensor to water leaks into engine oil at levels of 25, 25, 50, 100, 200, 500, and 1000 ppm each. Inset shows response to initial water leaks.
Figure 54:
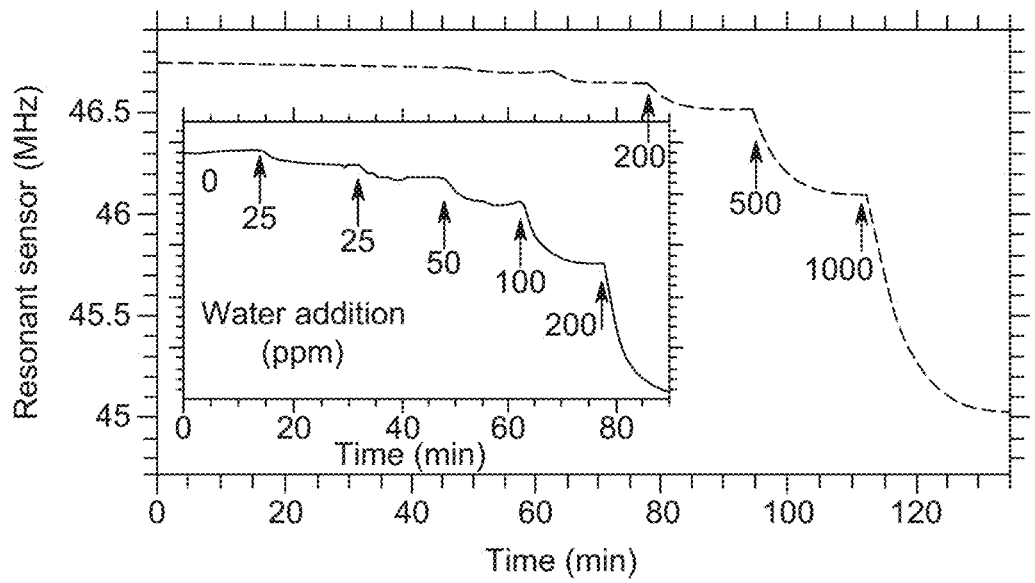
FIG. 54 is a response of a developed resonant sensor to water leaks into engine oil at levels of 25, 25, 50, 100, 200, 500, and 1000 ppm each. Inset shows response to initial water leaks.

The performance of this developed resonant sensor may compare with the performance of a standard non-resonant capacitance sensor that served as a reference capacitance sensor. This reference capacitance sensor has two co-axis pipes, and it is possible to measure capacitance of the fluid being tested by applying a sinusoidal signal to the inner pipe. The comparison may be performed by having both sensors in the same circulating-oil loop where water leaks may be introduced and presented to both sensors. Water leaks levels may be 25, 25, 50, 100, 200, 500, and 1000 ppm. FIG. 53 depicts the response of a reference capacitance sensor to water leaks into engine oil at levels of 25, 25, 50, 100, 200, 500, and 1000 ppm each. This figure illustrates that the reference capacitance sensor did not show an appreciable signal change from its noise until water leaks of 25, 25, 50, 100, and 200 ppm 200 ppm may be introduced. In contrast, FIG. 54 shows the response of a resonant sensor according to an embodiment to water leaks into engine oil where this sensor may detect the smallest water leak at 25 ppm and detected all other water leaks presented to both sensors.

Figure 55:
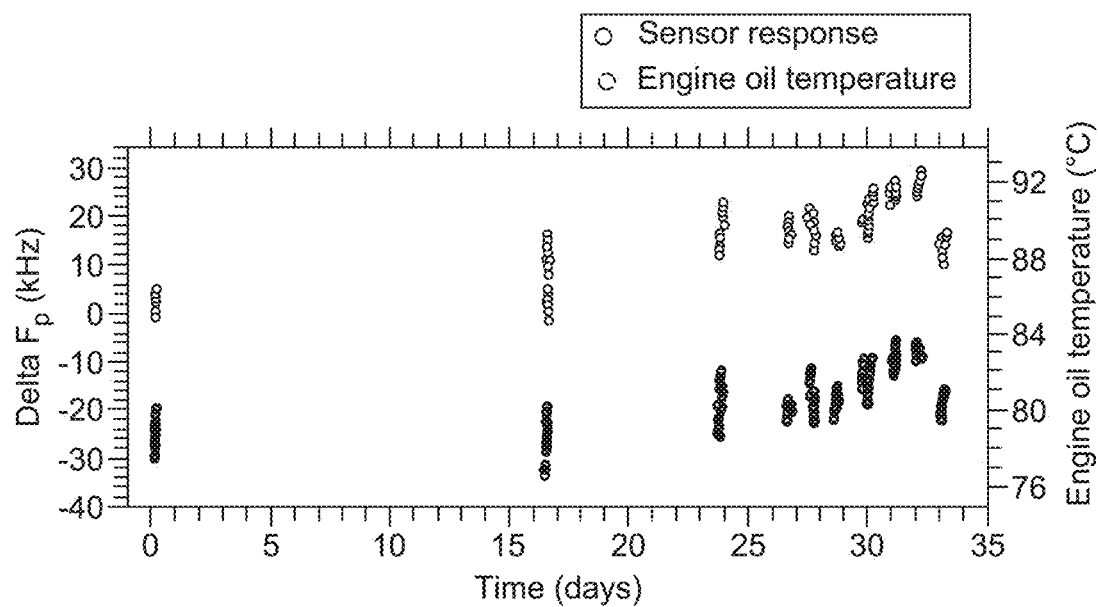
FIG. 55 shows operation of the developed resonant sensor in a single cylinder locomotive engine.
Figure 56:
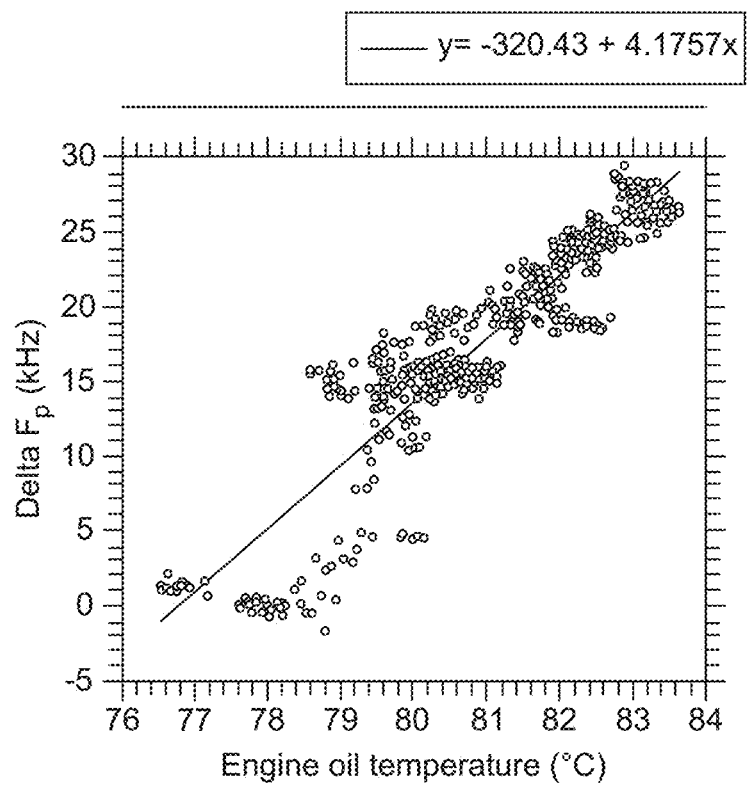
FIG. 56 shows correlation between response of the developed resonant sensor in a single cylinder locomotive engine and the temperature of oil.

The resonant sensor may be tested in a single cylinder locomotive engine test bed for about 34 days. FIG. 55 is a graph depicting results of temperature of oil and sensor response after operating the developed resonant sensor in a single cylinder locomotive engine test bed for a period of 34 days. FIG. 56 illustrates a correlation between response of the developed resonant sensor in a single cylinder locomotive engine for about 34 days and the temperature of oil.

In another example, sources of leaks in an engine may be determined by identifying dynamic signatures of the leaks, relating the identified signature with a known leak signature from a specific engine component, and determining the location of the leak based on the signature or relationship. Such approach may provide the ability for proactive maintenance, replacing reactive maintenance, and may increase the time-in-use for assets having lubrication systems or internal combustion engines.

Figure 57:
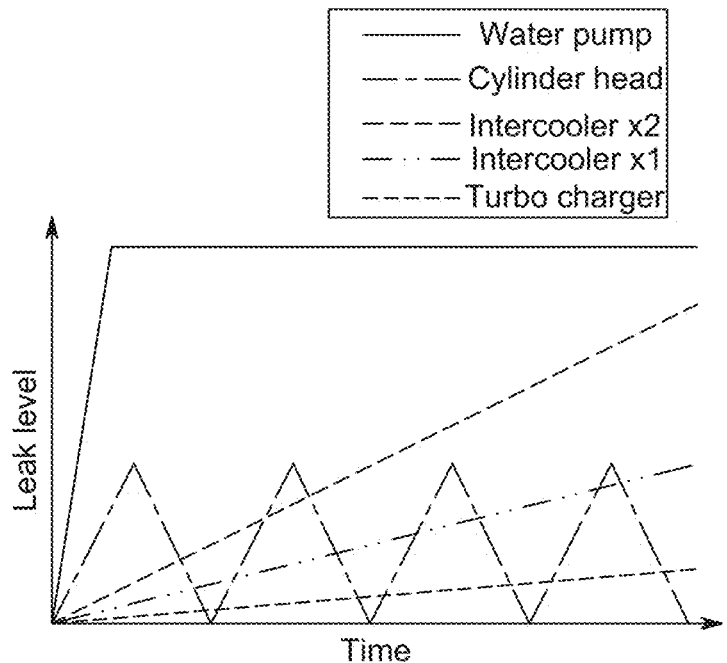
FIG. 57 is a schematic of dynamic signatures of leaks in typical components in an internal combustion engine.

Non-limiting examples of such assets with internal combustion engines include various vehicle types, each having its own set of operating parameters. Embodiments disclosed herein may provide a prognostics sensor tool for early determination of leaking components via dynamic leak signatures. These sensors may be applied in multiple locations in the engine to pinpoint the origin of leak. FIG. 57 depicts a schematic of dynamic signatures of leaks of a turbo charger (1-2 turbo chargers per engine), an intercooler (2 intercoolers per engine), a water pump (1 water pump per engine), and a cylinder head (12-16 cylinder heads per engine).

Figure 58:
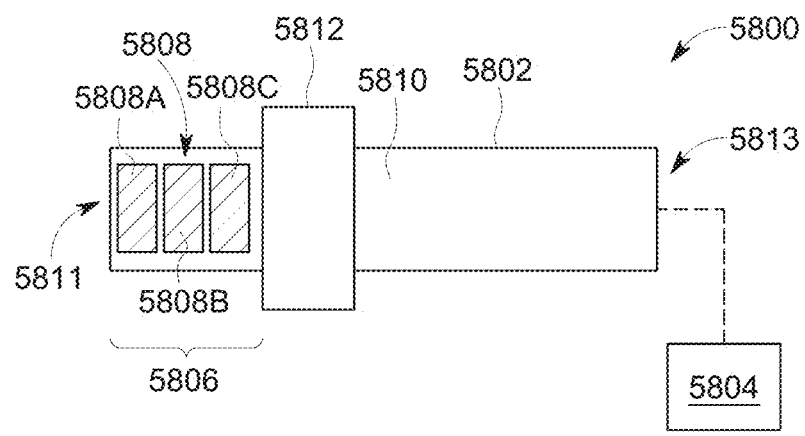
FIG. 58 is a schematic diagram of a sensing system that includes a sensor and a device body.

FIG. 58 is a schematic diagram of a sensing system 5800 that includes a sensor assembly or sensor 5802 and a device body 5804. The sensor 5802 includes a sensing region 5806 that includes multiple electrodes 5808. The sensing region 5806 is configured to be placed in operational contact with an industrial fluid of interest, such as an oil, a fuel, or a solvent. The electrodes 5808 may contact the industrial fluid directly or indirectly due to a dielectric layer or a sensing layer that may cover at least some of the electrodes 5808. Such sensing layer is applied to improve detection of water or other polar compounds in an industrial fluid. The sensing layer may be an inorganic sensing layer, unlike some conventional sensors that use polymeric sensing layers. Polymeric sensing layers in conventional resonant sensors operate by swelling and changing the resonant frequency of the sensor. In the sensor 5802, water uptake by the sensing film does not produce swelling and does not change film thickness. Rather, water uptake produces a change in the dielectric property and the capacitance of the sensing film at multiple frequencies. Unlike conventional resonant sensors, the sensor 5802 produces dielectric property changes of the sensing film at multiple frequencies (produced using components illustrated in FIGS. 19 and 20) that allows more accurate determinations of the contaminants, such as water or other polar compounds. Such improved accuracy is provided by measurements of spectral dispersion of the sensing film before and after fluid contamination. Non-limiting examples of water sorbing or sensing layers include porous silicon porous ceramic, anodized aluminum oxide, and others. The sensing region 5806 has an electrode geometry that matches the measurement needs of this sensing region 5806.

The sensor 5802 in an embodiment includes a probe body 5810 that has a shoulder 5812 extending outward from the probe body 5810 such that the shoulder 5812 has a greater radial width or diameter than the probe body 5810. The shoulder 5812 is disposed along an intermediate segment of the probe body 5810. The sensing region 5806 extends from the shoulder 5812 to a distal end 5811 of the probe body 5810. A proximal end 5813 of the probe body 5810 is operably coupled to the device body 5804. The electrodes 5808 are disposed on the sensing region 5806 at different distances relative to the shoulder 5812 such that the electrodes 5808 extend different depths into the industrial fluid. In an embodiment, at least two of the electrodes 5808 operate at one or more high frequencies and at least one of the electrodes 5808 (that is different than the electrodes 5808 that operate at high frequencies) operates at one or more low frequencies.

For example, the sensor 5802 in the illustrated embodiment includes multiple sensing sub-regions that each includes one or more electrodes 5808 disposed therein. The sub-regions with electrodes each contain electrode structures where these structures are two-electrode structures or four-electrode structures. The sensing sub-regions include a distal sensing sub-region 5808A, an intermediate sensing sub-region 5808B, and a proximal sensing sub-region 5808C. The electrodes 5808 in the different intermediate sub-region 5808B are located between the distal sub-region 5808A and the proximal sub-region 5808C. The electrodes 5808 in the different sub-regions 5808A-C may operate at different frequencies and/or frequency ranges relative to one another. Some of the electrodes 5808 in the different sub-regions 5808A-C may be used for contaminant (such as water) concentration detection, while other electrodes 5808 in the different sub-regions 5808A-C may be used for test fluid aging detection. As an alternative to water, some examples of other contaminants that may be detected by the sensing system 5800 include fuel, dust, and other external contaminants. The electrodes 5808 in the different sub-regions 5808A-C may have differing electrode spacings between adjacent electrodes 5808.

The distal sensing sub-region 5808A in an embodiment is covered by the sensing layer. The distal sensing sub-region 5808A may be configured to measure low concentration water or other contaminant leaks in oil. Each electrode 5808 in the distal sensing sub-region 5808A may be an interdigitated electrode that has an area in the range from 0.1 mm² to 100 mm². The electrode spacing for the electrodes 5808 in the sub-region 5808A may be relatively small, such as in the range from 0.1 μm to 10 μm. For example, the electrodes 5808 may have an area of 2 cm×2 cm with an electrode spacing of 0.15 mm. The electrodes 5808 may resonate at around 50 MHz in air. The electrodes 5808 in the distal sub-region 5808A may be operated at relatively high frequencies and/or frequency ranges compared to the electrodes 5808 in the intermediate and/or proximal sub-regions 5808B, 5808C.

The electrodes 5808 in the intermediate sensing sub-region 5808B are located more proximate to the device body 5804 than the distal sensing sub-region 5808A. The intermediate sensing sub-region 5808B is provided for preferential measurements of leaks of nonpolar external contaminants and fluid aging detection. These electrodes 5808 in an embodiment are not coated with a sensing layer. The electrodes 5808 in the intermediate sub-region 5808B may have relatively small spacing in the range from 0.1 μm to 10 μm. The electrodes 5808 of the intermediate sub-region 5808B may be operated at relatively high frequencies and/or frequency ranges compared to the electrodes 5808 in the proximal sub-region 5808C.

The electrodes 5808 in the proximal sensing sub-region 5808C are disposed more proximate to the device body 5804 than the sensing sub-regions 5808A and 5808B. The electrodes 5808 in the sub-region 5808C are provided for preferential measurements of fluid aging detection. These electrodes are not coated with a sensing layer and can have relatively large spacing in the range from 1 μm to 5000 μm. The electrodes 5808 of the proximal sub-region 5808B may be operated at relatively lower frequencies and/or frequency ranges compared to the electrodes 5808 in the distal and/or intermediate sub-regions 5808A, 5808B.

With additional reference to FIGS. 19 and 20, the sensor 5802 includes at least one resonant inductor-capacitor-resistor (LCR) circuit having one or more tuning elements 1942. The one or more resonant LCR circuits are configured to generate an electrical stimulus having a spectral frequency range. The electrical stimulus is applied to the industrial fluid at the sensing region 5806 via the electrodes 5808.

The sensor 5802 is operably coupled to the device body 5804, such as via a mechanical fixed connection, a wired connection, or a wireless electrical connection. The device body 5804 may be the device body 315 shown in FIG. 7. For example, the sensor 5802 may include a communication unit (e.g., a transceiver or discrete transmitter and receiver) that wirelessly transmits electrical signals to the device body 5804. The device body 5804 includes one or more processors, which may be or include the processing unit 306 shown in FIG. 7. The one or more processors are configured to receive an electrical signal from the sensor 5802 that is representative of a resonant spectral response (or resonant impedance spectra) of the sensing region in operational contact with the industrial fluid in response to the electrical stimulus being applied to the industrial fluid.

The one or more processors are configured to analyze the resonant spectral response and determine both a water concentration in the industrial fluid and an aging level of the industrial fluid based on the analyzed resonant spectral response. The resonant spectral response is indicative of a dielectric dispersion profile of the industrial fluid over the spectra frequency range of the electrical stimulus. The one or more processors may be configured to analyze the resonant spectral response by extracting complex resonance parameters from the resonant spectral response. The complex resonance parameters are described with reference to FIGS. 23 and 29. The concentration of water or other external contaminants in the industrial fluid and the aging level of the fluid may be determined by comparing the extracted complex resonance parameters to known resonance parameters associated with various water concentrations of the industrial fluid and various aging levels of the industrial fluid. The comparison may include classifying the extracted resonance parameters using an earlier built classification model (as described in steps 2870 and 2872 of FIG. 29) and quantitating the extracted resonance parameters using an earlier built classification model (as described in steps 2880 and 2882 of FIG. 29).

In an embodiment, the sensor 5802 includes multiple resonant LCR circuits. Each resonant LCR circuit has a different resonant frequency. The electrical stimulus applied to the industrial fluid is generated over a spectral frequency range that includes or incorporates the resonant frequencies of the resonant LCR circuits such that the impedance spectral response is measured over the resonant frequencies. Optionally, the sensor 5802 may include a multiplexer 1944 (shown in FIG. 19) that is configured to individually control the resonant LCR circuits to tune the electrical stimulus that is applied to the industrial fluid. The multiple resonant frequencies allow the sensing system 5800 to detect multiple variables or properties of the industrial fluid, such as the concentration of water and the age of the fluid. For example, the sensing system 5800 may include four resonant frequencies.

The sensor 5802 may also include data acquisition circuitry (not shown) which may be similar to the data acquisition circuitry 1716 shown in FIGS. 17 and 18. The data acquisition circuitry is configured to generate an electrical signal representative of the measured resonant impedance spectra. The electrical signal may be transmitted to a processing device, such as the device body 5804, for analysis of the resonant impedance spectra to determine one or more properties of the industrial fluid. The one or more properties in an exemplary embodiment are both a concentration of water (or another external contaminant) in the fluid and an aging level of the fluid.

The analysis of the resonant impedance spectra may be performed by comparing the extracting resonance parameters from the measured resonant impedance spectra from the electrodes in each of the sensing sub-regions 5808A, 5808B, and 5808C to known resonance parameters of the same or a similar fluid at various defined concentrations of water in the fluid or other external contaminant and at various age levels of the fluid. In one example in which water is the external contaminant, the tested fluid of interest may be determined to have a given water concentration and a given age level responsive to the measured set of resonance parameters matching a set of known resonance parameters associated with the given water concentration and the given age level to a greater extent than the measured set of resonance parameters matches other sets of known resonance parameters associated with other concentrations of water and/or age levels. Statistical methods may be used to compare and "match" the measured resonance parameters to the known resonance parameters. The statistical method used may be a regression analysis, such as a linear regression, a nonlinear regression, or the like. In another example, a series of experiments may be performed using a single sensor to determine the measured resonance parameters of a resonant impedance spectral response of the sensor in a given industrial fluid at various concentrations of water or other external contaminant in the fluid and at various age levels of the fluid, which are the two or more variables that change across the series of experiments. The measured resonance parameters for the series of experiments may be plotted as data points on a graph, and may be used to develop a quantitative model that is used to predict the water or other external contaminant concentration and the age level of monitored fluids (where the water concentration or other external contaminant and the age are unknown). The quantitative model may be a transfer function for the sensing region 5808 broadly or for the individual sensing sub-regions 5808A, 5808B, and 5808C. Thus, measured resonance parameters from a resonance impedance spectral response may be input as variables into the quantitative model to predict water or other external contaminant concentration and aging level of the tested fluid.

The determination of the contaminant concentration in and/or age of the fluid of interest may be performed by establishing correlations between the spectral responses of the sensing sub-regions 5808A, 5808B, and 5808C at multiple frequencies across the dispersion profiles of the contaminant concentration and/or the age of the fluid and the levels of the contaminant concentration and/or the age of the fluid as determined initially via independent reference laboratory methods. Once these correlations (also known as transfer functions) are established, they are further utilized to predict the unknown measured concentrations. Such predictions may be performed by having the measured signals from the sensing sub-regions 5808A, 5808B, and 5808C at multiple frequencies across the dispersion profiles of the contaminant concentration and/or the age of the fluid, entering the values of these signals into the transfer functions or a single function, and obtaining the predicted values of the contaminant concentration and/or the age of the fluid. Depending on the transfer functions, one or more contaminants may be quantified from the measured signals from the sensing sub-regions 5808A, 5808B, and 5808C at multiple frequencies across the dispersion profiles of the contaminants concentration and/or the age of the fluid.

Figure 59:
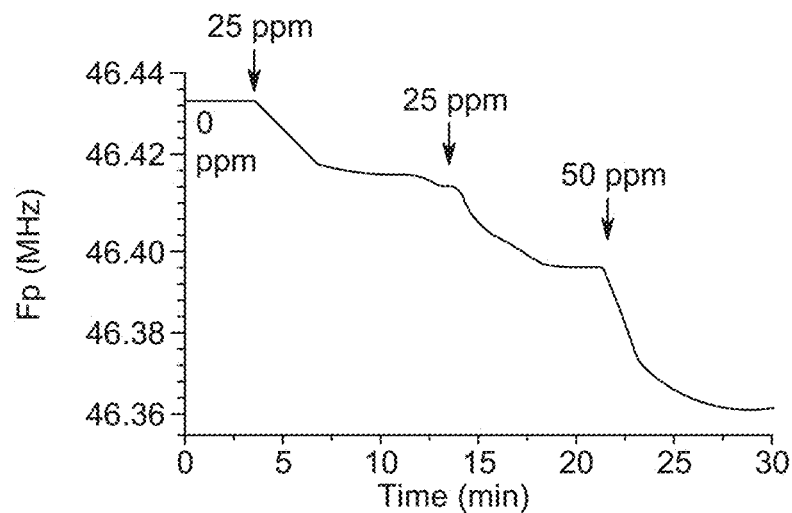
FIG. 59 depicts responses of a developed resonant sensor to water leaks into engine oil at levels of 25 ppm, 25 ppm, and 50 ppm each.

The concentrations of water or other external contaminants detected by the sensor 5802 may be down to 1 ppm. FIG. 59 depicts responses of this developed resonant sensor 5802 to water leaks into engine oil at levels of 25 ppm, 25 ppm, and 50 ppm each. The water levels indicate additions of water, so the second addition of water at 25 ppm results in doubling the amount of water added to the sample fluid, and the third leak level results in four times the concentration of water relative to the first leak level. The data in FIG. 59 illustrates that this sensor 5802 may detect the water leaks at the lowest tested level of 25 ppm with high signal-to-noise ratio quality, resulting in the ability to resolve 1 ppm of water leak with a signal-to-noise (S/N) ratio of 3.

Figure 60:
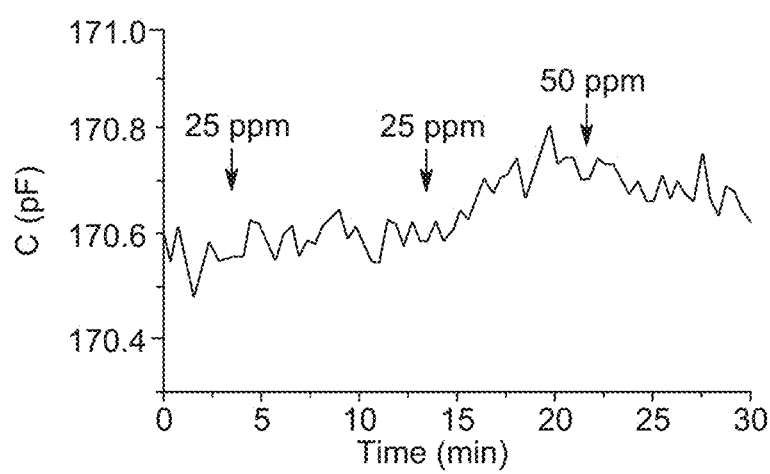
FIG. 60 depicts the response of a reference capacitance sensor to water leaks into engine oil at levels of 25 ppm, 25 ppm, and 50 ppm each.

The performance of this developed resonant sensor may be compared with the performance of a standard non-resonant capacitance sensor that is used as a reference capacitance sensor. The comparison may be performed by having both sensors in the same circulating-oil loop where water leaks may be introduced and presented to both sensors. Water leak levels may be 25 ppm, 25 ppm, and 50 ppm each. FIG. 60 depicts the response of the reference capacitance sensor to water leaks into engine oil at levels of 25 ppm, 25 ppm, and 50 ppm each. This figure illustrates that the reference capacitance sensor did not show an appreciable signal change due to noise, indicating an inability to distinguish among the different concentrations of water leaks.

Figure 61:
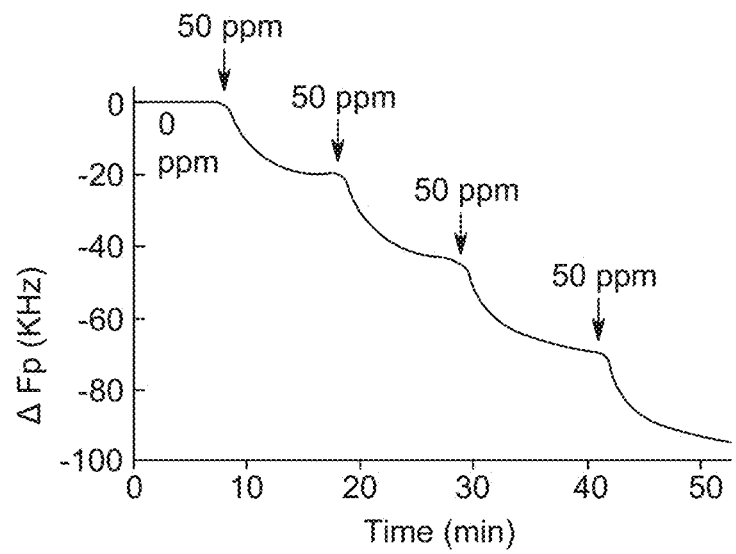
FIG. 61 shows the response of a multivariable resonant sensor to water leaks into engine oil responsive to the 50 ppm steps.
Figure 62:
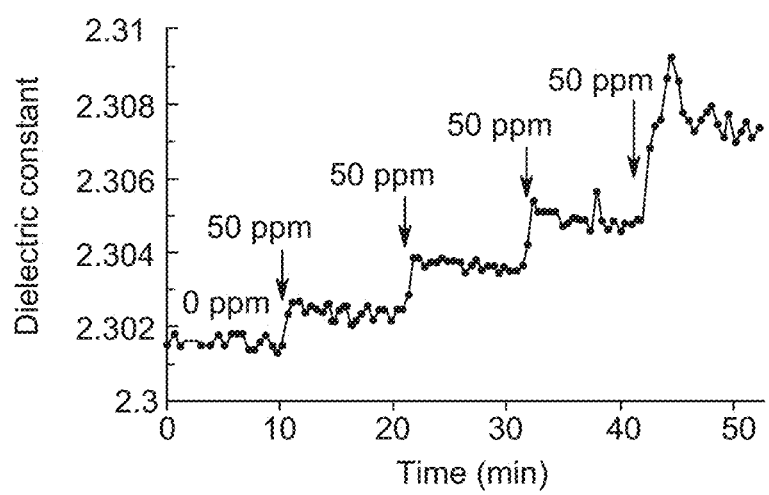
FIG. 62 depicts the response of a control tuning fork sensor to water leaks into engine oil at 50 ppm steps.

Benchmarking of the multivariable resonant sensor 5802 may be performed in comparison to a control or reference tuning fork sensor for quantitation of water leaks into oil. The tuning fork sensor is a mechanical resonator sensor that measures viscosity, density and dielectric constant of a test fluid. The benchmarking was performed by having both sensors in the same circulating-oil loop where water leaks were introduced and presented to both sensors. Water leaks levels were induced at 50-ppm steps. FIG. 61 shows the response of the multivariable resonant sensor to water leaks into engine oil responsive to the 50 ppm steps. FIG. 61 indicates that the sensor 5802 detects water leaks with a high signal-to-noise ratio. FIG. 62 depicts the response of the control tuning fork sensor to water leaks into engine oil at 50 ppm steps. The data in FIG. 62 demonstrates a significantly lower signal-to-noise ratio for the control tuning fork sensor relative to the sensor 5802.

In an experimental example, quantitation of water leaks at various stages of oil aging was performed using the sensor of one or more of the embodiments disclosed herein. The industrial fluid was automotive oil 10 W-30. Water was added into the oil at different levels ranging from 25 parts per million (ppm) to 900 ppm when oil had three different aging levels. The aging levels were fresh (0% aging), old (100% aging), and intermediate (50% aging). The fresh oil indicates new oil, the old oil indicates oil with a mileage of 5000 miles in an automotive, and the intermediate oil is a 50/50 ratio of fresh and old oil. The oil may be considered new or fresh at or proximate to a beginning of a recommended fluid life of the oil, the oil may be considered old at or proximate to an end of the recommended fluid life of the oil, and the oil may be considered intermediate at or proximate to the middle of the recommended fluid life. For example, for an oil with a recommended fluid life of 5000 miles in a vehicle, the oil may be considered as new or fresh during the first 10% of the recommended fluid life (e.g., during roughly the first 500 miles), the oil may be considered as old for the last 10% of the recommended life (e.g., during roughly the final 500 miles before reaching 5000 miles) and during any additional miles beyond the recommended life, and the oil may be considered as intermediate for the middle 10% of the recommended life (e.g., during the period roughly between miles 2250 and 2750).

Figure 63A:
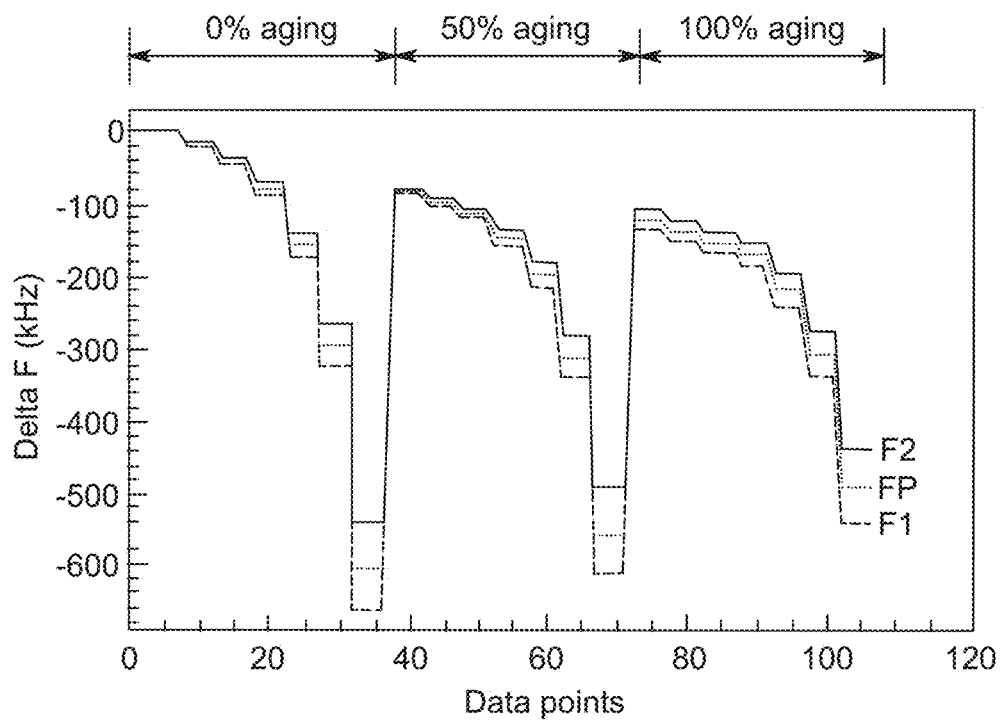
FIGS. 63A-63B are plots depicting raw responses of resonance parameters of a resonant impedance spectra measured by the multivariable resonant sensor.
Figure 63B:
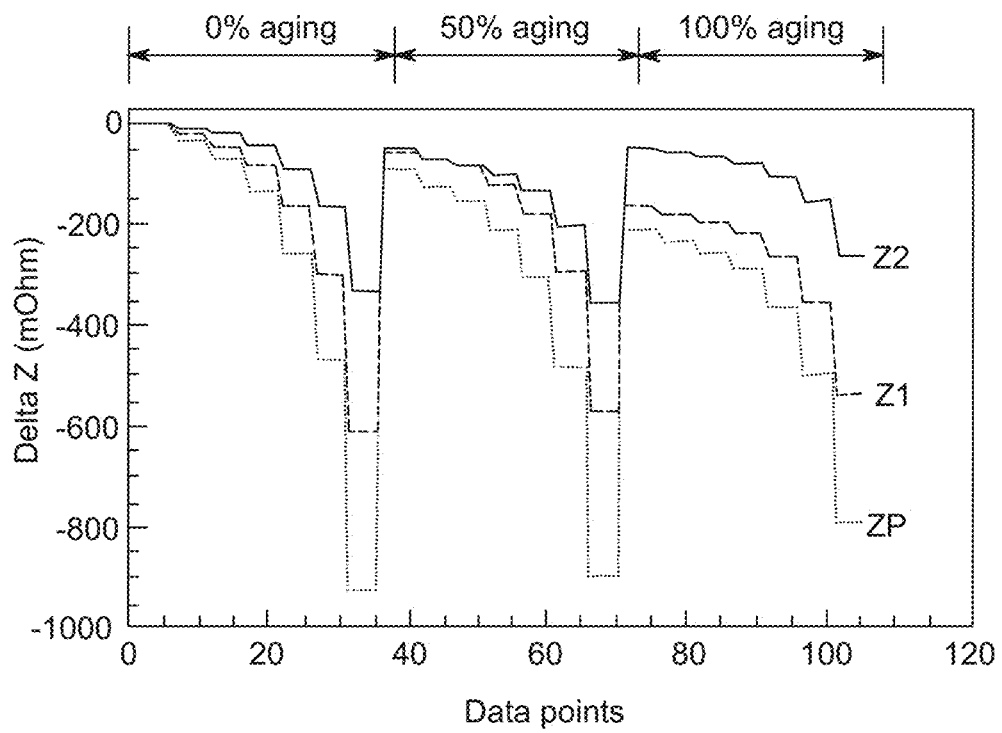
Figure 64:
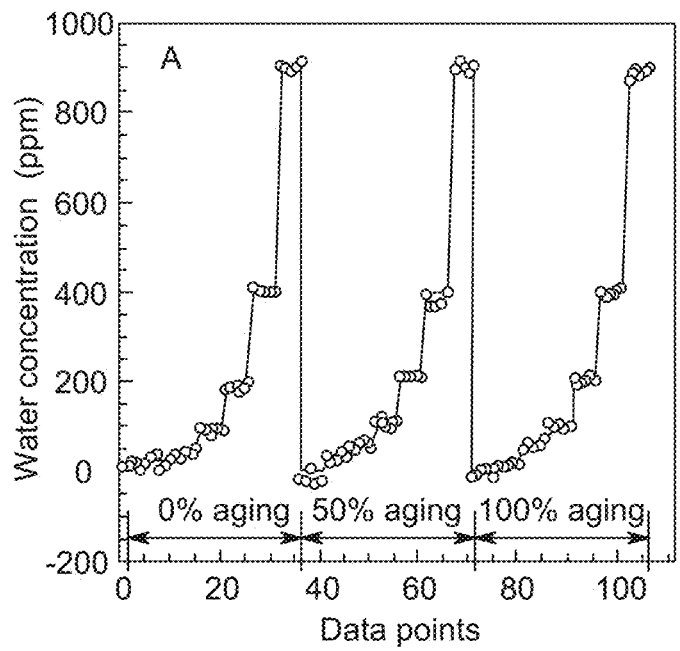
FIG. 64 shows the results of predicted versus actual concentrations for individual different levels of aging.
Figure 65:
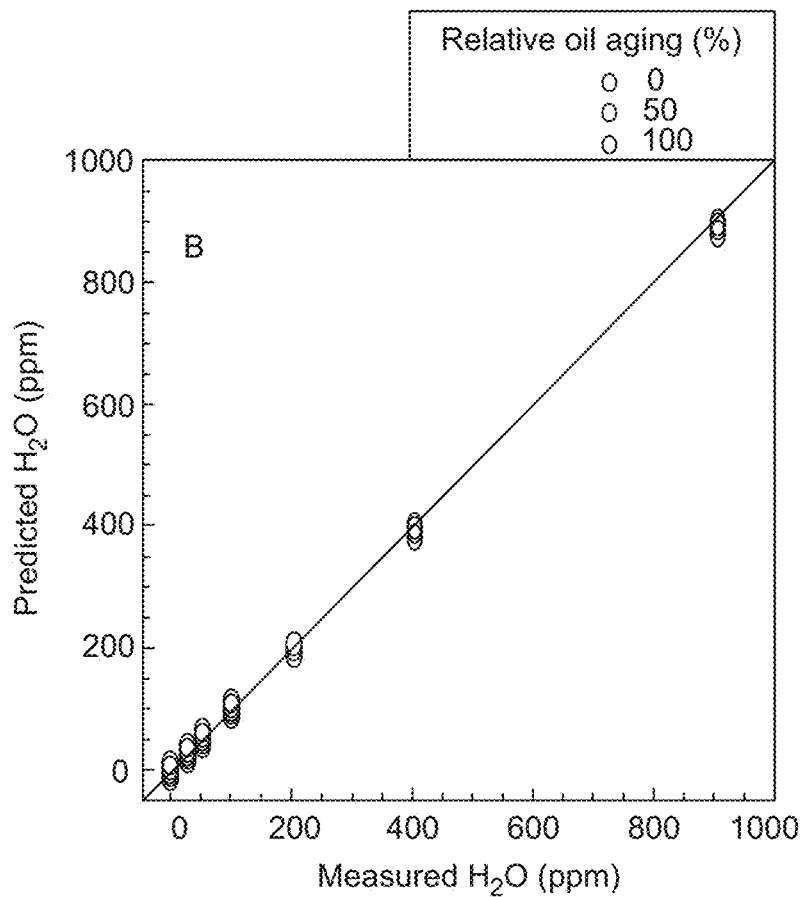
FIG. 65 shows a correlation plot between the actual and predicted water concentrations for three levels of oil aging (e.g., beginning of a recommended oil life, middle of the recommended oil life, or end of the recommended oil life).
Figure 66:
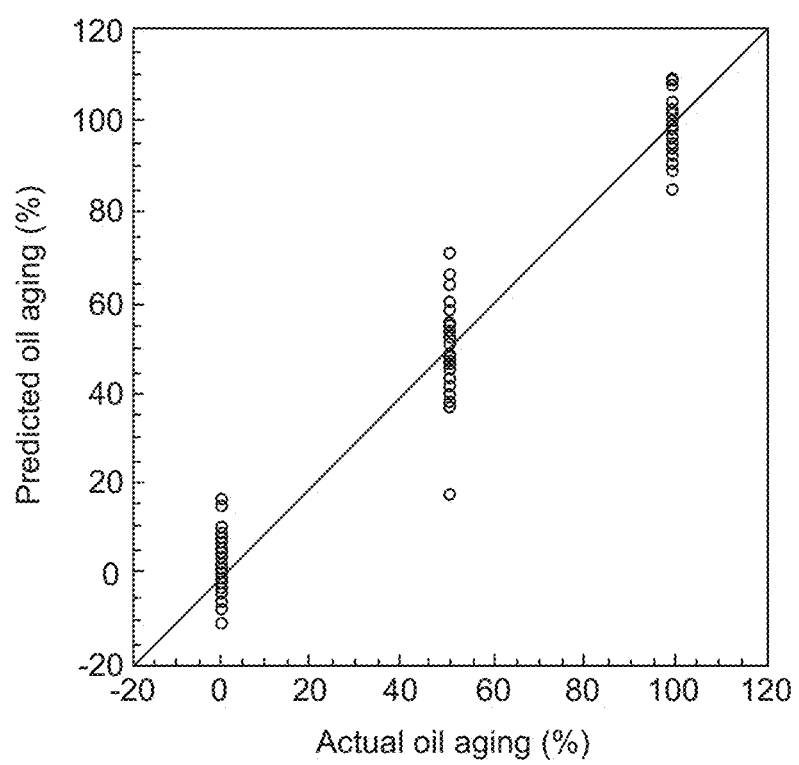
FIG. 66 is a correlation plot between actual and predicted oil aging using the multivariable resonant sensor.

FIGS. 63A and 63B are plots depicting the raw responses of the resonance parameters (e.g., F1, F2, and Fp as in FIG. 63A and Z1, Z2, and Zp as in FIG. 63B) of the resonant impedance spectra measured by the sensor 5802 (shown in FIG. 58). As shown in FIGS. 63A-B, the sensor 5802 responds differently to the water additions depending on the aging levels of the oil samples. A quadratic transfer function was developed based on the raw data obtained in the experiment in order to predict water leaks into the oil. The results of the predicted versus actual concentrations are presented in FIGS. 64 and 65. FIG. 64 shows the results of the predicted versus actual concentrations for individual different levels of aging, and FIG. 65 shows a correlation plot between the actual and predicted water concentrations for the three levels of oil aging (e.g., beginning of a recommended oil life, middle of the recommended oil life, or end of the recommended oil life). The solid plot line represents a quantitative curve or model developed based on a series of experiments using known water concentrations in the oil and known age levels of the oil. The circular data points represent predicted water concentrations and age levels based on resonance parameters extracted or calculated from measured resonant impedance spectral responses of the sensor in contact with fluids of unknown water concentration and unknown age. These results demonstrate that the single developed multivariable sensor discriminates well between water leaks and oil aging and provides the ability to predict water concentrations. FIG. 66 is a correlation plot between actual and predicted oil aging using the sensor, which indicates that the single developed multivariable sensor also discriminates well between oil aging levels and provides the ability to predict oil aging. As a result, the single sensor is able to predict with significant accuracy both the concentration of water in the industrial fluid and the age of the fluid (relative to a recommended fluid life) without the need for multiple sensors to obtain such information.

Figure 67:
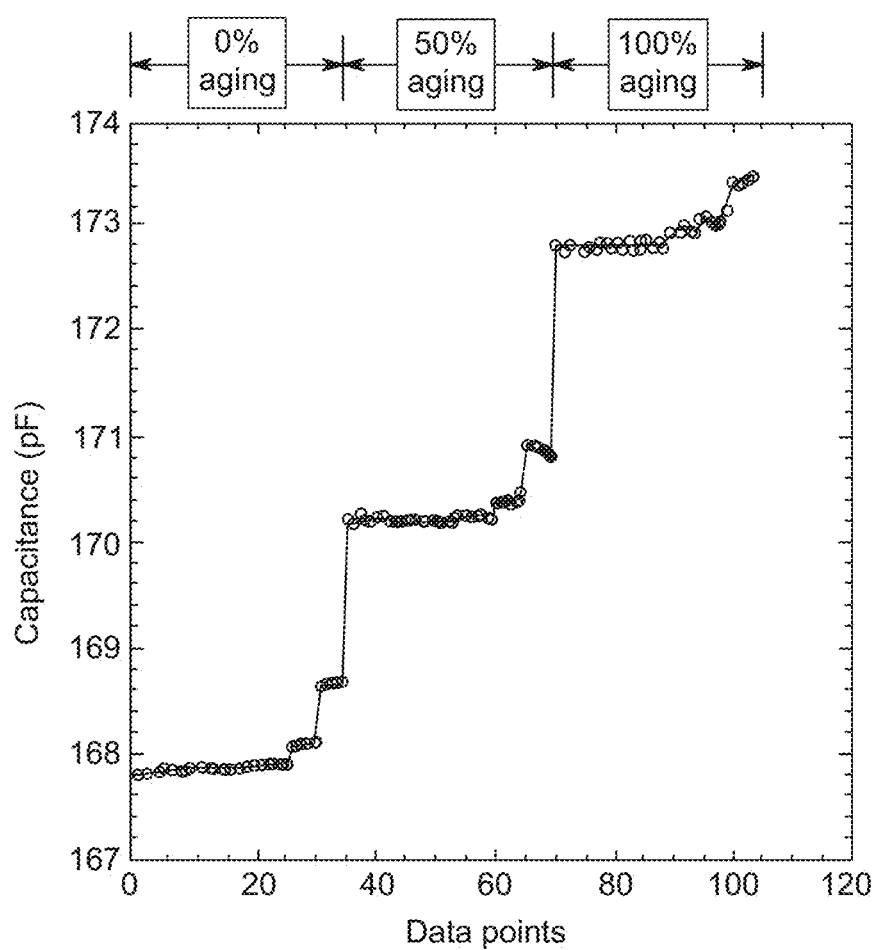
FIG. 67 depicts raw responses of a conventional capacitance sensor to water additions into differently aged oil samples.
Figure 68:
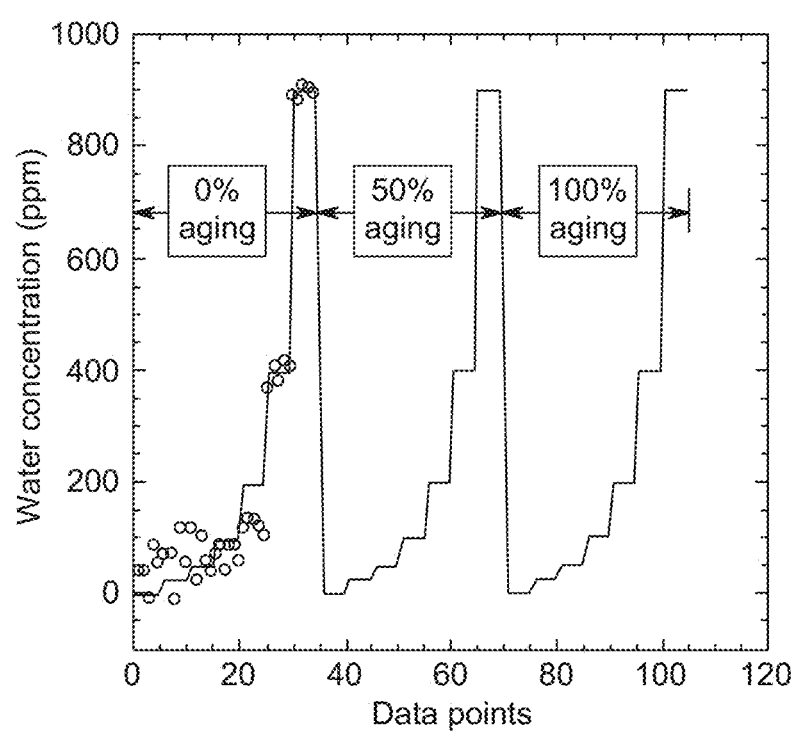
FIG. 68 plots results of predicted vs. actual concentrations of water concentrations for individual different levels of aging measured with a conventional capacitance sensor.

A similar experiment was performed using a conventional capacitance sensor using the same oil and the same water concentrations and aging levels. The results of the experiment indicate that the conventional capacitance sensor does not discriminate between water leaks and oil aging. The conventional capacitance sensor is not able to predict water concentrations at more than one aging level. Measurements were performed simultaneously with the conventional capacitance sensor and the multivariable resonant sensor (e.g., such as the sensor 5802 shown in FIG. 58). FIG. 67 depicts the raw response of the conventional capacitance sensor to water additions into differently aged oil samples. The capacitance sensor responded significantly to differently aged oil samples and less to the water additions into oil. A quadratic transfer function was developed to predict water leaks into fresh oil. Results of the predicted vs actual concentrations of water concentrations for individual different levels of aging measured with a conventional capacitance sensor are presented in FIG. 68. These results demonstrate that a conventional capacitance sensor does not discriminate between water leaks and oil aging and only provides the ability to predict water concentrations in fresh oil.

Figure 69A:
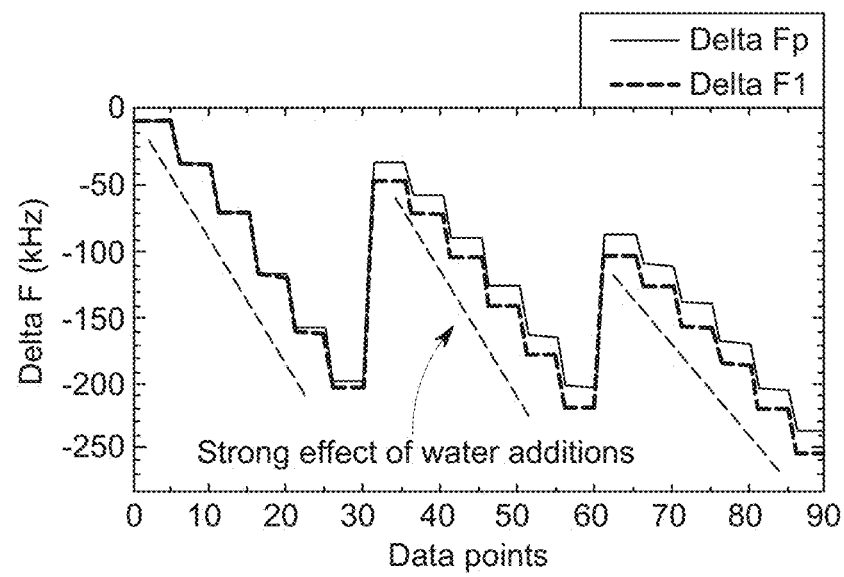
FIGS. 69A-69B depict raw responses of Fp, F1, F2 (FIG. 69A) and Zp, Z1, Z2 (FIG. 69B) of the multivariable resonant sensor to water additions into differently aged oil samples.
Figure 69B:
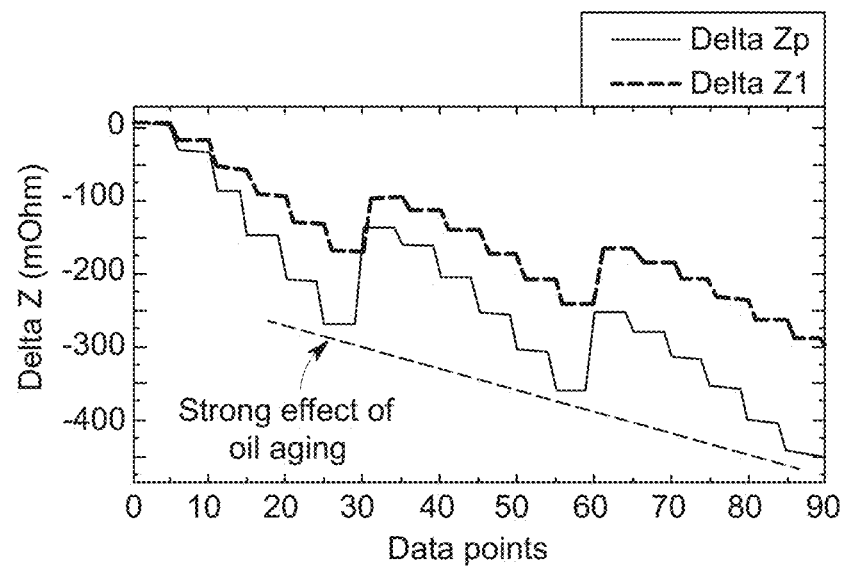

The performance of the developed multivariable resonant sensor was further benchmarked with the tuning fork sensor in quantitation of water leaks into oil at various stages of oil aging at one temperature. The employed model oil was automotive oil 10 W-30 (AutoZone). Water was spiked into oil at 50-ppm levels providing steps of 50, 100, 150, 200, and 250 ppm of total water additions when oil had three levels of aging such as 50, 70, and 100%. FIGS. 69A and 69B depict raw responses of $F_p$, $F_1$, $F_2$ (FIG. 69A) and $Z_p$, $Z_1$, $Z_2$ (FIG. 69B) of the multivariable resonant sensor to water additions into differently aged oil samples. The data points corresponding to three levels of aging were from 0 to 30 (aging 50%), from 31 to 60 (aging 70%), and from 61 to 90 (aging 100%). The mileage for aged oil was 5000 miles. The 0% aging was fresh oil; the 100% was oil aged at 5000 miles; the 50% and 70% were 50/50 and 70/30 ratios of fresh and aged oil. The multivariable resonant sensor responded differently to the water additions into differently aged oil samples.

Figure 70A:
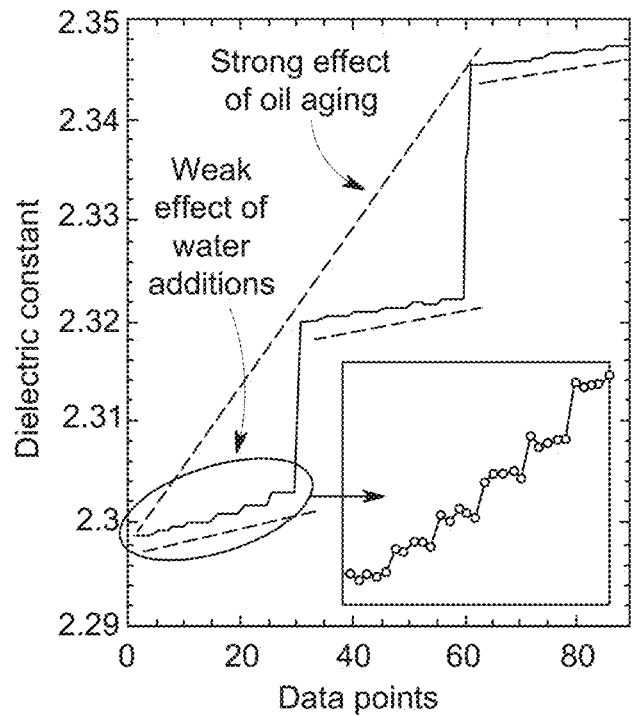
FIGS. 70A-C depict raw dielectric constant, density, and viscosity outputs, respectively, of a tuning fork sensor.
Figure 70B:
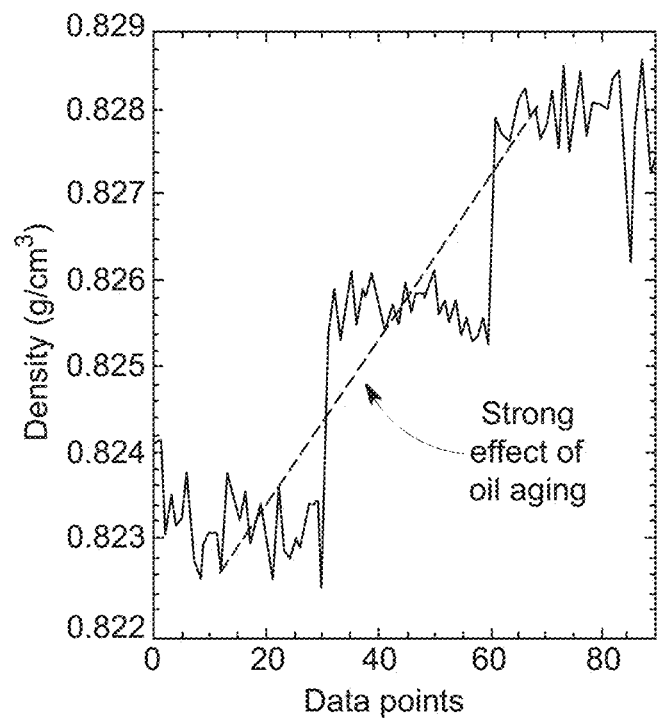
Figure 70C:
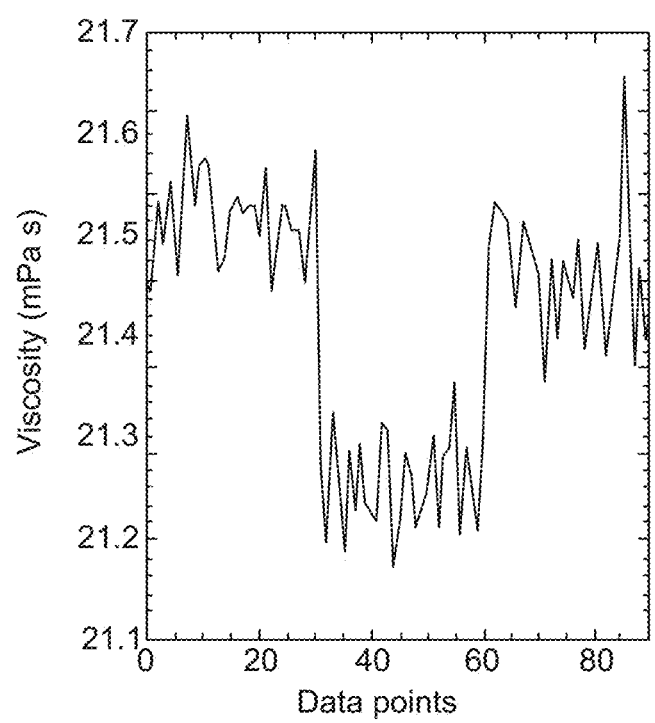

As a benchmark, quantitation of water leaks at various stages of oil aging was performed using the tuning fork. Measurements were performed simultaneously with the tuning fork and the multivariable resonant sensor (e.g., such as the sensor 5802 shown in FIG. 58). FIGS. 70A-C depict the raw dielectric constant, density, and viscosity outputs, respectively, of the tuning fork sensor. The tuning fork sensor responded strongly to differently aged oil samples and relatively much less to the water additions into oil as depicted in FIG. 70A. Response of the tuning fork to oil aging was dominating over the response to water leaks. In particular, dielectric constant response (FIG. 70A) showed strong response to aging (signal jumps at 30 and 60 points) and only relatively small effect of water leaks (small slopes of response over 0-30, 31-60, and 61-90 data points. The density (FIG. 70B) and viscosity (FIG. 70C) outputs showed only responses to aging.

Figure 71:
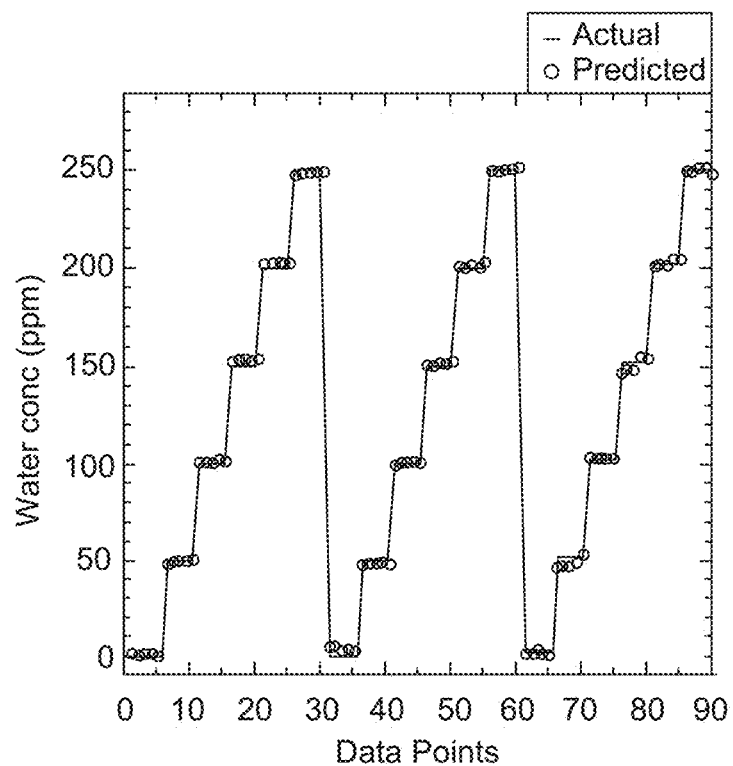
FIG. 71 shows the results of predicted and actual concentrations of water leaks into oil for the multivariable resonant sensor at different oil aging levels.
Figure 72:
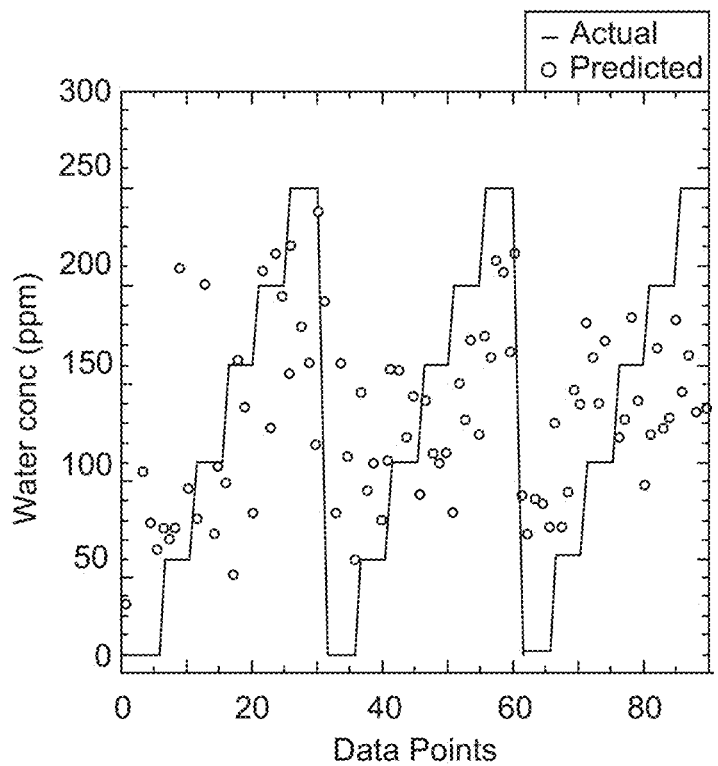
FIG. 72 shows the results of predicted and actual concentrations of water leaks into oil for the conventional tuning fork sensor at different oil aging levels.

Water leaks and oil aging levels were attempted to be quantified using the multivariable resonant sensor (e.g., the sensor 5802 shown in FIG. 58) and the conventional tuning fork sensor. Transfer functions were constructed for each sensor based on their respective outputs. The transfer functions were used to predict water leaks and oil aging levels. The residual prediction errors were evaluated by subtracting actual and predicted values of water leaks and oil aging. FIG. 71 shows the results of predicted and actual concentrations of water leaks into oil for the multivariable resonant sensor at different oil aging levels. These results demonstrate that a single developed multivariable sensor provided the ability to predict water concentrations, as illustrated by the close positioning of predicted values (open circles) to the actual values (solid line) in FIG. 71. FIG. 72 shows the results of predicted and actual concentrations of water leaks into oil for the conventional tuning fork sensor at different oil aging levels. These results demonstrate that the tuning fork sensor was unable to predict water concentrations in oil of different aging levels, as illustrated by the seemingly random scatter of predicted values (open circles) to the actual values (solid line) in FIG. 72.

To determine positions of resonances in the multi-resonant sensor, dielectric properties of fresh and aged oil samples in a broad range of frequencies from 100 Hz to 10 MHz were measured using a dielectric spectroscopy setup consisting of an Agilent 4294A precision impedance analyzer and an Agilent 16452A liquid test fixture. Dielectric spectra were transferred from the 4294A impedance analyzer to a data processing computer using a 4294A data transfer program available from Agilent as a Microsoft Excel macro and was analyzed as described in the 16452A test fixture manual to obtain the real and imaginary parts of the complex dielectric constant ($\varepsilon'$ and $\varepsilon''$, respectively). These measurements were used in the determination of the spectral dispersion properties of oils and allowed the further downselection of operating frequencies for the multi-resonance sensor operation.

Figure 73A:
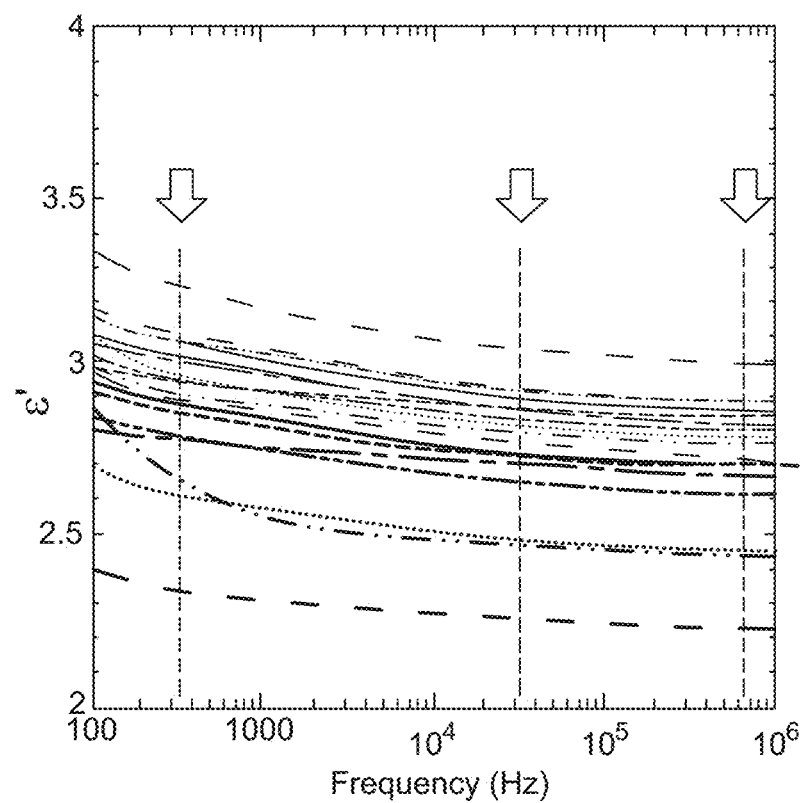
FIGS. 73A-B depict an application of the multiresonant sensor system for the correction for oil aging that shows one example of the selection of operating frequencies of the multiresonant sensor system across the spectral dispersion of locomotive oil.
Figure 73B:
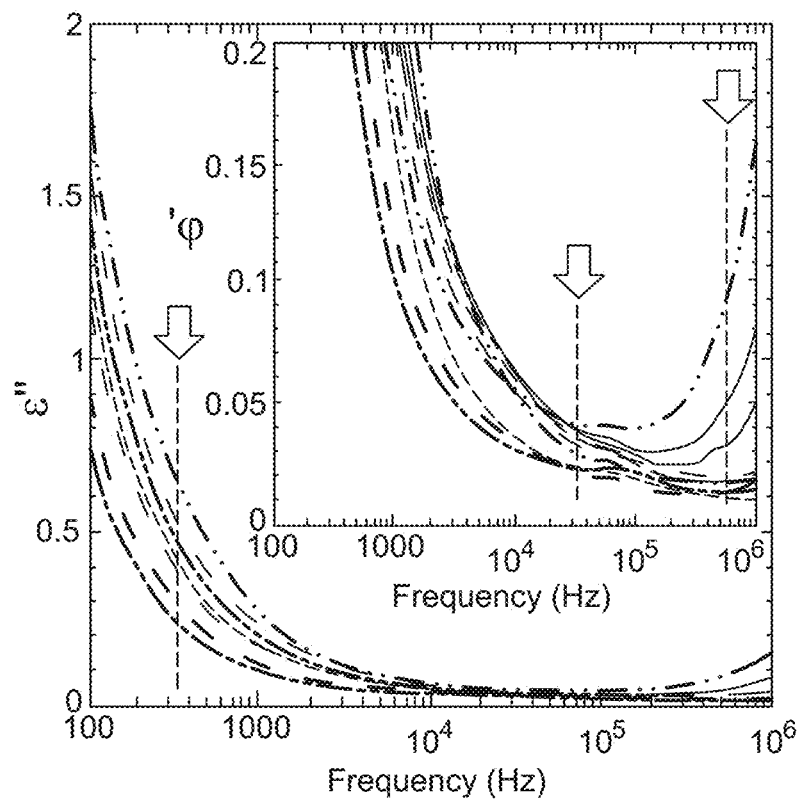
Figure 74A:
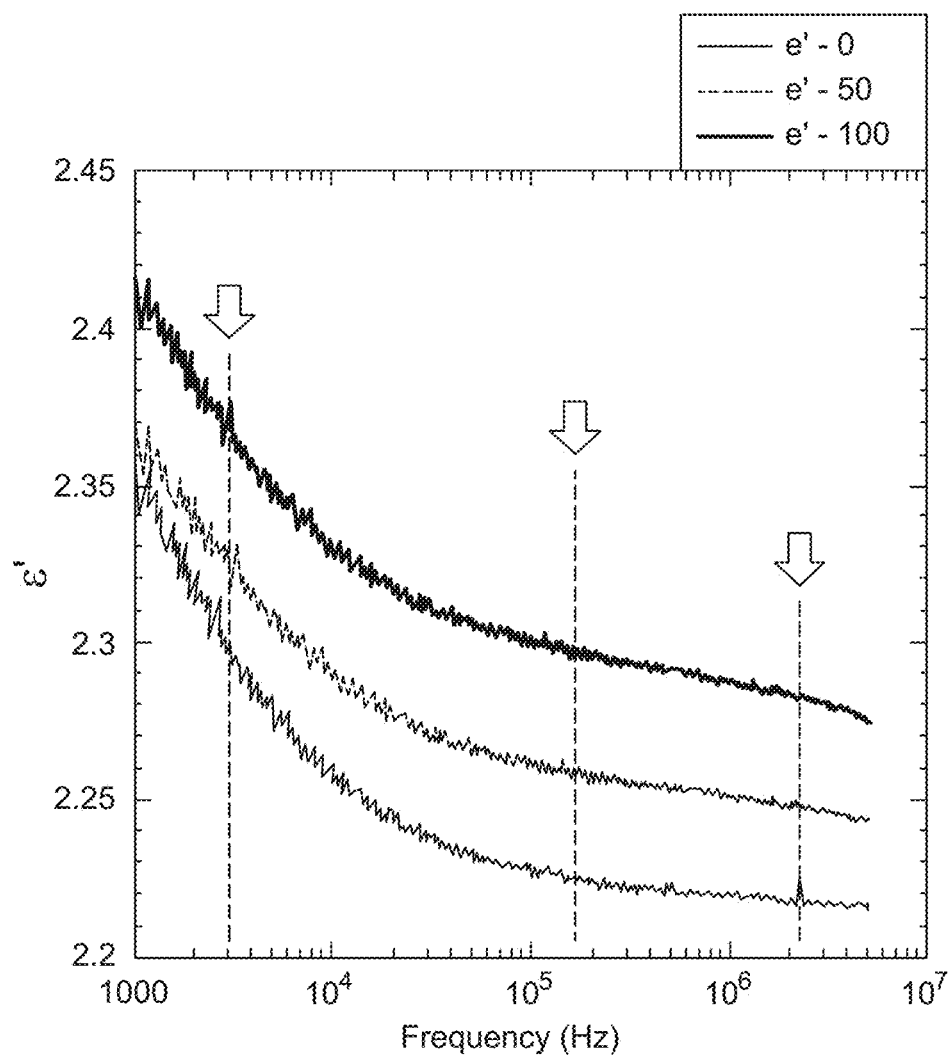
FIGS. 74A-B depict the real and the imaginary portions of the complex permittivity of the employed model automotive oil 10 W-30 with three levels of aging such as 0, 50, and 100%.
Figure 74B:
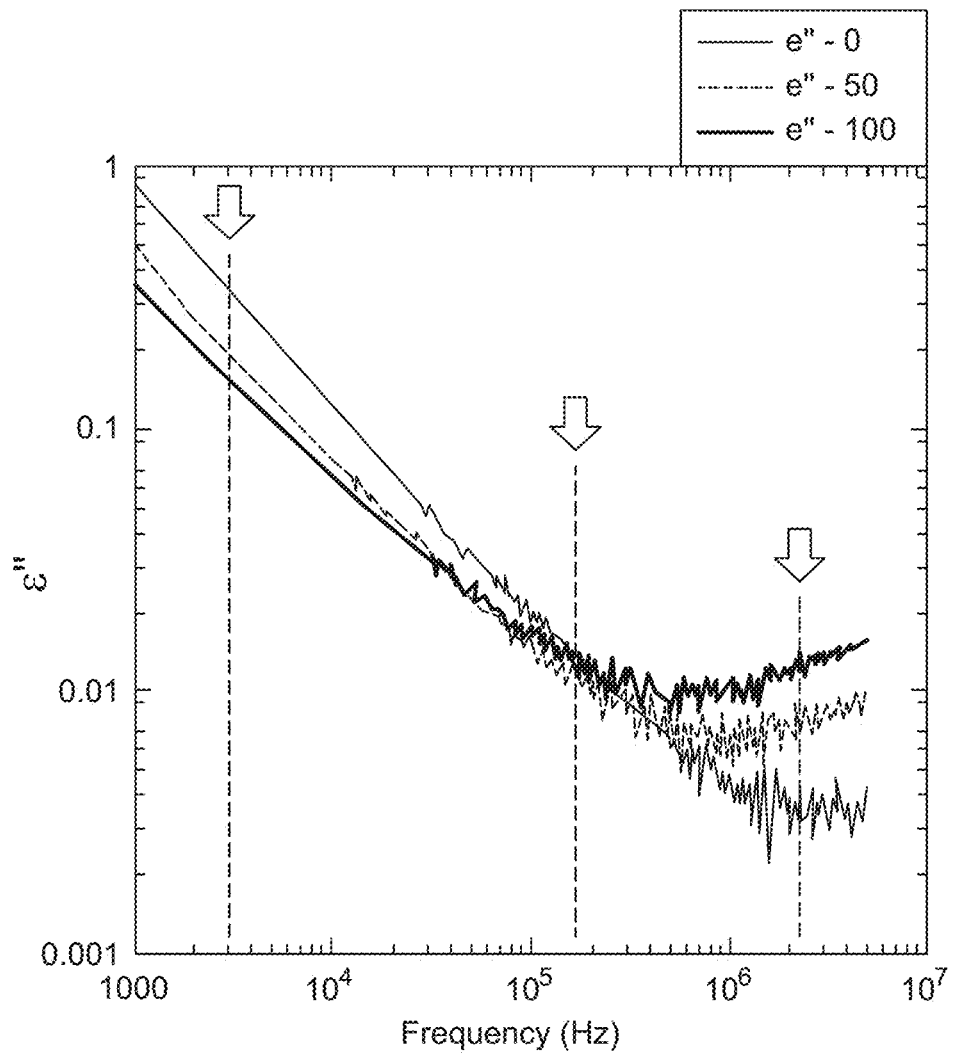

FIGS. 73A and 73B depict an application of the multi-resonant sensor system for the correction for oil aging that shows one example of the selection of operating frequencies of the multiresonant sensor system across the spectral dispersions shown for a range of fresh and used (aged) locomotive oils. FIG. 73A is the real part ($\varepsilon'$) and FIG. 73B is the imaginary part ($\varepsilon''$) of the complex dielectric constant of a locomotive oil. Arrows and dotted lines indicate initially selected regions for the multiresonant sensor operation. The real and the imaginary portions of the complex permittivity are depicted with the initially selected regions for the multiresonant sensor operation. These regions are selected based on the dispersion of $\varepsilon'$ and $\varepsilon''$ to capture spectral trends upon oil aging. FIGS. 74A and 74B depict the real and the imaginary portions of the complex permittivity of the employed model automotive oil 10 W-30 with three levels of aging such as 0, 50, and 100% and illustrates trends of $\varepsilon'$ and $\varepsilon''$ upon oil aging, which is attractive for the selection of operating frequencies of the multiresonant sensor system. Arrows and dotted lines indicate initially selected regions for the multiresonant sensor operation.

In another experimental example, water leaks into oil were studied during the operation of a helicopter engine. The helicopter engine was a turboshaft CT7 helicopter engine made by GE. Water in the form of an emulsion was added to the oil sump prior to the engine start. A homogenizer was used to emulsify water with the CT7 engine oil. First, the loss of water in the oil during the helicopter engine operation was studied with the near-infrared spectroscopy using a Cary 500i UV-vis-NIR spectrophotometer (Varian, Inc., Santa Clara, Calif.) using quartz cuvettes with a 1-cm path length. Initially, oil samples with known amounts of water were measured to establish the relationship between near-infrared absorbance and water content. Next, samples were taken between the runs of the helicopter engine and analyzed with near-infrared spectroscopy for the presence of residual water. The 500 ppm water was added to the sump of the engine, and then the engine was allowed to run for specified time periods in the ground idle mode. Oil samples were taken between the runs and analyzed with near-infrared spectroscopy for the presence of residual water. The water presence was deduced from the characteristic water absorption band at 1900 nm after the measurement setup calibration with oil-water mixtures with the known water content. The results indicated that for a given concentration of 500 ppm water, water was completely eliminated from the oil in around five minutes on the ground idle. Thus, the water signature could be detected within the first few minutes after the engine start.

Figure 75A:
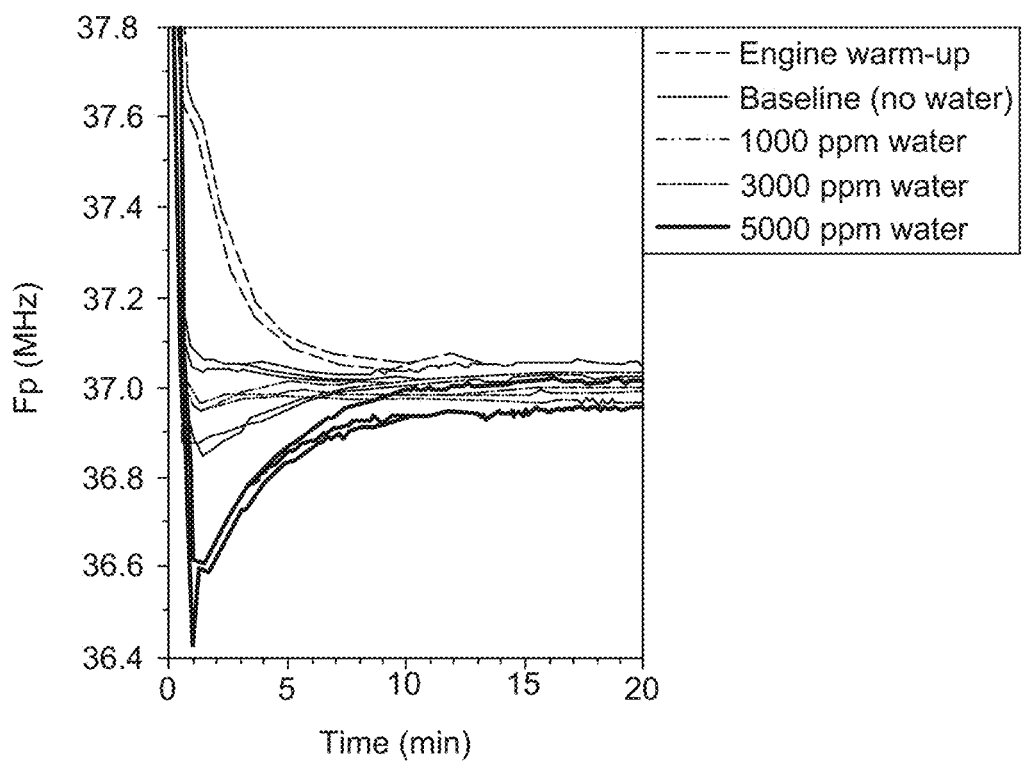
FIGS. 75A-B show the results of triplicate runs with for the engine warm-up, baseline (no added water), and water additions of 1000, 3000, and 5000 ppm, and the correlation between the sensor response and added water concentration, respectively.
Figure 75B:
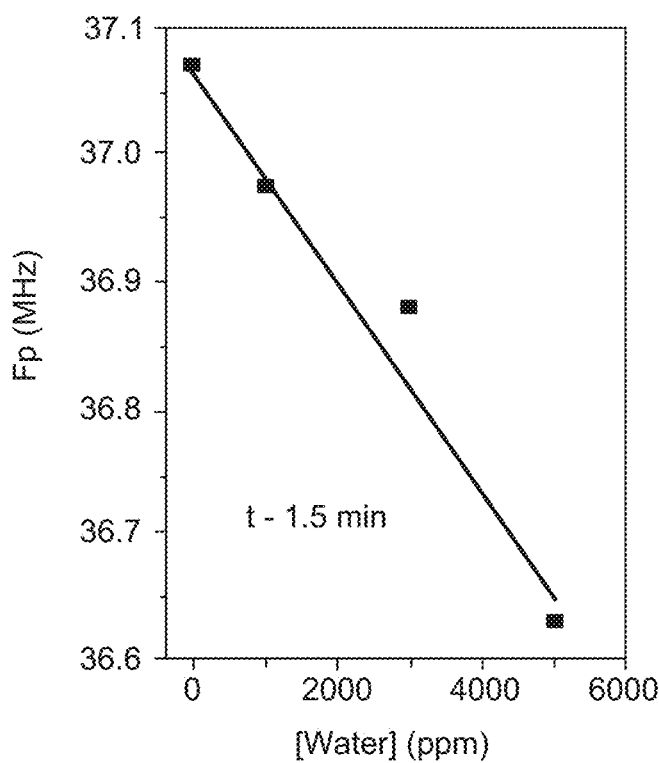

Detection of water concentrations in a turboshaft helicopter engine was further performed using the multivariable resonant sensor (e.g., such as the sensor 5802 shown in FIG. 58). The 4-cm$^2$ 100-μm-IDE-spacing sensor operating at around 38 MHz (in oil) was placed inside a 1-inch T-connector that was a part of a specially installed ⅜" OD bypass oil line connected to the engine to ensure oil flow through the sensor during the engine operation. Benchmarking of the performance of the multivariable resonant sensor was done by comparison with a conventional tuning fork sensor, installed sequentially. Measurements of water leaks were performed by adding water concentrations of 1000, 3000, and 5000 ppm and observing dynamic response patterns. Results of these experiments are summarized in FIG. 75A, which shows the results of triplicate runs with for the engine warm-up, baseline (no added water), and water additions of 1000, 3000, and 5000 ppm. The correlation between the sensor response and added water concentration was established by measuring sensor response after 1.5 min upon water addition, as shown in FIG. 75B.

Figure 76A:
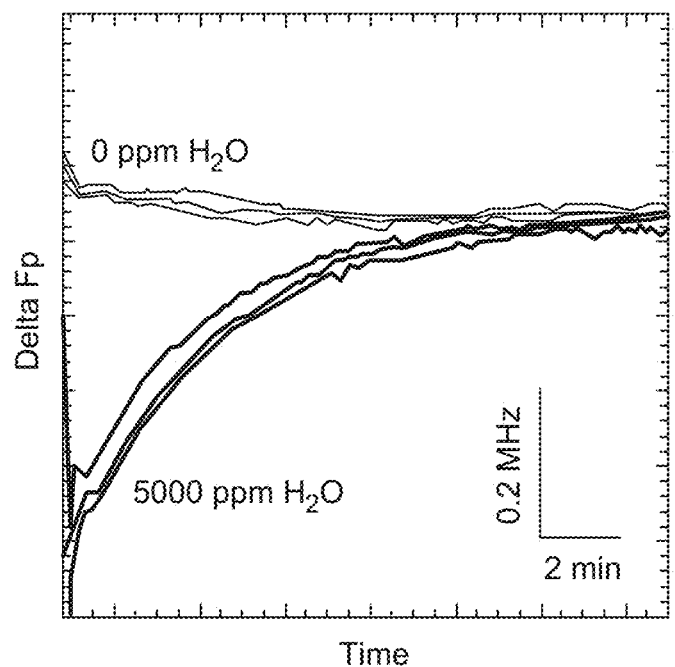
FIGS. 76A-B show responses of an installed multivariable resonant sensor and a tuning fork sensor, respectively, upon testing of engine oil of the turboshaft helicopter with an added 5000 ppm of water and observing dynamic response patterns.
Figure 76B:
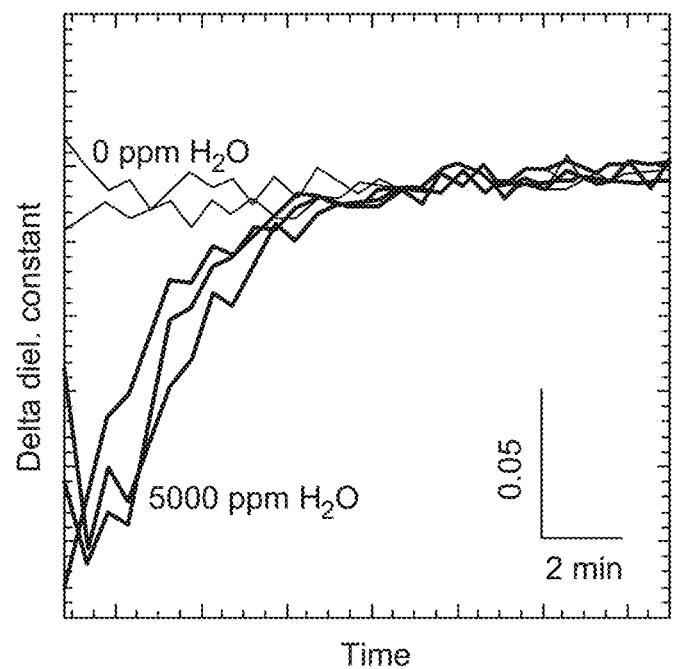

FIGS. 76A and 76B show responses of the installed multivariable resonant sensor and the tuning fork sensor, respectively, upon testing of engine oil of the turboshaft helicopter with an added 5000 ppm of water and observing dynamic response patterns. The tuning fork sensor response shown in FIG. 76B was corrected for the temperature fluctuation during the measurement. The estimated the signal-to-noise ratio of both sensors was taken at their maxima, and the noise levels were taken upon water evaporation at stable response regions during individual runs. As shown in FIG. 76A, the signal-to-noise ratio of the multivariable resonant sensor was in the range of generally 230-525. As shown in FIG. 76B, the signal-to-noise ratio of the tuning fork sensor was in the range of generally 25-60. In FIG. 76B, the dielectric constant increases with the addition of water.

Figure 77:
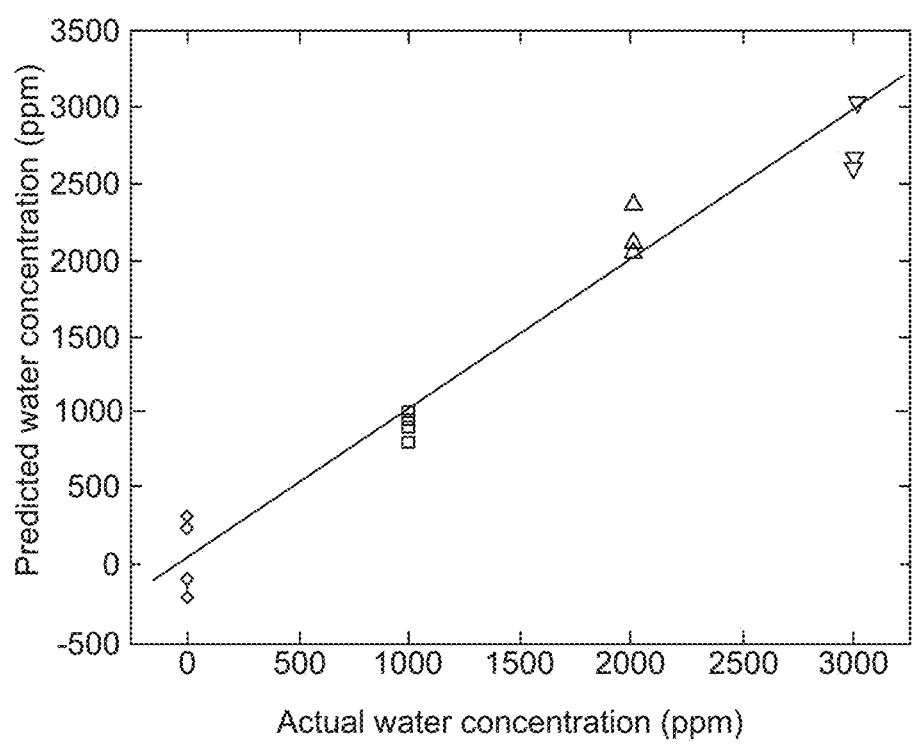
FIG. 77 illustrates results of predicted water concentrations versus actual water concentrations in different types of oils using a single transfer function.

Using an approach of selecting the appropriate frequency ranges as depicted in FIGS. 73A and 73B and FIGS. 74A and 74B, four types of automotive oil were measured with different levels of added water at concentrations of 0 ppm, 1000 ppm, 2000 ppm, and 3000 ppm. The different types of automotive oil were 0 W-20, 10 W-30, 15 W-40, and SAE30. FIG. 77 illustrates results of predicted water concentrations versus actual water concentrations in different types of oils using a single transfer function. The data in FIG. 77 illustrates the ability of the developed sensing methodology to detect and quantify an external contaminant such as water into diverse types of oil without effects of the type of oil.

A sensor of the disclosure may analyze an industrial fluid such as gas dissolved in oil or ambient air at an industrial site. Detection of methane and other gases may be performed using metal oxide sensors. A metal oxide sensor changes its resistance signal in relation to gas concentration. Unfortunately, it is well accepted that at relatively high concentrations of gases, the resistance signal of the metal oxide sensor saturates or even changes its direction of the response. Thus, over relatively large concentrations of gases, the resistance signal of the metal oxide sensors may be non-linear and even non-monotonic. When such a metal oxide sensor was connected to an LCR resonator to operate in a resonant mode as depicted in FIG. 22, measurements of resonant properties (such as the parameters shown in FIG. 23) of the sensor were determined. The metal oxide sensor was exposed to three sets of methane gas concentrations. Each set of methane gas concentrations was presented twice to the sensor thus providing two replicate measurements per each set of methane gas concentrations. Methane concentrations were as follows:

Set #1: 0, 102, 306, 510, 714, 918, 1122, 1327, 1531, and 1735 ppm.
Set #2: 0, 172, 517, 862, 1207, 1552, 1897, 2241, 2586, and 2931 ppm.
Set #3: 0, 263, 789, 1316, 1842, 2368, 2895, 3421, 3947, and 4474 ppm.

These gas concentrations were produced by diluting methane concentration of 10000 ppm available from a gas tank with air at different ratios of methane-to-air. These different ratios were provided by variable total flow of gas delivered to the sensor. To generate the Set #1 of methane concentrations, the total gas flow was relatively large as compared to the total gas flow needed to generate the Set #2 and Set #3 of methane concentrations. In this experiment, exposures of the sensor to different methane concentrations were performed for about 2 minutes and were alternated with exposures to blank clean carrier gas without methane for about 2 minutes. The time between replicates from the same set was about 14 minutes. The time between different sets was about 22 minutes.

Figure 78:
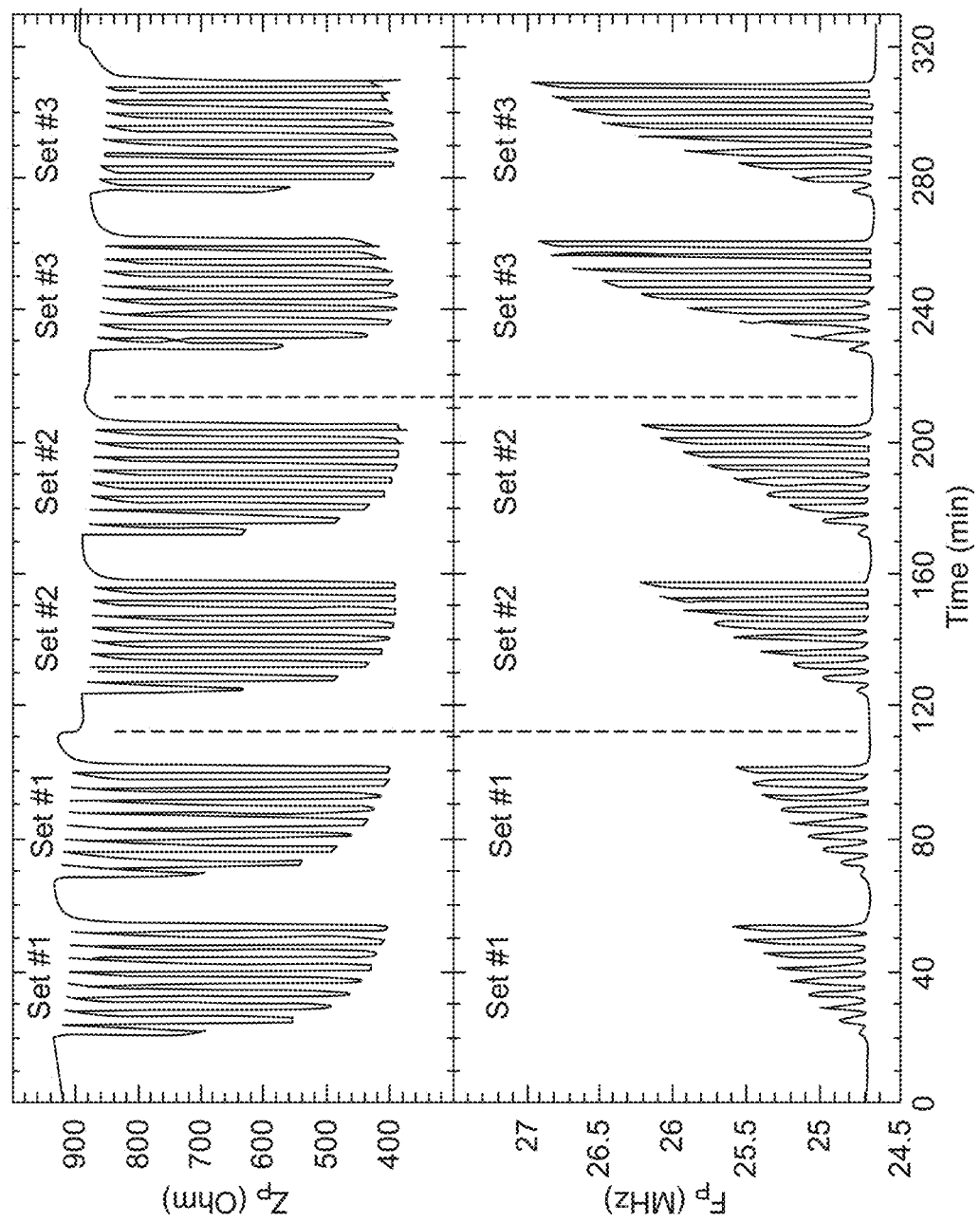
FIG. 78 depicts the Zp and Fp responses of a resonant metal oxide sensor, where Zp is resistance change of the sensor and Fp is frequency peak position of the sensor.

FIG. 78 depicts the Zp and Fp responses of the resonant metal oxide sensor, where Zp is resistance change of the sensor and Fp is frequency peak position of the sensor. The responses Zp and Fp of the sensor were completely reversible upon periodic exposures of the sensor to methane followed by the exposures to blank clean carrier gas without methane. For example, as shown in FIG. 78 over the time from 0 to 20 min, Zp response to blank clean carrier gas is about 900 Ohm, and Fp response to blank clean carrier gas is about 24.68 MHz. The first exposure of the sensor to methane concentration of 102 ppm at about 20 min for 2 minutes (Set #1, replicate 1) produced Zp signal change from about 900 Ohm to about 700 Ohm and Fp signal change from about 24.68 MHz about 24.75 MHz. Overall, Zp and Fp responses of sensor produced nine well-resolved steps upon exposure to methane per every replicate of sets 1-3. Linearity of Zp and Fp responses as a function of methane concentration is observable by comparing the magnitudes of Zp and Fp responses at different methane concentrations. At the methane gas concentrations of Set #1 above, the resistance signal response Zp of the resonant metal oxide becomes nonlinear at the high methane concentrations. At the methane gas concentrations of Set #2, the resistance signal response Zp of the resonant metal oxide becomes saturated at the high methane concentrations. At the methane gas concentrations of Set #3, the resistance signal response of the resonant metal oxide changes its direction at the high methane concentrations. Thus, the resistance signal responses Zp in all three sets are generally non-linear with respect to methane concentration. Further, there are steps in the baseline response of the sensor upon changes of the flow conditions from Set #1 to Set #2 and to Set #3.

As shown in FIG. 78, the frequency peak position response Fp of the resonant metal oxide sensor has a significant linearity with respect to methane concentration. For example, the frequency peak position Fp (represented as the peaks of the plot line) signal response of the resonant metal oxide sensor increases generally linearly as the concentration of methane increases in each set. At the methane gas concentrations of Set #1 and Set #2, Fp signal response of the resonant metal oxide is linear at all such concentrations, but the Fp signal response at the concentrations of Set #3 is slightly nonlinear at the high methane concentrations. Further, there are no noticeable steps in the baseline response of the sensor upon changes of the flow conditions from Set #1 to Set #2 and to Set #3. Thus, the application of a metal oxide sensor in a resonant mode as a part of the LCR circuit provides the advantages of having a linear frequency peak position Fp response of the sensor to gas concentrations and having a stable baseline. The Fp response of the sensor is directly related to the change in the capacitance of the sensor. Change in capacitance of described methane sensor may be measured using a resonant or non-resonant readout. As shown in FIG. 78, a linear progression of Fp response as a function of methane concentration was observed. A nonlinear progression of Zp response as a function of methane concentration was observed.

Figure 79:
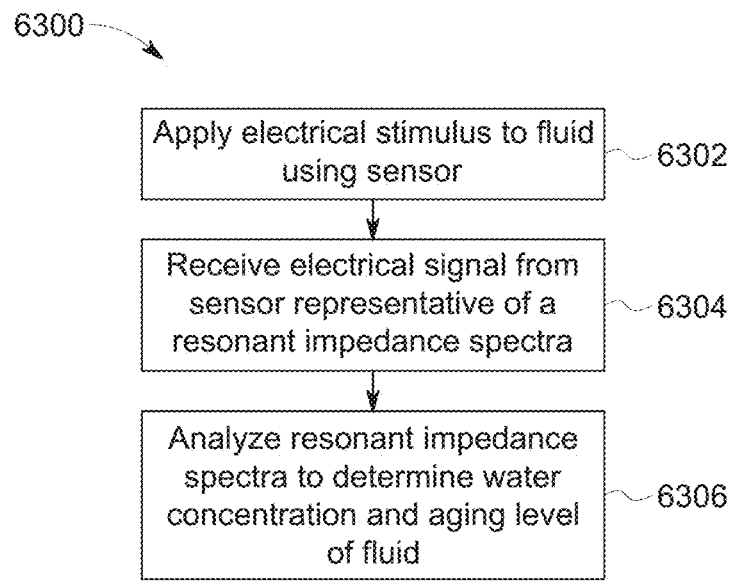
FIG. 79 is a flow chart representative of a method for determining multiple properties of an industrial fluid.

FIG. 79 is a flow chart representative of a method 6300 for determining multiple properties of an industrial fluid. At 6302, an electrical or electromagnetic stimulus is applied to an industrial fluid using a sensor. The "electrical stimulus" may additionally or alternatively be an electromagnetic stimulus. The sensor includes at least one resonant inductor-capacitor-resistor (LCR) circuit configured to generate the electrical stimulus. The electrical or electromagnetic stimulus is applied to the industrial fluid via multiple electrodes at a sensing region of the sensor in operational contact with the industrial fluid. Optionally, the sensor may include multiple LCR circuits that have different resonant frequencies. Applying the electrical or electromagnetic stimulus to the industrial fluid may include generating the electrical or electromagnetic stimulus to incorporate the resonant frequencies of the resonant LCR circuits such that the resonant impedance spectral response is measured over the resonant frequencies of the resonant LCR circuits. The method 6300 may also include tuning the electrical or electromagnetic stimulus generated by the at least one LCR circuit using one or more tuning elements. The tuning elements may include one or more inductors, capacitors, resistors, resonators, or impedance transformers.

At 6304, an electrical or electromagnetic signal is received from the sensor. The electrical or electromagnetic signal is representative of a resonant impedance spectral response of the sensing region in operational contact with the industrial fluid in response to the electrical or electromagnetic stimulus being applied to the industrial fluid. At 6306, the resonant impedance spectral response is analyzed to determine both a water concentration in the industrial fluid and an aging level of the industrial fluid based on the analyzed resonant impedance spectra. Although "water concentration" is mentioned, in other embodiments the concentration may be of another external contaminant other than water. The water or other external contaminant concentration in the industrial fluid and the aging level of the industrial fluid may be determined by comparing the extracted complex resonance parameters to known resonance parameters associated with various water or other external contaminant concentrations in the industrial fluid and various aging levels of the industrial fluid. The aging level of the fluid is determined by categorizing the fluid as three levels as one of fresh, old, or intermediate. The aging level of the fluid may be also determined by categorizing the fluid with more levels of aging where the number of levels of aging may be 8, 64, 128, 256, 512, 1024, 2048, 4096, 65536 or more. The number of aging levels determined by the sensor may depend on the developed transfer function between fluid aging and multivariable sensor response.

The determination of oil aging by levels is important for different applications. For example a two-level aging of oil means that level 1 is a fresh oil and level 2 is aged oil that requires oil replacement or some other action. The higher number of resolution levels of oil aging, the more accurate performed actions can be, including prognostic algorithms to predict the remaining life of oil and/or the machine or an industrial system or site.

Analyzing the resonant impedance spectra may include extracting complex resonance parameters of the resonant impedance spectra. The complex resonance parameters are at least some of a frequency position (Fp) and magnitude (Zp) of a real part of the resonant impedance spectra, a resonant frequency (F1) and antiresonant frequency (F2) of an imaginary part of the resonant impedance spectra, an impedance magnitude (Z1) at the resonant frequency (F1) and an impedance magnitude (Z2) at the antiresonant frequency (F2), and a zero-reactance frequency (Fz) at the imaginary part of the resonant impedance spectra.

In an embodiment, a system includes a sensor and a device body. The sensor includes a sensing region and at least one resonant inductor-capacitor-resistor (LCR) circuit. The sensing region includes at least two electrode structures. The sensing region of the sensor is configured to be placed in operational contact with an industrial fluid of interest. The at least one resonant LCR circuit is electrically connected to the electrode structures and configured to generate an electrical stimulus having a spectral frequency range. The electrical stimulus is applied to the industrial fluid via the electrode structures. The device body is operably coupled to the sensor. The device body includes one or more processors configured to receive an electrical signal from the sensor. The electrical signal is representative of a resonant impedance spectral response of the sensing region in operational contact with the industrial fluid in response to the electrical stimulus being applied to the industrial fluid. The one or more processors are further configured to analyze the resonant impedance spectral response and determine both a water concentration in the industrial fluid and an aging level of the industrial fluid based on the resonant impedance spectral response that is analyzed.

In one example, industrial fluid is lubricant, fuel, hydraulic media, drive fluid, power steering fluid, solvent, power brake fluid, drilling fluid, oil, crude oil, heat transfer fluid, insulating fluid, compressed air, ambient air on an industrial site or structure, water, naturally occurring fluid, synthetic fluid.

In one example, industrial fluid is lubricating oil with known type and level of additives designed for their applications under different environmental conditions and with different wear protection, and different particles-deposit control.

In one example, the sensing region of the sensor is configured to be disposed within a reservoir of a machine having moving parts that are lubricated by the industrial fluid in the reservoir.

In one example, each resonant LCR circuit includes one or more tuning elements. The one or more tuning elements comprise one or more inductors, capacitors, resistors, resonators, or impedance transformers.

In one example, the sensor includes multiple resonant LCR circuits that have different resonant frequencies. The spectral frequency range of the electrical stimulus is applied to the industrial fluid incorporating the resonant frequencies of the resonant LCR circuits such that the resonant impedance spectral response is measured over the resonant frequencies of the resonant LCR circuits. Optionally, the sensor includes a multiplexer that is configured to individually control the resonant LCR circuits to tune the electrical stimulus that is applied to the industrial fluid.

In one example, the industrial fluid of interest is at least one of an oil, a fuel, a solvent, solid, or ambient air at an industrial site. Non-limiting examples of an industrial site include manufacturing facility, processing facility, disposal facility, industrial research facility, gas producing facility, oil producing facility, and others.

In one example, the one or more processors are configured to analyze the resonant impedance spectral response by extracting complex resonance parameters of the resonant impedance spectral response. The one or more processors are configured to determine the concentration of water or other external contaminant in the industrial fluid and the aging level of the industrial fluid by comparing the extracted complex resonance parameters to known resonance parameters associated with various water concentrations and aging levels. Optionally, the complex resonance parameters include one or more of a frequency position (Fp) and magnitude (Zp) of a real part of the resonant impedance spectra, a resonant frequency (F1) and antiresonant frequency (F2) of an imaginary part of the resonant impedance spectra, an impedance magnitude (Z1) at the resonant frequency (F1) and an impedance magnitude (Z2) at the antiresonant frequency (F2), or a zero-reactance frequency (Fz) at the imaginary part of the resonant impedance spectra.

In one example, the one or more processors are configured to determine the aging level of the industrial fluid as being at or proximate to a beginning of a recommended fluid life, at or proximate to a middle of the recommended fluid life, or at or proximate to an end of the recommended fluid life.

In one example, the sensor has a probe body that extends between a distal end and a proximal end. The probe body includes a shoulder disposed between the distal end and the proximal end. The sensing region of the sensor extends from the shoulder to the distal end of the probe body. The electrode structures of the sensing region are disposed at different distances relative to the shoulder such that the electrode structures extend different depths into the industrial fluid.

In one example, at least one of the electrode structures of the sensing region operates at higher frequencies than at least one other electrode structure of the electrode structures.

In one example, at least one of the electrode structures of the sensing region includes electrodes coated with at least one of a protective layer or a sensing layer and at least another of the electrode structures includes bare electrodes.

In one example, the multivariable sensor has electrodes of the sensing region that are coated with a sensing layer where the electrodes and the sensing layer operate at an elevated temperature ranging from about 100 degrees Celsius to about 1600 degrees Celsius.

In an embodiment, a method includes applying an electrical stimulus to an industrial fluid using a sensor. The sensor includes at least one resonant inductor-capacitor-resistor (LCR) circuit configured to generate the electrical stimulus. The electrical stimulus is applied to the industrial fluid via at least two electrode structures at a sensing region of the sensor in operational contact with the industrial fluid. The method also includes receiving an electrical signal from the sensor representative of a resonant impedance spectral response of the sensing region in operational contact with the industrial fluid in response to the electrical stimulus being applied to the industrial fluid. The method further includes analyzing the resonant impedance spectral response to determine both a water concentration in the industrial fluid and an aging level of the industrial fluid based on the resonant impedance spectra that is analyzed. The stimulus may be electrical or electromagnetic stimulus.

In one example, analyzing the resonant impedance spectral response includes extracting complex resonance parameters of the resonant impedance spectral response. The complex resonance parameters are one or more of a frequency position (Fp) and magnitude (Zp) of a real part of the resonant impedance spectra, a resonant frequency (F1) and antiresonant frequency (F2) of an imaginary part of the resonant impedance spectra, an impedance magnitude (Z1) at the resonant frequency (F1) and an impedance magnitude (Z2) at the antiresonant frequency (F2), or a zero-reactance frequency (Fz) at the imaginary part of the resonant impedance spectral response. Optionally, the water concentration in the industrial fluid and the aging level of the industrial fluid are determined by comparing the extracted complex resonance parameters to known resonance parameters associated with various water concentrations in the industrial fluid and various aging levels of the industrial fluid. Water is one of exemplary external contaminants. Additional non-limiting examples of external contaminants fuel, dust, metal wear particles, coolant, debris, and others.

In one example, the sensor that applies the electrical stimulus to the industrial fluid is a metal oxide sensor.

In one example, the method further includes tuning the electrical stimulus generated by the at least one resonant LCR circuit using one or more tuning elements. The one or more tuning elements include one or more inductors, capacitors, resistors, resonators, or impedance transformers.

In one example, analyzing the resonant impedance spectral response to determine the aging level of the industrial fluid includes categorizing the industrial fluid as being at or proximate to a beginning of a recommended fluid life, at or proximate to a middle of the recommended fluid life, or at or proximate to an end of the recommended fluid life.

In one example, the sensor includes multiple resonant LCR circuits that have different resonant frequencies. Applying the electrical stimulus to the industrial fluid includes generating the electrical stimulus to incorporate the resonant frequencies of the resonant LCR circuits such that the resonant impedance spectral response is measured over the resonant frequencies of the resonant LCR circuits.

In an embodiment, a system for monitoring a condition of an industrial site includes a sensor and a device body operably coupled to the sensor. The sensor has at least two sufficiently non-correlated output signals representative of a response of the sensor to an industrial fluid at the industrial site. The device body includes one or more processors configured to receive the output signals from the sensor and analyze the output signals to determine both a concentration of an external contaminant in the industrial fluid and an aging level of the industrial fluid based on the output signals.

In one example, the condition of the industrial site is based on the concentration of the external contaminant in the industrial fluid and the aging level of the industrial fluid.

In one example, the industrial site is at least one of a first machine that has moving parts, a second machine that does not have movable parts, a manufacturing facility, a processing facility, a disposal facility, an industrial research facility, a gas producing facility, or an oil producing facility.

In one example, the industrial fluid is at least one of a lubricant, a fuel, a hydraulic media, a drive fluid, a power steering fluid, a solvent, a power brake fluid, a drilling fluid, an oil, an insulating fluid, a heat transfer fluid, compressed air, ambient air, water, a naturally occurring fluid, or a synthetic fluid.

In one example, the industrial fluid is a lubricating oil with known type and level of additives designed for exposure to multiple environmental conditions and with different wear protection and different particles-deposit control.

In one example, the sensor is a metal oxide sensor.

In one example, the output signals of the sensor represent a resonant impedance spectral response of the sensor in operational contact with the industrial fluid responsive to an electrical stimulus being applied to the industrial fluid. The one or more processors of the device body are configured to analyze the output signals by extracting complex resonance parameters of the resonant impedance spectral response. The complex resonance parameters include a frequency position of a real part of the resonant impedance spectral response. The frequency position increases linearly with increasing concentration of the external contaminant.

In one example, one of the two sufficiently non-correlated output signals represents an impedance response of the sensor to the industrial fluid. The other of the two sufficiently non-correlated output signals represents a capacitance response of the sensor to the industrial fluid.

Figure 80:
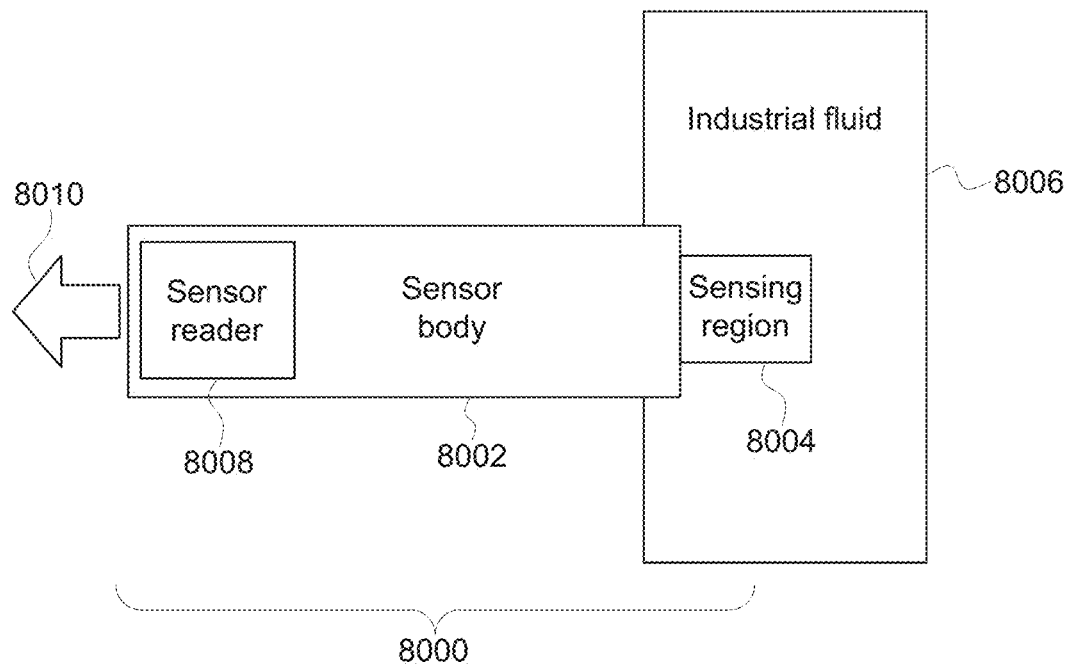
FIG. 80 illustrates another embodiment of a sensor assembly.

FIG. 80 illustrates another embodiment of a sensor assembly 8000. The sensor assembly 8000 may represent one or more embodiments of the sensor or sensor assemblies 1714, 1940, 5802 described herein, and may be included in one or more of the sensor systems described herein. The sensor assembly 8000 is placed into contact with an industrial fluid of interest, such as oil, fuel, solvent, etc.

The sensing region 8004 may include electrodes, as described above. The sensing region 8004 of the sensor assembly 8000 is placed into contact with an industrial fluid 8006. The electrodes can generate an electric field of one or more frequencies to excite the fluid 8006 and/or sensing region 8004. The sensing region 8004 includes an electrical, non-resonant and/or resonant circuit that can operate at one or more non-harmonic and non-resonant or resonant frequencies. A sensor reader 8008 is located inside the sensor body 8002, and may include one or more processors (e.g., application specific integrated circuits, field programmable gate arrays, microprocessors, etc.). The sensor reader 8008 can represent the sensor reader 106. In one embodiment, the sensor reader 8008 can include an application specific integrated circuit available from Analog Devices (Model AD5933).

The sensor reader 8008 measures the response of the sensing region 8004 during excitation of the sensing region 8004 by an electric field generated in the fluid 8006, as described above. The sensor reader 8008 can sample the measurements obtained by the sensing region 8004 at one or more different resolutions. In one embodiment, the sensor reader 8008 can read the measurements of the sensing region 8004 at a resolution of 8 bit. Alternatively, the resolution may be 12 bit, 16 bit, or another larger resolution. The larger resolutions may be obtained by filtering noise from the sampled measurements and/or by averaging multiple measurements.

The sensing region 8004 can operate as one or more LCR circuits that, in response to being excited by current provided to the LCR circuit, generate an electrical signal that represents impedance spectra of the sensing region 8004 during operational contact with the fluid 8006 over a measured spectral frequency range. The signal may be used to analyze the impedance spectra and to determine one or more properties of the fluid as described herein.

The sensing region 8004 is directly connected with the sensor reader 8008 in one embodiment. For example, the sensing region 8004 may be coupled with the sensor reader 8008 by one or more wireless connections or links. The signal that is output by the sensing region 8004 may be communicated directly to the sensor reader 8008 without the signal being conducted or otherwise communicated to another component and without the signal being altered (e.g., filtered, amplified, digitized, conditioned, converted, or otherwise processed) by another component. Alternatively, the signal may be communicated from the sensing region 8004 to another component and modified or altered by the other component before being conveyed to the sensor reader 8008.

The sensor reader 8008 may generate an output signal 8010 that represents one or more characteristics of the industrial fluid 8006, such as an impedance spectrum, impedance spectra, an age of the fluid 8006, a level or amount of contaminants in the fluid 8006, or the like. The output signal 8010 may be a digital signal. This output signal 8010 may be communicated via one or more wired and/or wireless connections to the controller described above, or to another location. In one embodiment, the sensor assembly 8000 may have a digital address to allow communication between the sensor assembly 8000 and one or more other devices, such as the controller described above. The sensor reader 8008 may provide digital data security to prevent one or more other devices other than the controller or another reader from communicating with or corrupting the data that is output by the sensor assembly 8000.

The sensor assembly 8000 includes an outer housing, or body, 8002. The circuitry of the sensor assembly 8000, including the sensor reader 8008 and the sensing region 8008, may be within and/or attached directly to the body 8002 such that the sensor reader 8008 and the sensing region 8008 are proximate to each other and form a single device. In one embodiment, these components are inside a single continuous or contiguous body 8002, such as a single external housing. The body 8002 may provide radio frequency (RF) shielding to the circuitry of the sensor assembly 8000 and may be able to provide dimensional and thermal stability, such as by protecting components within the body 8002 at elevated temperatures (e.g., temperatures up to 250 degrees Celsius). The body 8002 can provide environmental sealing of the components of the sensor assembly 8000. In one embodiment, the body 8002 is hermetically sealed. Nonlimiting examples of materials that may be used to form the body 8002 include stainless steel, aluminum, metal alloys, metal-ceramic composites, or metal dielectric composites.

The sensor assembly 8000 may be powered from a variety of sources. As one example, the sensor assembly 8000 may include an internal battery as a power source. Alternatively, the sensor assembly 8000 can use ambient energy harvesting to obtain electric power. In another example, the sensor assembly 8000 can operate with wirelessly supplied power, such as may be provided through an inductive connection with a power source.

Figure 81:
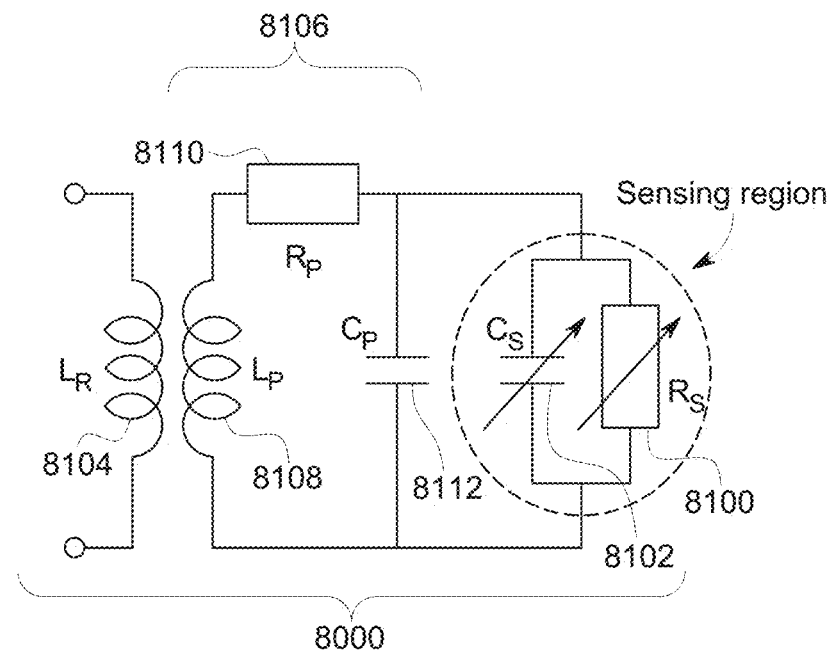
FIG. 81 illustrates a circuit diagram of one embodiment of the sensor assembly shown in FIG. 80.

FIG. 81 illustrates a circuit diagram of one embodiment of the sensor assembly 8000 shown in FIG. 80. The sensor assembly 8000 can include a variable resistor $R_s$ (or 8100) and a variable capacitor $C_s$ (or 8102), which can represent the sensing region 8004 (or the sensing region 1938 shown in FIG. 20). An inductor $L_r$ (or 8104) represents the inductance of the wireless connection between the sensor reader 8010 and the sensing region 8004. The inductor 8104 can be inductively coupled with an LCR circuit 8106 that represents the components that provide the resonant response of the sensor assembly 8000 to the electric fields. The LCR circuit 8106 includes an inductor $L_p$ (or 8108), resistor $R_p$ (or 8110), and capacitor $C_p$ (or 8112) connected in series with each other in a loop.

The circuit diagram of the sensor assembly 8000 shown in FIG. 81 may not allow for the resonance of the sensing region 8004 to be controlled, or tuned. For example, the sensor assembly 8000 shown in FIG. 81 may resonate for a single frequency (dependent upon the condition of the fluid 8006, such as the age and/or level of contaminants in the fluid 8006). In accordance with one or more embodiments of the subject matter described herein, the resonance of the sensing region 8004 of the sensor assembly 8000 may be controlled (e.g., tuned) and be changed between different, predetermined frequencies. These frequencies may not be dictated by the fluid under examination, but may be selected by an operator of the sensor assembly 8000.

The sensor reader 8008 may excite the sensing region 8004 through multiple different frequencies using active resonators in the circuitry of the sensor assembly 8000. Active resonators may include components that are powered by a power source, such as a battery, energy harvesting, wireless power, or the like. Alternatively, the sensing region 8004 may be excited using passive resonators in the circuitry of the sensor assembly 8000. Passive resonators may not be powered by a power source, but may be powered by inductive coupling or backscatter coupling with the sensor reader 8008. The excitation of the sensing assembly 8004 may be controlled by the sensor reader 8008 using multi-carrier wideband excitation.

Figure 82:
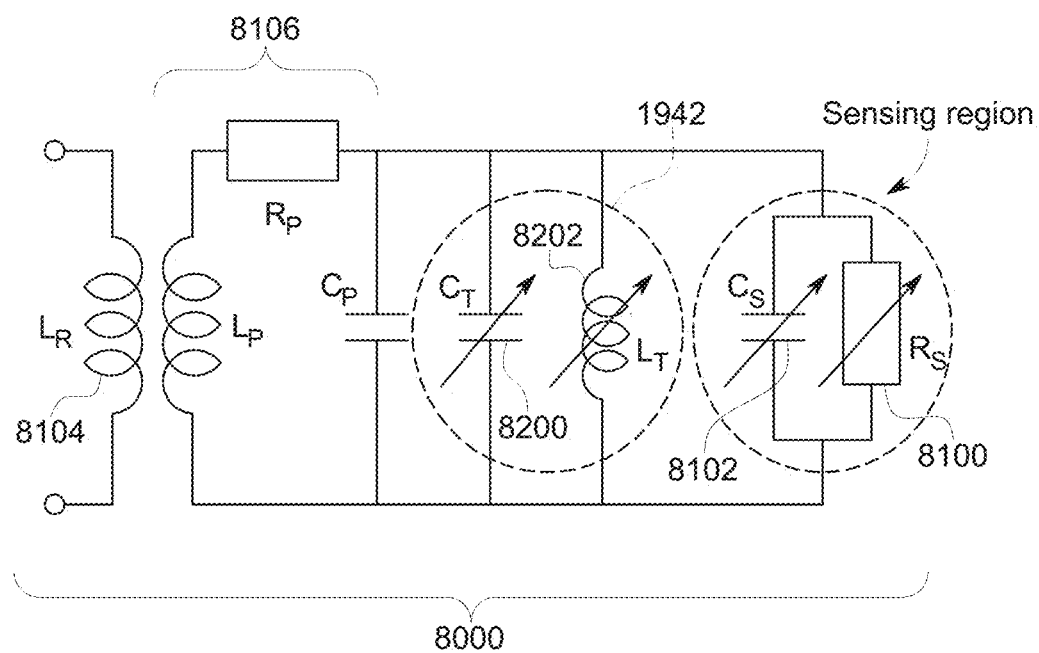
FIG. 82 illustrates a circuit diagram of the sensor assembly shown in FIG. 80 in an embodiment where the resonance of the sensor assembly may be controlled.

FIG. 82 illustrates a circuit diagram of the sensor assembly 800 shown in FIG. 80 in an embodiment where the resonance of the sensor assembly 8000 may be controlled. The circuit diagram of the sensor assembly 8000 may be similar or identical to the sensor circuit 2010 shown in FIG. 20, with the details of the tuning components 1942 (FIG. 20) shown in FIG. 81. For example, the sensor assembly 8000 may include the resistor 8100, capacitor 8102, the LCR circuit 8106, and the inductor 8104, but also may include a variable capacitor $C_T$ (or 8200) and a variable inductor $L_T$ (or 8202) as the tuning components 1942 shown in FIG. 20.

While the resistance of the resistor 8100 and the capacitance of the capacitor 8102 of the sensing region 8004 may change based on the condition of the fluid 8006 (e.g., the age and/or level of contaminants in the fluid 8006), the inductance of the inductor 8202 and/or the capacitance of the capacitor 8200 may be varied (e.g., by the controller or an operator) to change the resonant frequency of the sensing region 8004. For example, the inductance and/or capacitance may be increased or decreased to change which frequencies of electric field cause the current conducted in the sensor assembly 8000 to resonate.

The tunable resonance of the sensor assembly 8000 allows the sensor assembly 8000 to examine the fluid 8006 to determine which of several different frequencies cause the sensor assembly 8000 to resonate. In contrast to using several different sensor assemblies that each resonate at different frequencies, the sensor assembly 8000 may be a single sensor with a single sensing region 8004 that can change which frequencies cause the sensing region 8004 to resonate. The controller of the sensing system can control the frequency at which the sensing region 8004 resonates by changing the capacitance and/or the inductance of the variable capacitor 8200 and inductor 8202.

The sensor assembly 8000 can operate as a multi-frequency, non-resonant sensor capable of operating at several different frequencies across dispersion profiles of different external contaminants and aging products (e.g., in the fluid 8006). The resonance of the sensor assembly 8000 may be tuned to not resonate in response to excitation at one or more frequencies. The electric fields with the resonant frequencies may be harmonic resonant frequencies. Alternatively, the electric fields with the resonant frequencies may be non-harmonic resonant frequencies. The impedance of the fluid 8006 may change with increasing age, levels of contaminants, and/or the presence of different contaminants in the fluid 8006. For example, in a first state (e.g., with the first state representing a first capacitance of the variable capacitor 8200 and a first inductance of the variable inductor 8202), the circuit of the sensor assembly 8000 may resonate at a first frequency while the sensing region 8004 is at least partially submerged in the fluid under examination. But, in a different, second state (e.g., with second state representing a different, second capacitance of the variable capacitor 8200 and/or a different, second inductance of the variable inductor 8202), the circuit of the sensor assembly 8000 may not resonate at the same first frequency while the sensing region 8004 is at least partially submerged in the fluid under examination.

The sensor reader 8008 may control the frequencies at which the sensor assembly 8000 generates an electric field in the fluid under examination. For example, the sensor reader 8008 may include an integrated circuit that causes the sensor assembly 8000 to sweep through several different frequencies of electric fields. The sensor reader 8008 may sweep through the frequencies by changing the frequency of the electric field in a continuous manner such that, during a frequency sweep, the frequency continually changes. The frequency can continually change by not being the same frequency at any two points in time and varying between many different frequencies (e.g., more than two frequencies) during the frequency sweep from a first frequency to a different, second frequency. Such a sensor reader 8008 can be referred to as a frequency-sweeping sensor reader 8008 or a frequency-sweeping integrated circuit.

Optionally, the sensor reader 8008 may include an integrated circuit that causes the sensor assembly 8000 to step through several different frequencies of electric fields. The sensor reader 8008 may step through the frequencies by changing the frequency of the electric field in a non-continuous manner. For example, the sensor reader 8008 can cause the sensing assembly 8000 to generate an electric field at a first frequency for a first period of time, then change to generating the electric field at a different, second frequency for a second period of time, and so on. The frequency can change in a step-wise manner by remaining at the same frequency for each of the periods of time. These periods of time may be same or may be different. Such a sensor reader 8008 can be referred to as a frequency-stepping sensor reader 8008 or a frequency-stepping integrated circuit. The sensor reader 8008 can excite the sensing region 8004 through several frequencies using sliding window correlation for wide band measurements. The sliding window correlation is a technique for measurements of the frequency and phase characteristics of a range of signals that are related to a sensor device. This technique is used to perform such measurements over a broad band of frequencies. The correlation can be applied in order to measure response of the sensor assembly 8000 over a spectral range from 10 Hz to 10 GHz (or another frequency range).

As described above, the spectral response of the sensing region 8004 in the fluid of interest can represent characteristics of the fluid, such as a level of degradation or age of the fluid and/or levels or amounts of external contaminants in the fluid. The sensor assembly 8000 can operate in a multivariable mode by changing whether the sensing region 8004 resonates or does not resonate at various frequencies in order to provide measurements of multiple outputs from the sensing region 8004. Some outputs can represent the response of the sensing region 8004 during time periods that the sensing region 8004 does not resonate in the electric field generated in the fluid, while other outputs can represent the response of the sensing region 8004 during other time periods that the sensing region 8004 resonates in the electric field generated in the fluid. These outputs represent independent measurements of changes in the fluid, and can be used to more accurately characterize the state of the fluid. For example, the resonant and non-resonant responses of the sensing assembly 8000 in different electric fields can be measured in different fluids having different known ages and different known levels of contaminants. These responses can be compared to resonant and/or non-resonant responses of the sensing assembly 8000 measured in a fluid under examination with an unknown age and/or level of contaminants. This comparison can be used to determine or estimate the age and/or level of contaminants in the fluid under examination, such as by determining which of the known responses more closely match the responses of the sensing assembly 8000 in the fluid under examination than other known responses.

In one embodiment, the sensor assembly 8000 may be calibrated prior and/or during measurements of the fluid 8006. The controller (described above) may calibrate the sensor reader 8008 and/or the sensing region 8004 based on ambient or external conditions to which the sensor assembly 8000 is exposed.

Figure 83:
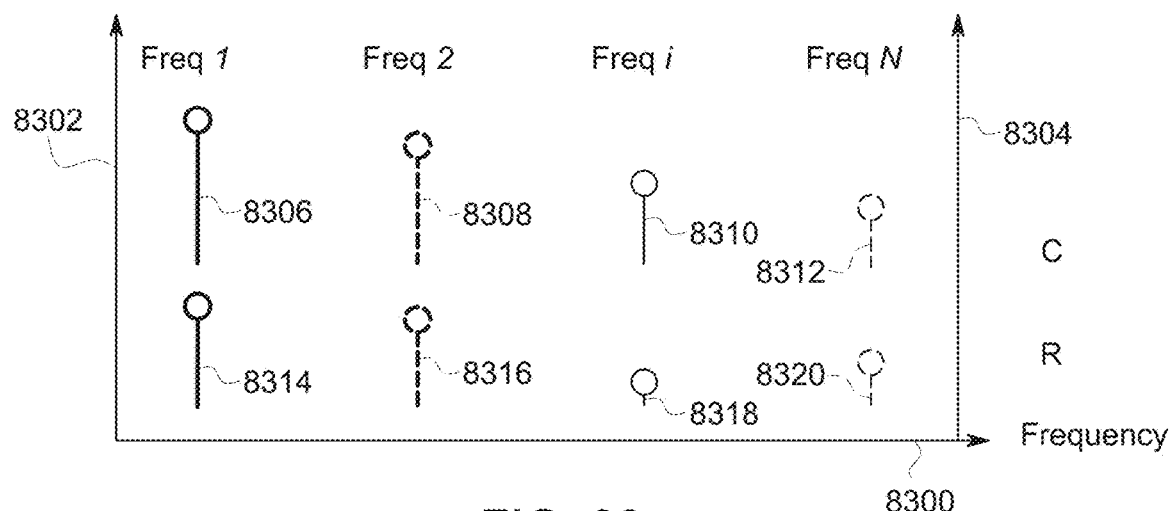
FIG. 83 illustrates operation of the sensor assembly at several different non-resonant frequencies according to one example.

FIG. 83 illustrates operation of the sensor assembly 8000 at several different non-resonant frequencies according to one example. A horizontal axis 8300 represents different frequencies of the electric field generated in the fluid by the sensor assembly 8000, a first vertical axis 8302 represents different capacitances of the fluid 8006 as measured by the sensor assembly 8000, and a second vertical axis 8304 represents different resistances of the fluid 8006 as measured by the sensor assembly 8000.

The sensor assembly 8000 is tuned to not resonate in the electric fields of the different frequencies "Freq 1," "Freq 2," "Freq i," and "Freq N". The capacitances C (e.g., capacitances 8306, 8308, 8310, 8312) and resistances R (e.g., resistances 8314, 8316, 8318, 8320) of the fluid 8006 were measured by the sensor assembly 8000 during exposure of the assembly 800 to the different non-resonant frequencies. As shown in FIG. 83, the sensing region 8004 of the sensor assembly 8000 may measure a range of capacitances C and resistances R of the sensor that in in contact with fluid 8006 at several non-resonant frequencies of the sensor assembly 8000. The set or group of capacitances C and resistances R at one or more of the non-resonant frequencies may vary over a range of values, as shown in FIG. 83. For example, the capacitances 8306 and resistances 8314 for the frequency Freq 1 vary over a larger range than the capacitances 8310, 8312 and resistances 8318, 8320 for the frequencies Freq i and Freq N.

Figure 84:
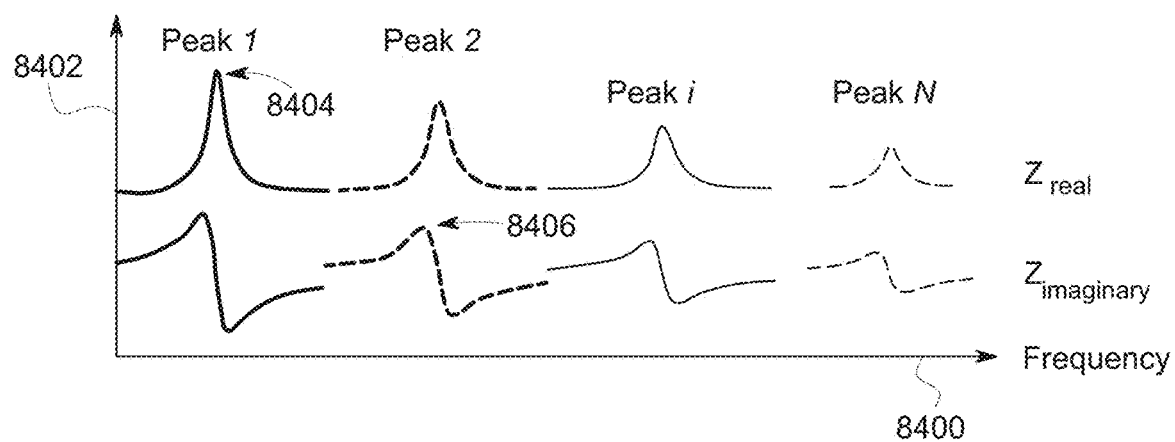
FIG. 84 illustrates operation of the sensor assembly at several different resonant frequencies according to one example.

FIG. 84 illustrates operation of the sensor assembly 8000 at several different resonant frequencies according to one example. A horizontal axis 8400 represents frequencies of electric fields generated in the fluid by the sensor assembly 8000 and a vertical axis 8402 represents impedance of the sensor as measured by the sensor assembly 8000 at the various frequencies. The sensor assembly 8000 generated electric fields of a range of frequencies by sweeping through different ranges of frequencies. For each of the range of frequencies that were swept through by the sensor assembly 8000, real and imaginary impedance peaks 8404, 8406 were measured by the sensor assembly 8000. These peaks 8404, 8406 occur at frequencies to which the sensor assembly 8000 resonates.

The capacitances, resistances, and/or impedances measured by the sensor assembly 8000 while operating in a non-resonating mode (e.g., the example of FIG. 83) and/or in a resonating mode (e.g., the example of FIG. 84) can be used to determine the age and/or level of contaminants in the fluid under examination. Different combinations of capacitances, resistances, and/or impedances for fluids having known ages and levels of contaminants may be measured by the sensor assembly 8000 while operating in the non-resonating and/or resonating modes. These capacitances, resistances, and/or impedances can then be compared to capacitances, resistances, and/or impedances measured for fluids having unknown ages and/or levels of contaminants using the sensor assembly 8000 while operating in the non-resonating and/or resonating modes. The capacitances, resistances, and/or impedances associated with the known fluids can be compared with the measured capacitances, resistances, and/or impedances of fluids under examination which have unknown ages and/or contaminants level to determine the ages and/or contaminant levels of the fluids under examination. The ages and/or contaminants levels of the fluids under examination may be measured on different time scales ranging from microseconds to days and to years.

Figure 85:
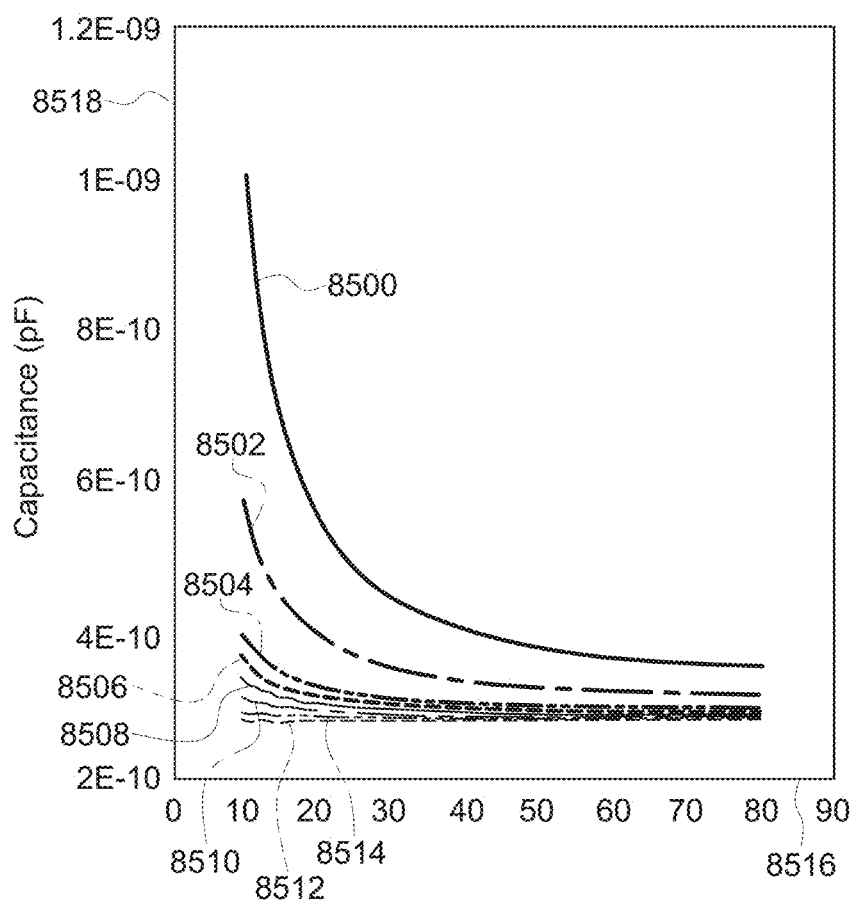
FIG. 85 illustrates measured capacitances for different levels of a contaminant in a fluid under examination according to one example.

FIG. 85 illustrates measured capacitances 8500, 8502, 8504, 8506, 8508, 8510, 8512, 8514 for different levels of a contaminant in a fluid under examination according to one example. Measurements were performed using an IDE structure connected to an application specific integrated circuit available from Analog Devices (Model AD5933) that was the sensor reader 8008. The measured capacitances 8500, 8502, 8504, 8506, 8508, 8510, 8512, 8514 are shown alongside a horizontal axis 8516 representative of frequency (e.g., in units related to hertz) and a vertical axis 8518 representative of capacitance measured by the sensor assembly 8000 (e.g., in units of picoFarads). The sensor reader 8008 used a frequency-sweeping process to examine a range of frequencies of electric fields to measure the capacitances 8500, 8502, 8504, 8506, 8508, 8510, 8512, 8514 shown in FIG. 85. The fluid under examination in FIG. 85 was ethanol and the contaminant in the ethanol was water. The capacitances 8500, 8502, 8504, 8506, 8508, 8510, 8512, 8514 were measured for different levels of water in ethanol. The table below lists the level (e.g., amount) of water for each of the capacitances the capacitances 8500, 8502, 8504, 8506, 8508, 8510, 8512, 8514 that were measured.

| Capacitances | Level of Water in Ethanol (in milliliters) |
| --- | --- |
| 8500 | 20 |
| 8502 | 10 |
| 8504 | 5 |
| 8506 | 4 |
| 8508 | 3 |
| 8510 | 2 |
| 8512 | 1 |
| 8514 | 0 |

Figure 86:
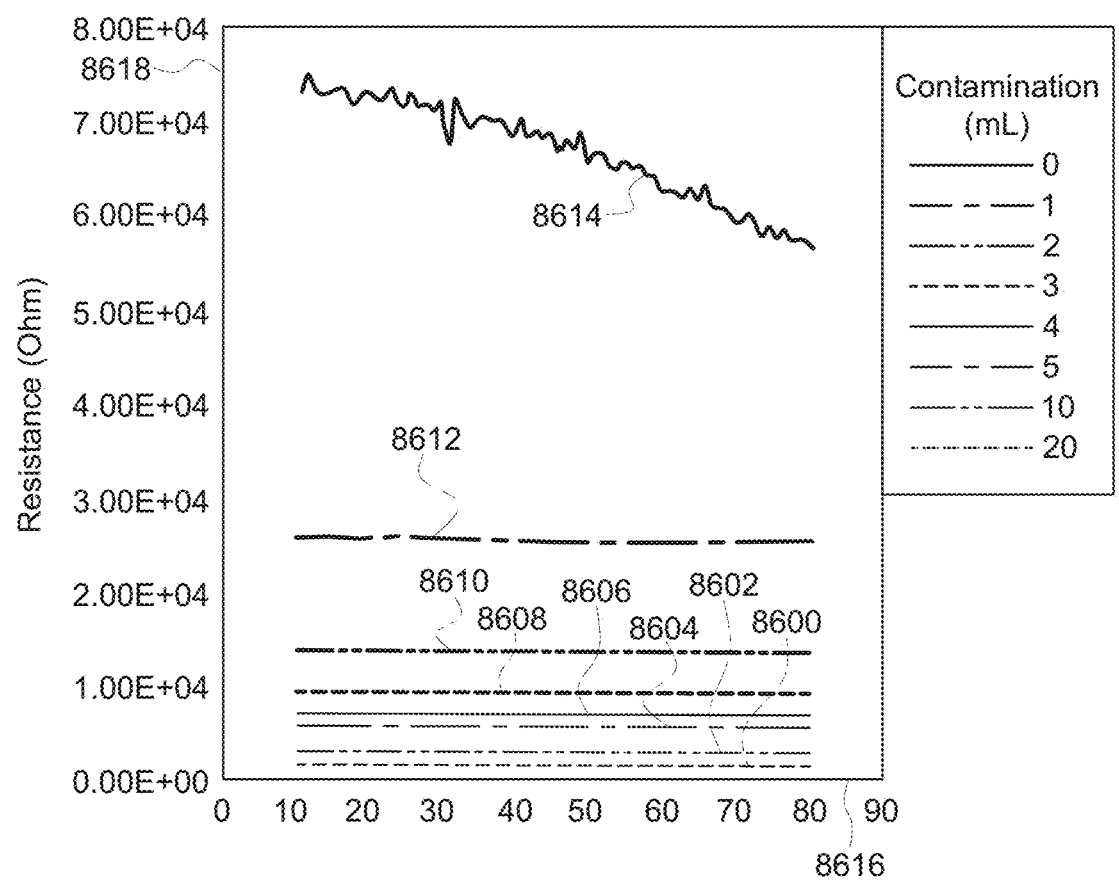
FIG. 86 illustrates measured resistances for different levels of the contaminant in the fluid under examination according to the example of FIG. 85.

FIG. 86 illustrates measured resistances 8600, 8602, 8604, 8606, 8608, 8610, 8612, 8614 for different levels of the contaminant in the fluid under examination according to the example of FIG. 85. The measured resistances 8600, 8602, 8604, 8606, 8608, 8610, 8612, 8614 are shown alongside a horizontal axis 8616 representative of frequency (e.g., in units related to hertz) and a vertical axis 8618 representative of resistance measured by the sensor assembly 8000 (e.g., in units of ohms). The sensor reader 8008 used a frequency-sweeping process to examine a range of frequencies of electric fields to measure the resistances 8600, 8602, 8604, 8606, 8608, 8610, 8612, 8614 shown in FIG. 86. The fluid under examination in FIG. 86 was the same fluid with the capacitances shown in FIG. 85. The table below lists the level (e.g., amount) of water for each of the resistances in the resistances 8600, 8602, 8604, 8606, 8608, 8610, 8612, 8614 that were measured.

| Capacitances | Level of Water in Ethanol (in milliliters) |
| --- | --- |
| 8600 | 20 |
| 8602 | 10 |
| 8604 | 5 |
| 8606 | 4 |
| 8608 | 3 |
| 8610 | 2 |
| 8612 | 1 |
| 8614 | 0 |

In another demonstration, the application specific integrated circuit available from Analog Devices (Model AD5933) was used as the sensor reader 8008 and was connected to an IDE sensor structure coated with a vapor-sensing film comprised of ligand-capped metal nanoparticles. This IDE sensor structure operated in a non-resonant mode because the sensor did not include an inductor in its circuit. Measurements were performed at multiple frequencies over the range from 1 kHz to 100 kHz upon periodic exposure of the IDE sensor to three vapors at their two concentrations each. Vapor 1 was water vapor, vapor 2 was toluene vapor, and vapor 3 was ethyl acetate vapor. These vapors were used as model vapors to demonstrate the applicability of the developed sensor system. The integrated circuit Analog Devices Model AD5933 provided several analog outputs measured from the sensor as a function of frequency. Nonlimiting examples of these outputs include the real part of impedance (Zre), the imaginary part of impedance (Zim), magnitude, phase, equivalent sensor capacitance (Cp), and equivalent sensor resistance (Rp).

Figure 87:
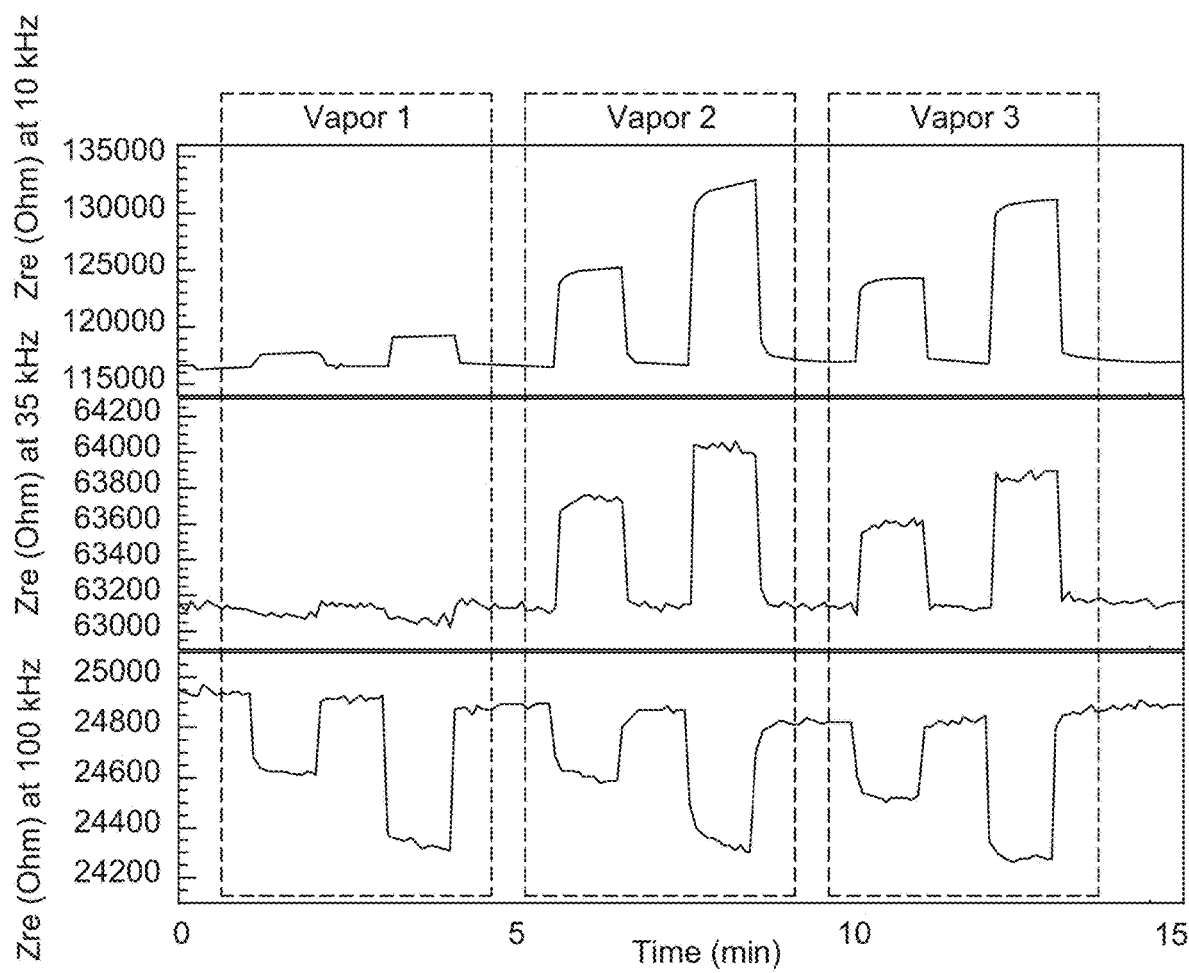
FIG. 87 depicts an example of sensor response Zre as a function of experimental time at three frequencies such as 10 kHz, 35 kHz, and 100 kHz.

FIG. 87 depicts an example of sensor response Zre as a function of experimental time at three frequencies such as 10 kHz, 35 kHz, and 100 kHz. During the experiment, the sensor assembly 8000 was first exposed to vapor 1 at a relatively small concentration followed by sensor exposure to a higher concentration of vapor 1. Next, the sensor assembly 8000 was exposed to vapor 2 at a relatively small concentration followed by sensor exposure to a higher concentration of vapor 2. Finally, the sensor assembly 8000 was exposed to vapor 3 at a relatively small concentration followed by sensor exposure to a higher concentration of vapor 3. All exposures of the sensor assembly 8000 to vapors were performed with 60-second durations. The sensor assembly 8000 was exposed to a blank carrier gas (dry air) between exposures to vapors. Each vapor produced a different response pattern at these three displayed frequencies. For example, vapor 1 produced a relatively small positive response at 10 kHz in relation to other two vapors.

At 35 kHz, vapor 1 produced also a relatively small response in relation to other two vapors but with the negative direction of the response. At 100 kHz, vapor 1 produced a response that was comparable with the responses to other two vapors. Response to vapor 2 was slightly larger than response to vapor 3 at 10 kHz and at 35 kHz and was comparable to response to vapor 3 at 100 kHz. These results demonstrate that measurements of outputs at different frequencies from a non-resonant sensor assembly 8000 using the application specific integrated circuit provided desired diverse responses which are needed for differentiation of different vapors.

Figure 88:
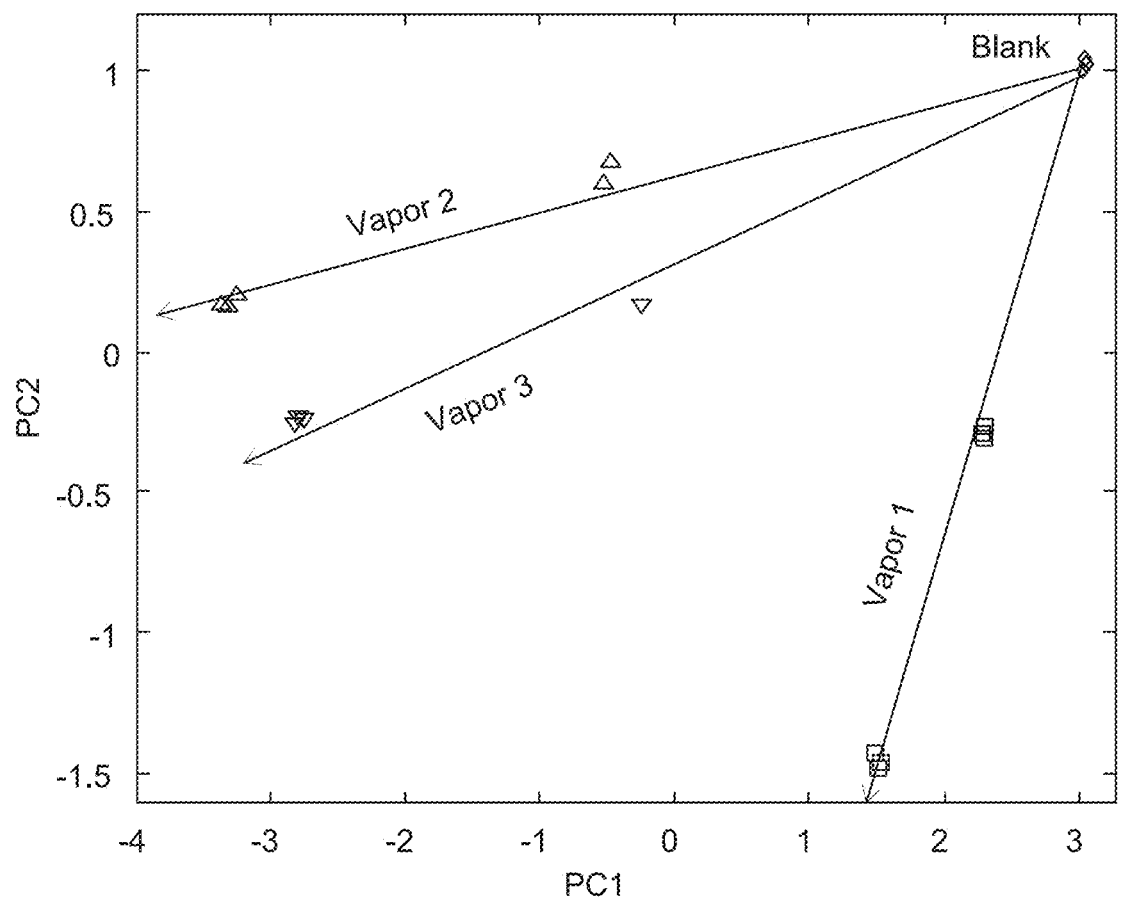
FIG. 88 depicts a scores plot of a developed PCA model based on the sensor response results presented in FIG. 87.

FIG. 88 depicts a scores plot of a developed PCA model based on the sensor response results presented in FIG. 87. This plot illustrates that the sensor assembly 8000 was able to differentiate between the three vapors. The different directions of the sensor responses to vapors 1, 2, and 3 were indicated with arrows in FIG. 88.

Figure 89:
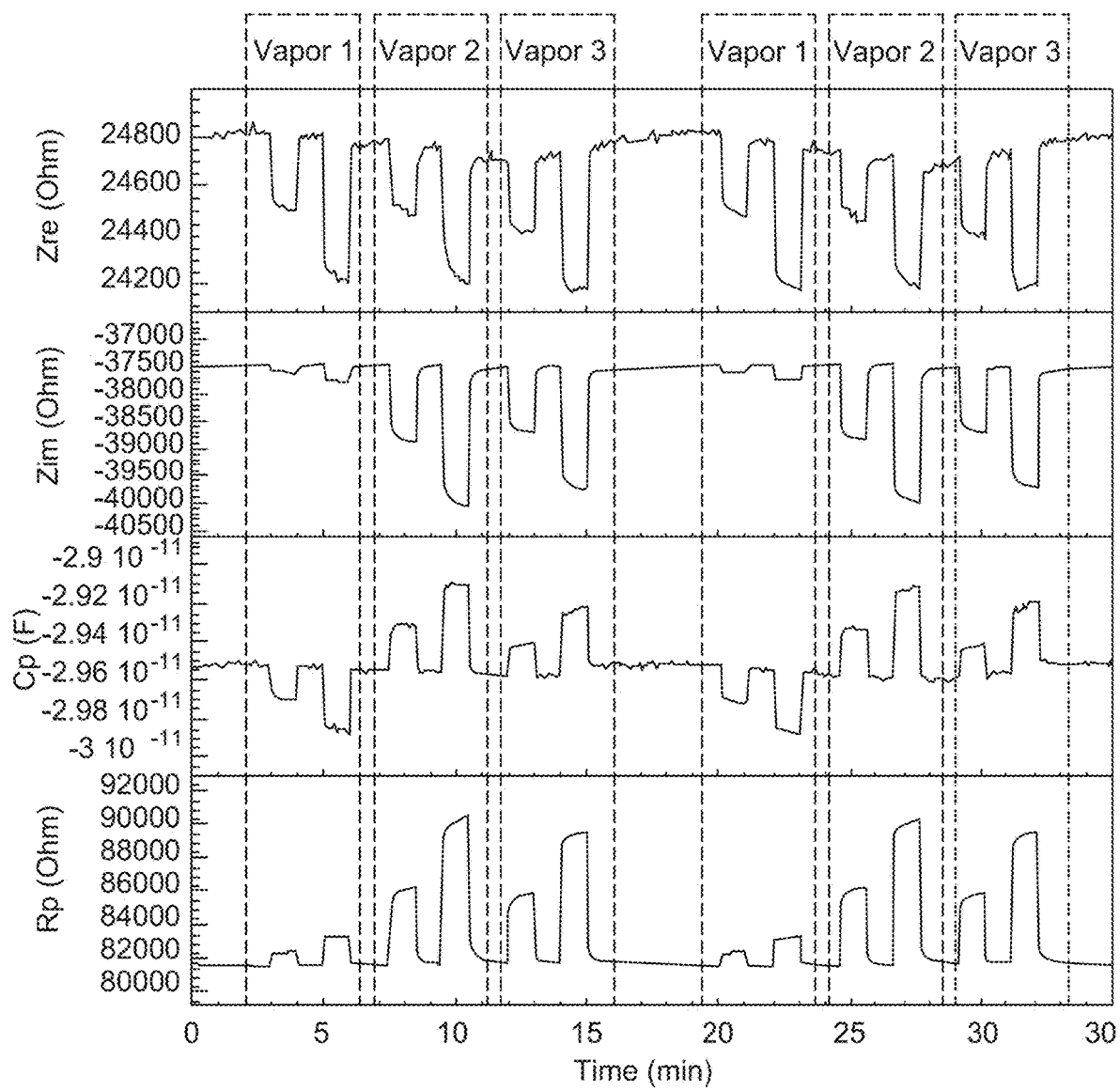
FIG. 89 depicts an example of sensor responses Zre (the real part of impedance), Zim (the imaginary part of impedance), Cp (equivalent sensor capacitance), and Rp (equivalent sensor resistance), all measured at a single frequency of 100 kHz and using the sensor assembly and sensor reader described in relation to FIG. 87.

FIG. 89 depicts an example of sensor responses Zre (the real part of impedance), Zim (the imaginary part of impedance), Cp (equivalent sensor capacitance), and Rp (equivalent sensor resistance), all measured at a single frequency of 100 kHz and using the sensor assembly 8000 and sensor reader described in relation to FIG. 87. Same as in FIG. 87, these measurements were performed by exposing the same sensor assembly 8000 to the same three vapors. Unlike FIG. 87, the measurements were performed with two replicates. These results demonstrate that measurements of different outputs from a sensor assembly 8000 using the application specific integrated circuit provided desired diverse responses Zre, Zim, Cp, and Rp as measured at a single frequency. Such measured response diversity is needed for differentiation of different vapors.

Measurements of another sensor assembly 8000 were performed upon excitation of the sensor assembly at multiple frequencies. The sensor reader 8008 was sweeping through the frequencies by changing the frequency of the electric field in a continuous manner. The sensor assembly 8000 had an IDE structure coated with a vapor-sensing film comprised of ligand-capped metal nanoparticles and one inductor. The presence of one inductor produced a resonant circuit with the measured parameters of the circuit Fp, Fz, Zp, F1, F2, Z1, and Z2 as described in FIG. 23. The sensor assembly 8000 was periodically exposed to four vapors at their four concentrations each. The four vapors 1-4 were water, methyl salicylate, toluene, and acetone. These vapors were used as model vapors to demonstrate the applicability of the developed sensor system. Collected responses Fp, Fz, Zp, F1, F2, Z1, and Z2 were analyzed using PCA.

Figure 90:
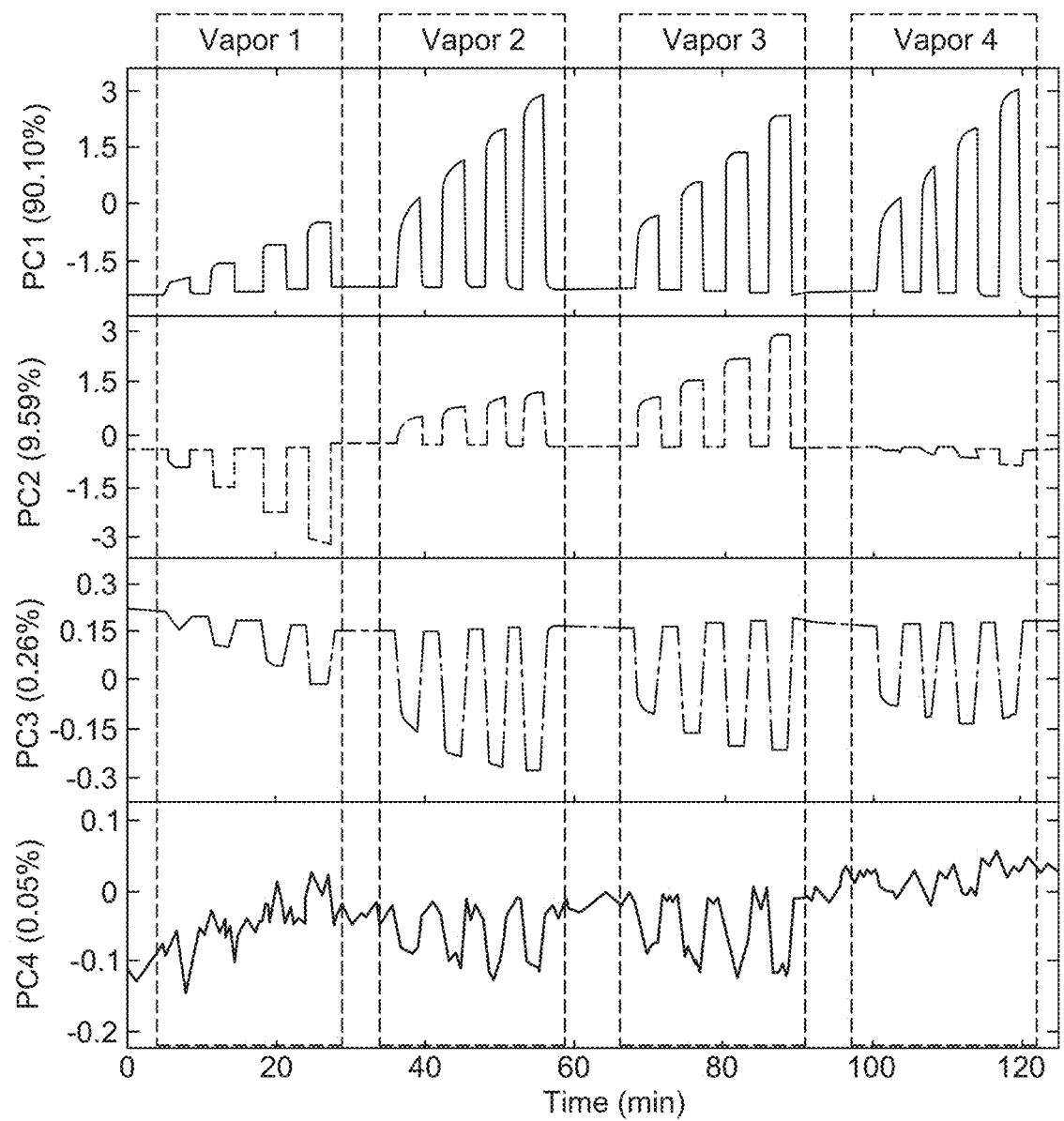
FIG. 90 illustrates plots of the first four principal components (PCs) of the developed PCA model as a function of experimental time during exposures to vapors that show the distinct recognition pattern up to PC4 between four model vapors at their four concentration levels.

FIG. 90 illustrates plots of the first four principal components (PCs) of the developed PCA model as a function of experimental time during exposures to vapors that show the distinct recognition pattern up to PC4 between four model vapors at their four concentration levels. These results are of significant importance for the ability of a single sensor assembly 8000 to differentiate between multiple vapors.

Control of detection sensitivity of impedance measurements has been demonstrated in the present disclosure in the resonant and non-resonant (conventional) detection modes. When detection sensitivity was compared between resonant and conventional impedance measurements, sensitivity enhancement of up to ~74 fold was achieved for resonant vs. conventional impedance measurements.

Figure 91:
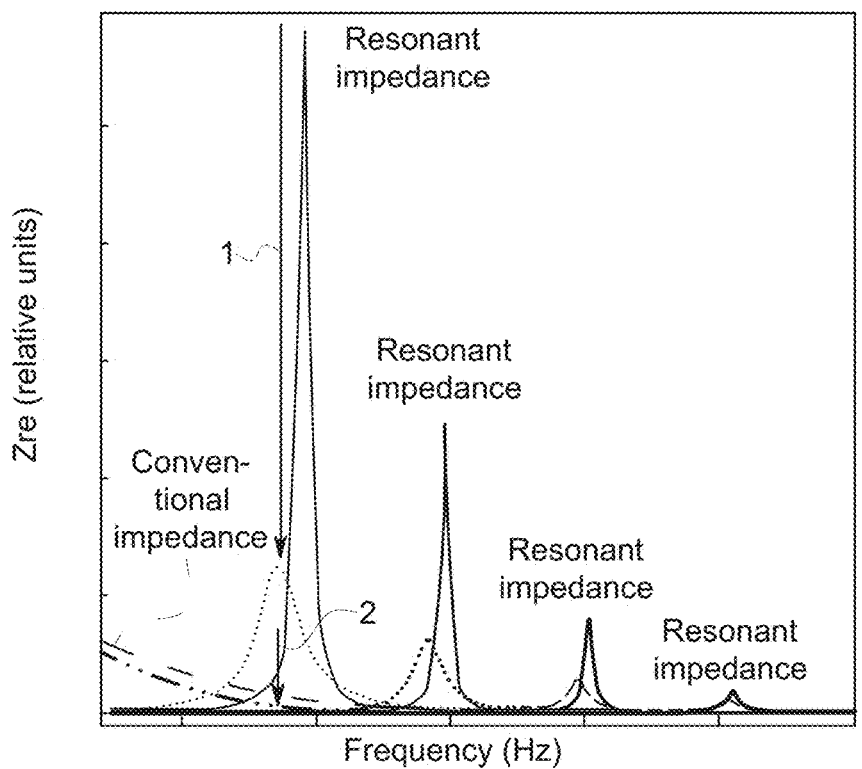
FIG. 91 depicts results of dynamic measurements of a solution with a sensor assembly over time when the changes in the solution properties were measured using resonant impedance (two lines and an arrow 1 illustrating response direction for the lowest frequency resonator) and conventional impedance (two lines and an arrow 2 illustrating response direction).

FIG. 91 depicts results of dynamic measurements of a solution with a sensor assembly 8000 over time when the changes in the solution properties were measured using resonant impedance (two lines and an arrow 1 illustrating response direction for the lowest frequency resonator) and conventional impedance (two lines and an arrow 2 illustrating response direction). Resonant impedance measurements were performed with four resonators. The enhancement of the measurement sensitivity using resonant impedance over conventional impedance was calculated as the ratio of response sensitivity measured using a particular resonator (length of arrow 1 in FIG. 91) to the response sensitivity measured using conventional impedance at the same frequency range as the resonator (length of arrow 2 in FIG. 91). In FIG. 91, the ratio between sensitivity of the resonator that operated at the smallest resonant frequency and the sensitivity using conventional impedance was ~74 (the ratio of the length of arrow 1 to the length of arrow 2). This value indicated the enhancement of the measurement sensitivity using resonant impedance over conventional impedance. The sensor assembly used in this experiment was an interdigital electrode structure coated with a dielectric protective layer. The layer thickness and the geometry of the electrode structure provided the control of the enhancement of the measurement sensitivity using resonant impedance over conventional impedance.

Figure 92:
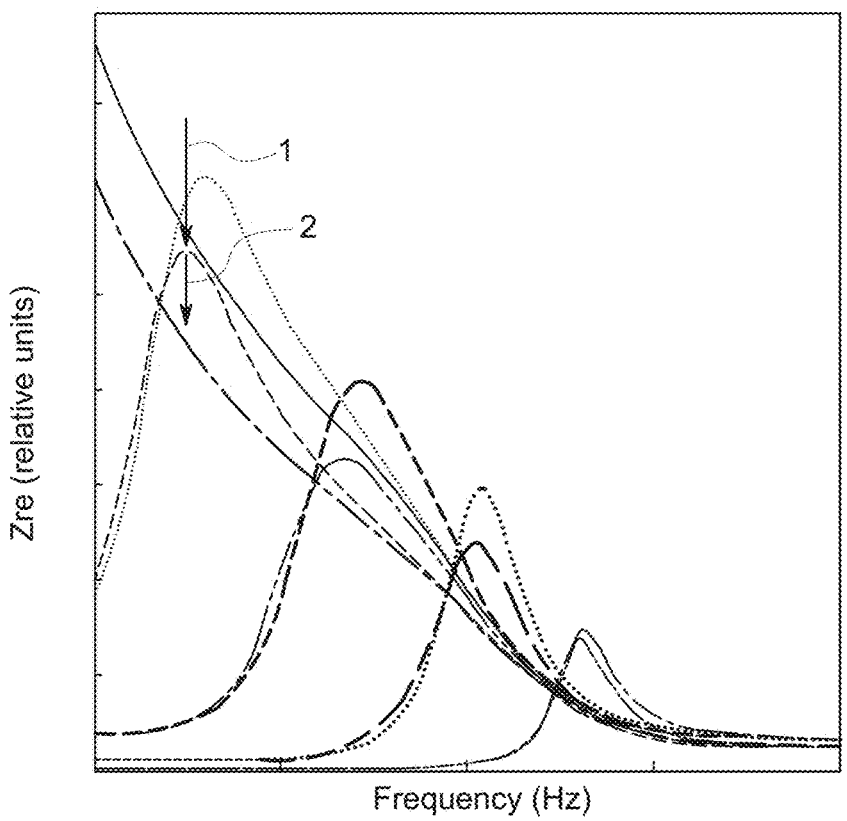
FIG. 92 depicts results of dynamic measurements of a solution over time when the changes in the solution properties were measured using resonant impedance (two lines and an arrow 1 illustrating response direction for the lowest frequency resonator) and conventional impedance (two lines and an arrow 2 illustrating response direction).

FIG. 92 depicts results of dynamic measurements of a solution over time when the changes in the solution properties were measured using resonant impedance (two lines and an arrow 1 illustrating response direction for the lowest frequency resonator) and conventional impedance (two lines and an arrow 2 illustrating response direction). This sensor assembly did not have a protective dielectric layer. In FIG. 92, the ratio between sensitivity of the resonator that operated at the smallest resonant frequency and the sensitivity using conventional impedance was approximately a unity (the ratio of the length of arrow 1 to the length of arrow 2). This value indicated no enhancement of the measurement sensitivity using resonant impedance over conventional impedance when the sensor had the described configuration.

In another demonstration, the application specific integrated circuit available from AMS (Model SL900A) was used as the sensor reader 8008 and was connected to a single IDE sensor structure coated with a vapor-sensing film comprised of ligand-capped metal nanoparticles. Alternatively, it was connected to two IDE sensor structures, each coated with a vapor-sensing film comprised of ligand-capped metal nanoparticles. This sensor system operated in a non-resonant mode because it did not include an inductor in its circuit. Alternatively, this sensor system may operate when the connected sensor or sensors include an inductor. The sensor reader measured capacitance and resistance of the sensor or sensors connected to the two inputs of the sensor reader. Measurements were performed at two frequencies, one frequency for capacitance measurements and another frequency for resistance measurements. Measurements of capacitance and for resistance at different frequencies allows enhancement of selectivity of the response of the sensor system to different vapors or fluids. The sensor system was periodically exposed to four vapors at their two concentrations each. Vapor 1 was water vapor, vapor 2 was isopropyl alcohol vapor, vapor 3 was methanol vapor, and vapor 4 was toluene vapor. These vapors were used as model vapors to demonstrate the applicability of the developed sensor system. The integrated circuit AMS Model SL900A provided two digital outputs measured from the connected sensor or sensors.

Figure 93:
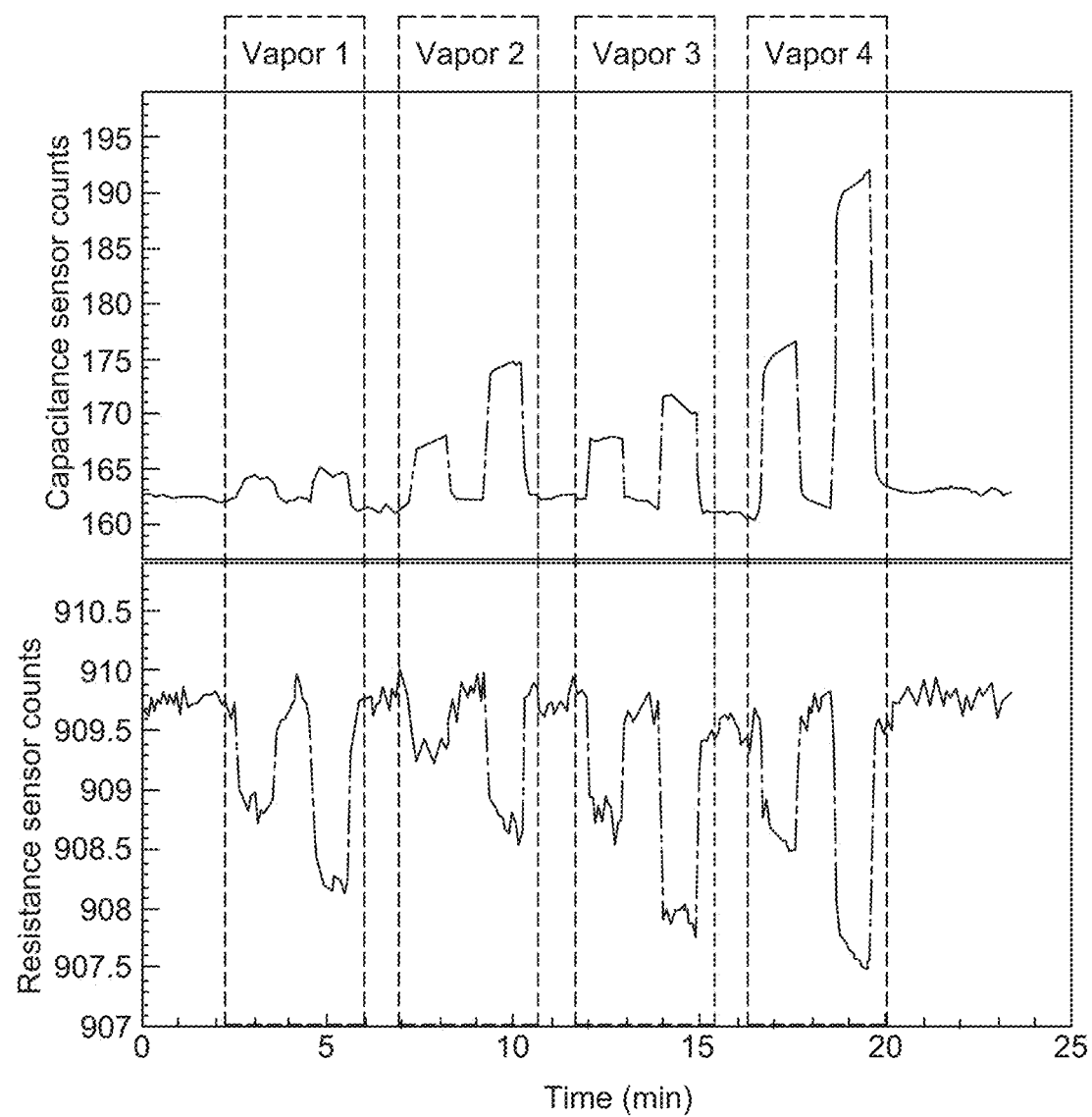
FIG. 93 illustrates capacitance response and resistance response of the sensor assembly under examination of a fluid such as vapors as measured by the sensor assembly in accordance with one example.

FIG. 93 illustrates capacitance response and resistance response of the sensor assembly under examination of a fluid such as vapors as measured by the sensor assembly 8000 in accordance with one example. The sensor system shows the responses in counts because the original measured values of capacitance and resistance are digitized in the sensor reader AMS Model SL900A for wireless or wired transmission to the end-user. The sensor assembly 8000 measured the capacitances and resistances in ambient air.

The term "fluids" can include gases, vapors, liquids, and solids and their combinations forming multiphase compositions. Non-limiting examples of multiphase compositions include emulsions such as oil/water emulsions, food emulsions such as salad dressings oil-in-water emulsions, colloids such as solutions that have particles distributed throughout the solution, food colloids, food colloids such as ice scream, jam, mayonnaise, solid foams such as bread, cake. Fluid can also include a food product that has been gone through mechanical re-forming. Alternatively, a fluid may not include a solid.

The term "analyte" can include a substance or chemical constituent that is the subject of a chemical analysis. Examples of analytes include, but are not limited to, water, fuel, hydrogen, carbon monoxide, carbon dioxide, methane, ethane, ethylene, acetylene, acids, metals, aging products, or any combination thereof. In certain embodiments, the sensing materials of the present disclosure may be configured to detect analytes.

The term "multivariable sensor" can refer to a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof.

The term "multivariate analysis" can refer to a mathematical procedure that is used to analyze more than one variable from the sensor response and to provide the information about the type of at least one environmental parameter from the measured sensor parameters and/or to quantitative information about the level of at least one environmental parameter from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" can refer to measurable variables of the sensor response. The sensor response is the impedance spectrum of the LCR sensor. In addition to measuring the impedance spectrum in the form of Z-parameters, S-parameters, and other parameters, the impedance spectrum (for example, both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F1), the anti-resonant frequency of the imaginary part of the impedance (F2), signal magnitude (Z1) at the resonant frequency of the imaginary part of the impedance (F1), signal magnitude (Z2) at the anti-resonant frequency of the imaginary part of the impedance (F2), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra may also be called "features" or "descriptors." The appropriate selection of features is performed from all potential features that can be calculated from spectra.

As used herein, the term "sensing materials and sensing films" can include, but is not limited to, materials deposited onto an electronics module of a transducer, such as LCR circuit components to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system," "module," or "controller" may include hardware and/or software that operate(s) to perform one or more functions. For example, a system, module, or controller may include a computer processor or other logic-based device that performs operations based on instructions stored on a tangible and non-transitory computer readable storage medium, such as a computer memory. Alternatively, a system, module, or controller may include a hard-wired device that performs operations based on hard-wired logic of the device. The systems, modules, and controllers shown in the Figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or examples thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor system comprising:
   a sensor assembly performing multi-frequency operations disposed in a single, contiguous sensor body, wherein the contiguous sensor body is configured to be in operational contact with a fluid; and
   a sensor reader disposed in the contiguous sensor body, wherein
      the sensor assembly is communicatively coupled to the sensor reader within the contiguous sensor body, wherein the sensor assembly comprises
         a single sensing region comprising an interdigitated electrode, and
         a plurality of tuning elements electrically coupled to the single sensing region, wherein each tuning element of the plurality of tuning elements generates a resonant circuit with the single sensing region having a respective resonant frequency range,
      wherein the sensor assembly is configured to generate respective electric fields having frequencies over the respective resonant frequency ranges of the respective resonant circuits in the fluid, and
      wherein the sensor reader includes one or more processors configured to examine respective impedance responses of the sensor assembly based on generating the respective electric fields to determine one or more properties of the fluid based on the examined respective impedance responses.

2. The sensor system of claim 1, wherein the sensor reader is configured to acquire measurements of the respective impedance responses from the sensor assembly at a resolution of one or more of 8 bit, 12 bit, or 16 bit.

3. The sensor system of claim 1, wherein the sensor reader is configured to acquire measurements of the one or more properties of the fluid at a resolution greater than 16 bit by one or more of filtering or averaging the measurements.

4. The sensor system of claim 1, wherein the contiguous sensor body is configured to protect the sensor assembly and the sensor reader from damage caused by temperatures up to 250 degrees Celsius.

5. The sensor system of claim 1, wherein the contiguous sensor body is configured to operate the sensor assembly and the sensor reader at temperatures up to 250 degrees Celsius.

6. The sensor system of claim 1, wherein the sensor assembly is configured to generate an electrical signal representative of the respective impedance responses after generating the respective electric fields in the fluid.

7. The sensor system of claim 1, wherein the sensor assembly is communicatively coupled to the sensor reader within the contiguous sensor body via one or more wireless connections.

8. The sensor system of claim 1, wherein the interdigitated electrode is coated with a sensing film.

9. The sensor system of claim 1, wherein the sensor reader is configured to examine respective impedance responses based on different resonant frequencies associated with each tuning element of the plurality of tuning elements.

10. A sensor system comprising:
    a sensor assembly performing multi-frequency operations disposed in a single, contiguous sensor body, wherein the contiguous sensor body is configured to be in operational contact with an industrial fluid; and
    a sensor reader disposed in the contiguous sensor body, wherein
       the sensor assembly is communicatively coupled to the sensor reader within the contiguous sensor body, wherein the sensor assembly comprises
          a single sensing region comprising an interdigitated electrode, and
          a plurality of tuning elements electrically coupled to the single sensing region, wherein each tuning element of the plurality of tuning elements generates a resonant circuit with the single sensing region having a respective resonant frequency range,
       wherein the sensor assembly is configured to generate respective electric fields having frequencies over the respective resonant frequency ranges of the respective resonant circuits in the industrial fluid, and
       wherein the sensor reader includes one or more processors configured to examine respective impedance spectra of the sensor assembly based on generating the respective electric fields to determine one or more properties of the industrial fluid based on the examined respective impedance spectra.

11. The sensor system of claim 10, wherein the sensor assembly is a non-resonant circuit for different frequencies of the respective electric fields generated by the sensor assembly in the industrial fluid.

12. The sensor system of claim 10, wherein the sensor assembly is a resonant circuit for different frequencies of the respective electric fields generated by the sensor assembly in the industrial fluid.

13. The sensor system of claim 10, wherein the different frequencies comprise non-harmonic resonant frequencies.

14. The sensor system of claim 10, wherein the sensor assembly is configured to generate the different frequencies by sweeping through the frequency range.

15. The sensor system of claim 10, wherein the sensor assembly is configured to generate the different frequencies by stepping through the frequency range such that discrete frequencies of the different frequencies are generated at respective times for different, non-zero periods of time.

16. The sensor system of claim 10, wherein the sensor reader is configured to communicate a digital output signal to an external controller that represents at least one of the respective impedance spectra of the sensor assembly or at least one of the one or more properties of the industrial fluid.

17. The sensor system of claim 16, wherein the sensor reader is configured to communicate the digital output signal to the external controller via a wireless signal or a wired connection.

18. The sensor system of claim 10, wherein the sensor reader has a digital address for communication with an external controller.

19. The sensor system of claim 10, wherein the sensor reader is configured to provide digital data security for communication between the sensor reader and one or more external controllers.

20. The sensor system of claim 10, wherein the sensor assembly is configured to be powered via ambient energy harvesting.

* * * * *